United States Patent
Olasagasti et al.

(10) Patent No.: US 9,481,908 B2
(45) Date of Patent: Nov. 1, 2016

(54) COMPOSITIONS, DEVICES, SYSTEMS, AND METHODS FOR USING A NANOPORE

(71) Applicant: The Regents of the University of California, Oakland, CA (US)

(72) Inventors: Felix A. Olasagasti, Vitoria-Gasteiz (ES); Kathy R. Lieberman, Santa Cruz, CA (US); Seico Benner, Ustunomiya (JP); Mark A. Akeson, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 137 days.

(21) Appl. No.: 14/192,785

(22) Filed: Feb. 27, 2014

(65) Prior Publication Data

US 2014/0255918 A1 Sep. 11, 2014

Related U.S. Application Data

(60) Division of application No. 12/459,059, filed on Jun. 26, 2009, now Pat. No. 8,679,747, which is a continuation-in-part of application No. PCT/US2008/004467, filed on Apr. 4, 2008.

(60) Provisional application No. 60/921,787, filed on Apr. 4, 2007, provisional application No. 60/931,115, filed on May 21, 2007, provisional application No. 60/962,530, filed on Jul. 30, 2007, provisional application No. 60/967,539, filed on Sep. 4, 2007, provisional application No. 61/062,391, filed on Jan. 25, 2008.

(51) Int. Cl.
*C12Q 1/68* (2006.01)
*C07H 21/00* (2006.01)
*G01N 33/487* (2006.01)
*C25B 3/10* (2006.01)

(52) U.S. Cl.
CPC ........... *C12Q 1/6874* (2013.01); *C12Q 1/6869* (2013.01); *C25B 3/10* (2013.01); *G01N 33/48721* (2013.01)

(58) Field of Classification Search
CPC ................................ C12Q 1/68; C07H 21/00
See application file for complete search history.

(56) References Cited

U.S. PATENT DOCUMENTS

| | | |
|---|---|---|
| 5,474,796 A | 12/1995 | Brennan |
| 5,593,840 A | 1/1997 | Bhatnagar et al. |
| 5,605,662 A | 2/1997 | Heller |
| 5,795,782 A | 8/1998 | Church |
| 5,932,451 A | 8/1999 | Wang |
| 6,015,714 A | 1/2000 | Baldarelli |
| 6,114,121 A | 9/2000 | Fujiwara et al. |
| 6,197,526 B1 | 3/2001 | Yu et al. |
| 6,267,872 B1 | 7/2001 | Akeson |
| 6,362,002 B1 | 3/2002 | Denison |
| 6,428,959 B1 | 8/2002 | Deamer |
| 6,464,842 B1 | 10/2002 | Golovchenko |
| 6,579,682 B1 | 6/2003 | Innerarity et al. |
| 6,617,113 B2 | 9/2003 | Deamer |
| 6,627,067 B1 | 9/2003 | Branton |
| 6,632,610 B2 | 10/2003 | Thill |
| 6,673,615 B2 | 1/2004 | Denison |
| 6,746,594 B2 | 6/2004 | Akeson |
| 7,189,503 B2 | 3/2007 | Akeson |
| 7,501,279 B2 | 3/2009 | Folch et al. |
| 8,500,982 B2 | 8/2013 | Akeson et al. |
| 2001/0010913 A1 | 8/2001 | Hillman |
| 2003/0104428 A1 | 6/2003 | Branton |
| 2004/0121525 A1 | 6/2004 | Chopra |
| 2004/0149580 A1 | 8/2004 | Flory |
| 2005/0009004 A1 | 1/2005 | Xu et al. |
| 2005/0053961 A1 | 3/2005 | Akeson |
| 2005/0127035 A1 | 6/2005 | Ling |
| 2005/0136408 A1 | 6/2005 | Tom-Moy et al. |
| 2006/0019247 A1 | 1/2006 | Su et al. |
| 2006/0063171 A1 | 3/2006 | Akeson et al. |
| 2006/0073489 A1 | 4/2006 | Li et al. |

(Continued)

FOREIGN PATENT DOCUMENTS

EP 1486775 A1 12/2004
JP 2005-519622 A 7/2005

(Continued)

OTHER PUBLICATIONS

Kasianowicz et al., "Characterization of individual polynucleotide molecules using a membrane channel," Proc. Natl. Acad. Sci. USA (Nov. 1998), pp. 13770-13773, vol. 93.
Kashima et al., "Unique structure of murine interleukin-2 as deduced from cloned cDNAs," Nature (Jan. 31, 1985), pp. 402-404, vol. 313.
Metzker, "Emerging technologies in DNA sequencing," Genome Research (2005), pp. 1767-1776, vol. 15.

(Continued)

*Primary Examiner* — Ethan C Whisenant
(74) *Attorney, Agent, or Firm* — Brian E. Davy; Bozicevic, Field & Francis LLP

(57) ABSTRACT

The invention herein disclosed provides for devices and methods that can detect and control an individual polymer in a mixture is acted upon by another compound, for example, an enzyme, in a nanopore in the absence of requiring a terminating nucleotide. The devices and methods are also used to determine rapidly (~>50 Hz) the nucleotide base sequence of a polynucleotide under feedback control or using signals generated by the interactions between the polynucleotide and the nanopore. The invention is of particular use in the fields of drug discovery, molecular biology, structural biology, cell biology, molecular switches, molecular circuits, and molecular computational devices, and the manufacture thereof.

17 Claims, 30 Drawing Sheets

(56) References Cited

U.S. PATENT DOCUMENTS

| | | |
|---|---|---|
| 2007/0099191 A1 | 5/2007 | Nair et al. |
| 2010/0121582 A1 | 5/2010 | Pan et al. |
| 2011/0005918 A1 | 1/2011 | Akeson |
| 2011/0174625 A1 | 7/2011 | Akeson et al. |
| 2013/0118902 A1 | 5/2013 | Akeson et al. |
| 2014/0034517 A1 | 2/2014 | Akeson et al. |
| 2014/0051068 A1 | 2/2014 | Cherf et al. |
| 2014/0346059 A1 | 11/2014 | Akeson et al. |
| 2016/0040230 A1 | 2/2016 | Akeson et al. |

FOREIGN PATENT DOCUMENTS

| | | |
|---|---|---|
| WO | WO 94/25662 A1 | 11/1994 |
| WO | WO 95/25116 | 9/1995 |
| WO | WO 95/35505 | 12/1995 |
| WO | WO 00/79257 A1 | 12/2000 |
| WO | 02/42496 A2 | 5/2002 |
| WO | 03/078649 A2 | 9/2003 |
| WO | 2006/020775 A2 | 2/2006 |
| WO | 2006/028508 A2 | 3/2006 |
| WO | 2008/005674 A2 | 1/2008 |
| WO | WO 2008/124107 A1 | 10/2008 |
| WO | 2009/077734 A2 | 6/2009 |
| WO | 2010/122293 A1 | 10/2010 |

OTHER PUBLICATIONS

Rhee and Burns, "Nanopore sequencing technology: research trends and applications," Trends in Biotechnology (Oct. 2006), pp. 580-586, vol. 24.

Gordon et al., "Consed: a graphical tool for sequence finishing," Genome Research (1998), pp. 195-202, vol. 8.

Schena et al., "Parallel human genome analysis: Microarray-based expression monitoring of 1000 genes," Proc. Natl. Acad. Sci. USA (Oct. 1996), pp. 10614-10619, vol. 93.

Heller et al., "Discovery and analysis of inflammatory disease-related genes using cDNA microarrays," Proc. Natl. Acad. Sci. USA (Mar. 1997), pp. 2150-2155, vol. 94.

Vercoutere et al., "Rapid discrimination among individual DNA hairpin molecules at single-nucleotide resolution using an ion channel," Nature Biotechnology (Mar. 2001), pp. 248-252, vol. 19.

Vercoutere et al., "Discrimination among individual Watson-Crick base pairs at the temini of single DNA hairpin molecules," Nucleic Acids Research (2003), pp. 1311-1318, vol. 31.

Abbondanzieri et al., "Direct observation of base-pair stepping by RNA polymerase," Nature (Nov. 2005), pp. 460-465, vol. 438.

Greenleaf and Block, "Single-molecule, motion-based DNA sequencing using RNA polymerase," Science (Aug. 2006), p. 801, vol. 313.

Hornblower et al., "Single-molecule analysis of DNA-protein complexes using nanopores," Nature Methods (Apr. 2007), pp. 315-317, vol. 4.

Winters-Hilt et al., "Highly accurate classification of Watson-Crick basepairs on termini of single DNA molecules," Biophysical Journal (Feb. 2003), pp. 967-976, vol. 84.

Bates et al., "Dynamics of DNA molecules in a membrane channel probed by active control techniques," Biophysical Journal (Apr. 2003), pp. 2366-2372, vol. 84.

Wilson et al., "Feedback control of a DNA molecule tethered in a nanopore to repeatedly probe DNA-binding enzymes," Conf. Proc. IEEE Eng. Med. Biol. Soc. (2008a), 30th Annual International IEEE EMBS Conference, pp. 5745-5748.

Bustamante et al., "Ten years of tension: single-molecule DNA mechanics," Nature (Jan. 2003), pp. 423-427, vol. 421.

Benner et al., "Sequence-specific detection of individual DNA polymerase complexes in real time using a nanopore," Nature Nanotechnology (Nov. 2007), pp. 718-724, vol. 2.

Sanger and Coulson, "A rapid method for determining sequences in DNA by primed synthesis with DNA polymerase," Journal of Moleculear Biology (1975), pp. 441-448, vol. 94.

Wilson et al., "Rapid finite state machine control of individual DNA molecules in a nanopore," International Conference on Biomedical Electronics and Devices (2008b), pp. 94-98, Madiera, Portugal.

Astier et al., "Stochastic detection of motor protein-RNA complexes by single-channel current recording," ChemPhysChem (2007), pp. 2189-2194, vol. 8.

Nielsen et al., "An introduction to peptide nucleic acid", Current Issues Molec. Biol. (1999) 1(2); 89-104.

Andersson, et al., "Detection of Single Ion Channel Activity on a Chip Using Tethered Bilayer Membranes," American Chemical Society (Feb. 28, 2007), 4 pp.

Castellana and Cremer, "Solid supported lipid bilayers: From biophysical studies to sensor design," ScienceDirect, Surface Science Reports 61 (2006), pp. 429-444.

Baaken et al., "Planar microelectrode-cavity array for high-resolution and parallel electrical recording of membrane ionic currents," Lab Chip, (2008) vol. 8, pp. 938-944.

Bayley and Cremer, "Stochastic sensors inspired by biology," Nature, vol. 413, (Sep. 13, 2001), pp. 226-230.

Tanaka and Sackmann, "Polymer-supported membranes as models of the cell surface," Nature, vol. 437 (Sep. 29, 2005), pp. 656-663.

Office Action, JP Patent Application No. 2014-225711, Oct. 27, 2015, 3 pp.

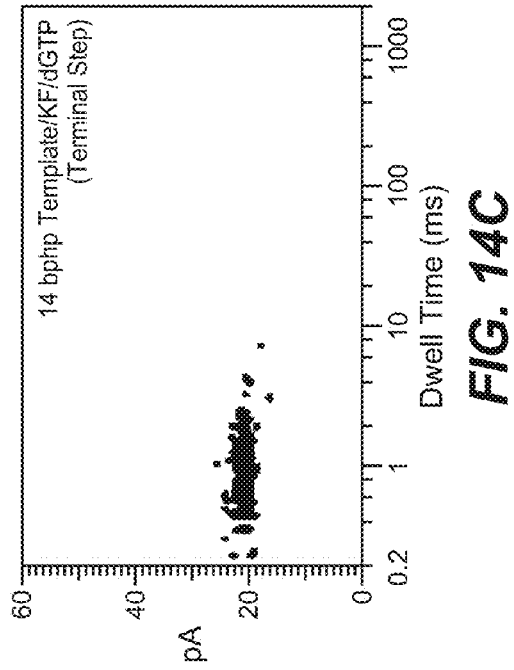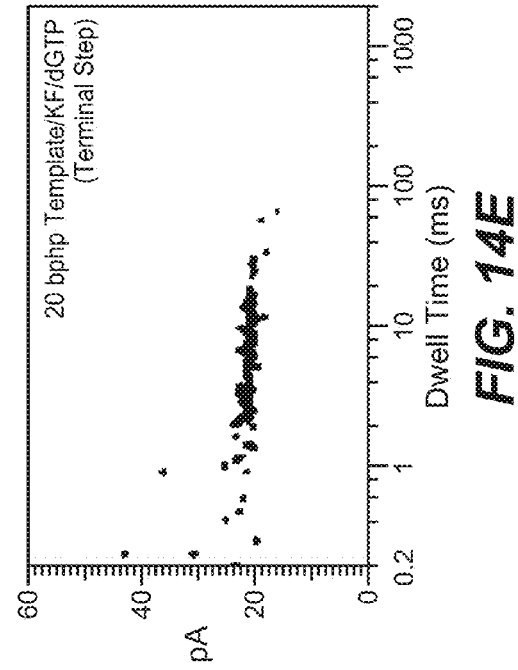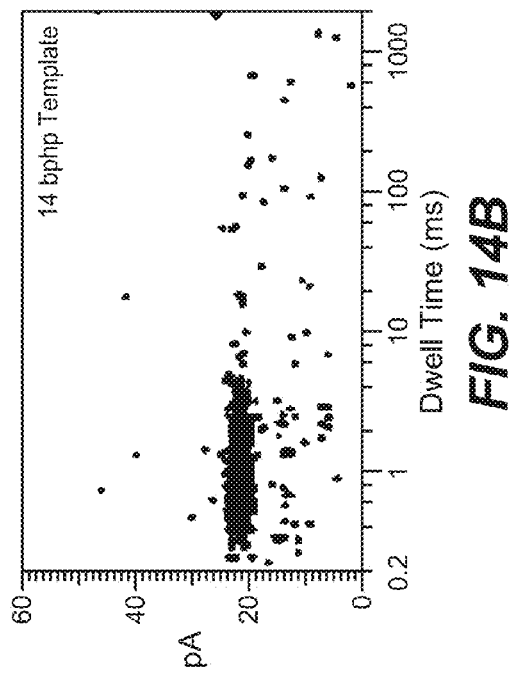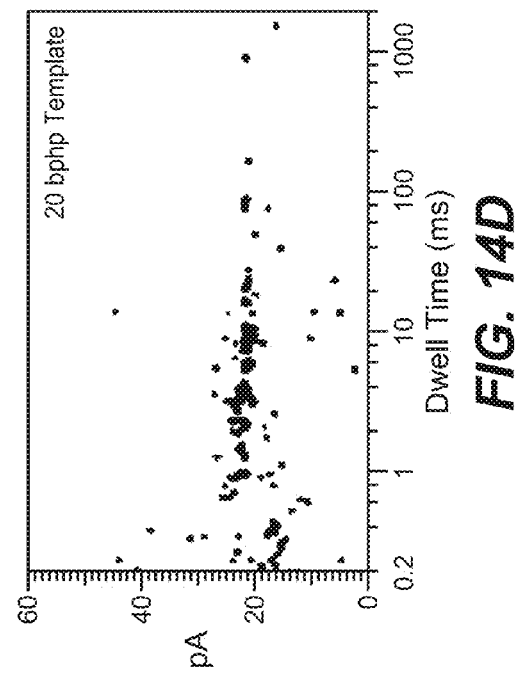
FIG. 14C
FIG. 14E
FIG. 14B
FIG. 14D

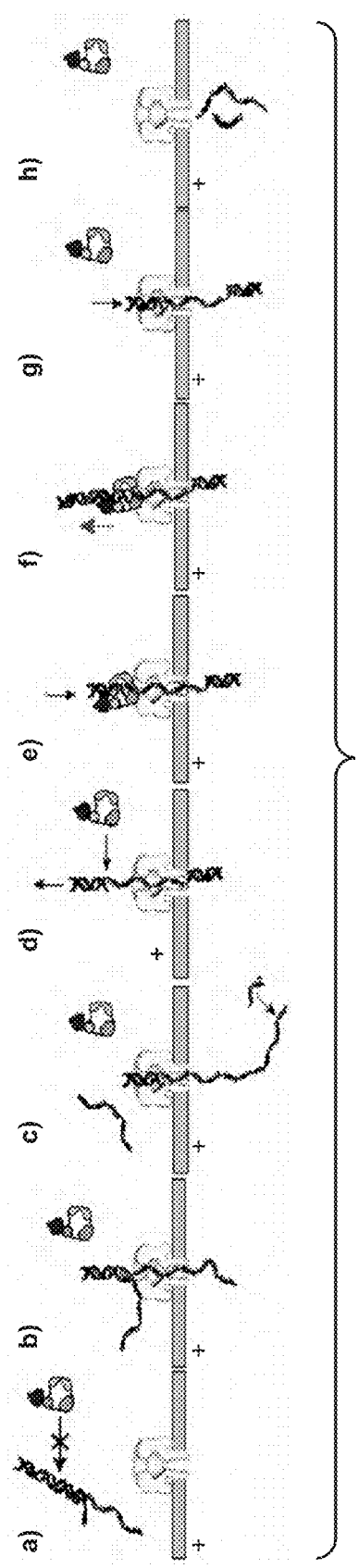

FIG. 25A  5'-(38)-ATATTXXXXCATTCATTCAGAGCTCACTATCGCATTCTCATGCAGGTCGTAGCC-3'

COMPOSITIONS, DEVICES, SYSTEMS, AND METHODS FOR USING A NANOPORE

CROSS-REFERENCE TO RELATED APPLICATIONS

The present application is a divisional application of and claims priority to pending U.S. patent application Ser. No. 12/459,059 filed on 26 Jun. 2009, which is a continuation-in-part of and claims priority to International Patent Application No. PCT/US2008/004467, filed 4 Apr. 2008, which, in turn, claimed priority to and benefits of the following: U.S. Provisional Patent Application Ser. No. 60/921,787 entitled "Methods To Limit Enzyme Activity To One Molecule Or Complex Using A Nanopore", filed 4 Apr. 2007; U.S. Provisional Patent Application Ser. No. 60/931,115 entitled "Methods For Sequencing Polynucleotides By Synthesis Using A Nanopore", filed 21 May 2007; U.S. Provisional Patent Application Ser. No. 60/962,530 entitled "Methods For Positioning Single Molecules At A Defined Site" filed 30 Jul. 2007; U.S. Provisional Patent Application Ser. 60/967,539 entitled "Methods For Manufacture of Very Large Scale Arrays of Independently Addressable Nanopores and Methods for Their Use" filed 4 Sep. 2007; and U.S. Provisional Patent Application Ser. No. 61/062,391 entitled "Feedback Control Of A Single Tethered Polynucleotide Suspended In A Nanopore To Repeatedly Probe Polynucleotide-Binding Proteins", filed 25 Jan. 2008; all of which are herein incorporated by reference in their entirety for all purposes.

STATEMENT OF GOVERNMENTAL SUPPORT

This invention was made partly using funds from the National Human Genome Research Institute grant numbers HG003703-01 and HG004035-01, and from the National Institute of General Medical Sciences grant number GM073617-01A1. The U.S. Federal Government has certain rights to this invention.

REFERENCE TO SEQUENCE LISTING, COMPUTER PROGRAM, OR COMPACT DISK

In accordance with "Legal Framework for EFS-Web," (6 Apr. 11) Applicants submit herewith a sequence listing as an ASCII text file. The text file will serve as both the paper copy required by 37 CFR 1.821(c) and the computer readable form (CRF) required by 37 CFR 1.821(e). The date of creation of the file was Feb. 26, 2014, and the size of the ASCII text file in bytes is 924. Applicants incorporate the contents of the sequence listing by reference in its entirety.

BACKGROUND OF THE INVENTION

1. Field of the Invention

The invention herein disclosed provides for devices and methods that can regulate when an individual polymer is acted upon by another compound, for example, a compound, such as a drug composition, a drug candidate, a lipid, an oligonucleotide, a polynucleotide, a peptide, an oligopeptide, a polypeptide, a protein and/or an enzyme. The invention is of particular use in the fields of molecular biology, structural biology, cell biology, molecular switches, molecular circuits, and molecular computational devices, and the manufacture thereof. The invention may be used for characterizing the sequence of a polynucleotide. The invention also relates to methods for identifying drug candidates that may be used to treat, alleviate, or prevent a clinical disorder or disease and to methods of using compositions so identified to treat a subject susceptible to, at risk of contracting or having a disease such as cancer, autoimmune diseases, cell cycle disorders, or other disorders.

2. Background

The invention relates to the field of compositions, methods, and apparatus for characterizing polynucleotides, other polymers, and drug candidates.

Determining the nucleotide sequence of DNA and RNA in a rapid manner is a major goal of researchers in biotechnology, especially for projects seeking to obtain the sequence of entire genomes of organisms. In addition, rapidly determining the sequence of a polynucleotide is important for identifying genetic mutations and polymorphisms in individuals and populations of individuals.

Nanopore sequencing is one method of rapidly determining the sequence of polynucleotide molecules. Nanopore sequencing is based on the property of physically sensing the individual nucleotides (or physical changes in the environment of the nucleotides (that is, for example, an electric current)) within an individual polynucleotide (for example, DNA and RNA) as it traverses or translocates through a nanopore aperture. In principle, the sequence of a polynucleotide can be determined from a single molecule. However, in practice, it is preferred that a polynucleotide sequence be determined from a statistical average of data obtained from multiple passages of the same molecule or the passage of multiple molecules having the same polynucleotide sequence. The use of membrane channels to characterize polynucleotides as the molecules pass through the small ion channels has been studied by Kasianowicz et al. (Proc. Natl. Acad. Sci. USA. 93:13770-13773, 1996, incorporate herein by reference) by using an electric field to force single stranded RNA and DNA molecules through a 1.5 nanometer diameter nanopore aperture (for example, an ion channel) in a lipid bilayer membrane. The diameter of the nanopore aperture permitted only a single strand of a polynucleotide to traverse the nanopore aperture at any given time. As the polynucleotide traversed the nanopore aperture, the polynucleotide partially blocked the nanopore aperture, resulting in a transient decrease of ionic current. Since the length of the decrease in current is directly proportional to the length of the polynucleotide, Kasianowicz et al. (1996) were able to determine experimentally lengths of polynucleotides by measuring changes in the ionic current.

Baldarelli et al. (U.S. Pat. No. 6,015,714) and Church et al. (U.S. Pat. No. 5,795,782) describe the use of nanopores to characterize polynucleotides including DNA and RNA molecules on a monomer by monomer basis. In particular, Baldarelli et al. characterized and sequenced the polynucleotides by passing a polynucleotide through the nanopore aperture. The nanopore aperture is imbedded in a structure or an interface, which separates two media. As the polynucleotide passes through the nanopore aperture, the polynucleotide alters an ionic current by blocking the nanopore aperture. As the individual nucleotides pass through the nanopore aperture, each base/nucleotide alters the ionic current in a manner that allows the identification of the nucleotide transiently blocking the nanopore aperture, thereby allowing one to characterize the nucleotide composition of the polynucleotide and perhaps determine the nucleotide sequence of the polynucleotide.

One disadvantage of previous nanopore analysis techniques is controlling the rate at which the target polynucleotide is analyzed. As described by Kasianowicz, et al. (1996), nanopore analysis is a useful method for performing length determinations of polynucleotides. However, the translocation rate is nucleotide composition dependent and can range between $10^5$ to $10^7$ nucleotides per second under the measurement conditions outlined by Kasianowicz et al. (1996). Therefore, the correlation between any given polynucleotide's length and its translocation time is not straightforward. It is also anticipated that a higher degree of resolution with regard to both the composition and spatial relationship between nucleotide units within a polynucleotide can be obtained if the translocation rate is substantially reduced.

There is currently a need to provide compositions and methods that can be used in characterization of polymers, including polynucleotides and polypeptides, characterization of drug candidates, as well as diagnosis and prognosis of diseases and disorders.

BRIEF DESCRIPTION OF THE INVENTION

The invention provides thin film nanopore devices and methods for using the same. The subject devices comprise cis and trans chambers connected by an electrical communication means. The cis and trans chambers are separated by a thin film comprising at least one pore or channel. In one embodiment, the chamber comprises a medium, wherein the medium is selected from the group consisting of an aqueous medium, a non-aqueous medium, an organic medium, and a gel medium. In one preferred embodiment, the thin film comprises a compound having a hydrophobic domain and a hydrophilic domain. In a more preferred embodiment, the thin film comprises a phospholipid. The devices further comprise a means for applying an electric field between the cis and the trans chambers. The pore or channel is shaped and sized having dimensions suitable for passaging a polymer. In one preferred embodiment the pore or channel accommodates a part but not all of the polymer. In one other preferred embodiment, the polymer is a polynucleotide. In an alternative preferred embodiment, the polymer is a polypeptide. Other polymers provided by the invention include polypeptides, phospholipids, polysaccharides, and polyketides.

In one embodiment, the thin film further comprises a compound having a binding affinity for the polymer. In one preferred embodiment the binding affinity ($K_a$) is at least $10^6$ l/mole. In a more preferred embodiment the $K_a$ is at least $10^8$ l/mole. In yet another embodiment the compound is adjacent to at least one pore. In an alternative embodiment, the compound is a soluble compound in the medium. In a more preferred embodiment the compound is a channel. In a yet more preferred embodiment the channel has biological activity. In a most preferred embodiment, the compound comprises the pore.

In one embodiment the compound comprises a molecule having biological activity. In a preferred embodiment, the molecule is, for example, but not limited to, a protein, a polypeptide, a peptide, a carbohydrate, a lipid, a nucleic acid, a glycopeptide, a glycolipid, a phospholipid, a steroid, a flavanoid, an isoprenoid, a catecholamine, a statin, and the like. In another embodiment the molecule is a polynucleotide-binding protein, such as a transcription factor, a nuclear hormone receptor, a heteronuclear protein, or a ribosome. The polynucleotide-binding protein may be used to identify drug candidates or drug targets that enhance or that may inhibit biding of the protein to the polynucleotide. In another embodiment the compound comprises enzyme activity. The enzyme activity can be, for example, but not limited to, enzyme activity of proteases, kinases, phosphatases, hydrolases, oxidoreductases, isomerases, transferases, methylases, acetylases, ligases, lyases, and the like. In a more preferred embodiment the enzyme activity can be enzyme activity of DNA polymerase, RNA polymerase, endonuclease, exonuclease, DNA ligase, DNase, uracil-DNA glycosidase, ribosomes, kinase, phosphatase, methylase, acetylase, or the like.

In another embodiment the pore is sized and shaped to allow passage of an activator, wherein the activator is selected from the group consisting of ATP, $NAD^+$, $NADP^+$, diacylglycerol, phosphatidylserine, eicosinoids, retinoic acid, calciferol, ascorbic acid, neuropeptides, enkephalins, endorphins, 4-aminobutyrate (GABA), 5-hydroxytryptamine (5-HT), catecholamines, acetyl CoA, S-adenosylmethionine, and any other biological activator.

In yet another embodiment the pore is sized and shaped to allow passage of a cofactor, wherein the cofactor is selected from the group consisting of $Mg^{2+}$, $Mn^{2+}$, $Ca^{2+}$, ATP, $NAD^+$, $NADP^+$, and any other biological cofactor.

In a preferred embodiment the pore or channel is a pore molecule or a channel molecule and comprises a biological molecule, or a synthetic modified molecule, or altered biological molecule, or a combination thereof. Such biological molecules are, for example, but not limited to, an ion channel, a nucleoside channel, a peptide channel, a sugar transporter, a synaptic channel, a transmembrane receptor, such as GPCRs and the like, a nuclear pore, synthetic variants, chimeric variants, or the like. In one preferred embodiment the biological molecule is α-hemolysin.

In an alternative, the compound comprises non-enzyme biological activity. The compound having non-enzyme biological activity can be, for example, but not limited to, proteins, peptides, antibodies, antigens, nucleic acids, peptide nucleic acids (PNAs), locked nucleic acids (LNAs), morpholinos, sugars, lipids, glycophosphoinositols, lipopolysaccharides or the like. The compound can have antigenic activity. The compound can have selective binding properties whereby the polymer binds to the compound under a particular controlled environmental condition, but not when the environmental conditions are changed. Such conditions can be, for example, but not limited to, change in $[H^+]$, change in environmental temperature, change in stringency, change in hydrophobicity, change in hydrophilicity, or the like.

In another embodiment, the invention provides a compound, wherein the compound further comprises a linker molecule, the linker molecule selected from the group consisting of a thiol group, a sulfide group, a phosphate group, a sulfate group, a cyano group, a piperidine group, an Fmoc group, and a Boc group.

In one embodiment the thin film comprises a plurality of pores. In one embodiment the device comprises a plurality of electrodes.

Polymers

In another embodiment, the invention provides a method for controlling binding of a compound, such as a drug composition, a drug candidate, a lipid, an oligonucleotide, a polynucleotide, a peptide, an oligopeptide, a polypeptide, a protein to a polymer, the method comprising: providing two separate, adjacent pools of a medium and an interface between the two pools, the interface having a channel so dimensioned as to allow sequential monomer-by-monomer passage from one pool to the other pool of only one polymer at a time; providing a compound having binding activity to a polymer; introducing the polymer into one of the two pools; introducing the enzyme into one of the two pools; applying a potential difference between the two pools, thereby creating a first polarity; reversing the potential difference a first time, thereby creating a second polarity; reversing the potential difference a second time to create the first polarity, thereby controlling the binding of the enzyme to the polymer. In a preferred embodiment, the medium is electrically conductive. In a more preferred embodiment, the medium is an aqueous solution. In another preferred embodiment, the method further comprises the steps of measuring the electrical current between the two pools; comparing the electrical current value ($I_1$) obtained at the first time the first polarity was induced with the electrical current value ($I_2$) obtained at the time the second time the first polarity was induced; and determining the difference between $I_1$ and $I_2$ thereby obtaining a difference value dI. In another preferred embodiment the method further comprises the steps of measuring the electrical current between the two pools; comparing the electrical current value ($I_1$) obtained at the first time the first polarity was induced with the electrical current value ($I_2$) obtained at a later time and determining the difference between $I_1$ and $I_2$ thereby obtaining a difference value dI. In one preferred embodiment the compound is a protein. In a more preferred embodiment the protein is an enzyme. In a more preferred embodiment, the enzyme is selected from the group consisting of proteases, kinases, phosphatases, hydrolases, oxidoreductases, isomerases, transferases, methylases, acetylases, ligases, and lyases. In another alternative embodiment, the method further comprises the steps of providing reagents that initiate enzyme activity; introducing the reagents to the pool comprising the polynucleotide complex; and incubating the pool at a suitable temperature. In a more preferred embodiment, the reagents are selected from the group consisting of an activator and a cofactor. In a yet more preferred embodiment, the activator is introduced into the pool prior to introducing the cofactor. In a yet still further more preferred embodiment, the activator is selected from the group consisting of ATP, $NAD^+$, $NADP^+$, diacylglycerol, phosphatidylserine, eicosinoids, retinoic acid, calciferol, ascorbic acid, neuropeptides, enkephalins, endorphins, 4-aminobutyrate (GABA), 5-hydroxytryptamine (5-HT), catecholamines, acetyl CoA, and S-adenosylmethionine. In another still more preferred embodiment, the cofactor is selected from the group consisting of $Mg^{2+}$, $Mn^{2+}$, $Ca^{2+}$, ATP, $NAD^+$, and $NADP^+$. In another more preferred embodiment, the polymer is selected from the group consisting of polynucleotides, polypeptides, phospholipids, polysaccharides, and polyketides. In one embodiment the enzyme is introduced into the same pool as the polymer. In an alternative embodiment, the enzyme is introduced into the opposite pool.

In another preferred embodiment the protein is a ligand receptor. In a more preferred embodiment the protein is a ligand receptor selected from the group consisting of nuclear receptors, such as, but not limited to, retinoic acid receptors (for example RAR, RXR) and the like, thyroid hormone receptors and the like, steroid hormone receptors and the like, peroxisome-proliferator activated receptors or the like, isoprenoid alcohol (for example, farnesol) receptors and the like, and orphan receptors and the like.

In another embodiment the ligand is selected from the group consisting of ligands of receptor proteins, such as, but not limited to, steroid hormones such as androgens, estrogens, progesterones, cortisols, and the like, arachidonic acid derivatives such as eicosenoids, retinoic acid and their derivatives, ethanolamides, thyroid hormones, isoprenoids, statins, small peptide hormones such as endorphins, GnRH, TSH, TRH, LH, or FSH, neurotransmitters such as chatecholamines, acetylcholine, 4-aminobutyrate, 5-hydroxytryptamine, glutamate, histamine, aspartate, antigens, domains involved in protein-protein interaction, such as PDZ domains, RDG domains, leucine zipper domains, insulin/ILR domains, MHC class I and MHC class II/TRC domains, EGF domains, plekstrin domains, domains involved in modified residue/protein interactions, such as SH2 and SH3 domains, and the like.

In another embodiment the invention provides a method for detecting a ligand that binds to a polymer, whereby the bound ligand to the protein-polymer holoplex is detected by relative proximity of the ligand-holoplex to the channel as disclosed herein. In an alternative embodiment the protein may be attached to another surface using a linker molecule or linker moiety, such as in a well surface, whereby presence of a blocking molecule that binds to the polymer prevents or inhibits binding of a ligand-protein complex to the polymer; removal of the blocking molecule allows binding of the ligand-protein complex to a target polynucleotide, and binding of the ligand to the protein and subsequence binding to the polymer occurs only in the absence of the blocking molecule. In a preferred embodiment the ligand is a drug target. In a more preferred embodiment the ligand is a drug target for use in the treatment of a clinical disorder or disease as disclosed below.

In other embodiments the ligand that binds to the polymer is not a protein but is a small molecule such as a co-factor or a nucleoside, such as ATP, $NAD^+$, and $NADP^+$. In other embodiments the ligand that binds to the polymer is a nucleotide, an oligonucleotide or polynucleotide such as a miRNA, an as RNA, poly(ADP)ribose, or a pseudogene product.

Polynucleotides

In another embodiment, the invention provides a method for controlling binding of compound, such as a drug composition, a drug candidate, a lipid, an oligonucleotide, a polynucleotide, a peptide, an oligopeptide, a polypeptide, a protein or an enzyme to a partially double-stranded polynucleotide complex, the method comprising: providing two separate, adjacent pools of a medium and an interface between the two pools, the interface having a channel so dimensioned as to allow sequential monomer-by-monomer passage from one pool to the other pool of only one polynucleotide at a time; providing a compound having binding activity to a partially double-stranded polynucleotide complex; providing a polynucleotide complex comprising a first polynucleotide and a second polynucleotide, wherein a portion of the polynucleotide complex is double-stranded, and wherein the first polynucleotide further comprises a moiety that is incompatible with the second polynucleotide; introducing the polynucleotide complex into one of the two pools; introducing the compound into one of the two pools; applying a potential difference between the two pools, thereby creating a first polarity; reversing the potential difference a first time, thereby creating a second polarity; reversing the potential difference a second time to create the first polarity, thereby controlling the binding of the compound to the partially double-stranded polynucleotide complex. In a preferred embodiment, the medium is electrically conductive. In a more preferred embodiment, the medium is an aqueous solution. In a preferred embodiment, the moiety is selected from the group consisting of acridine, a peptide nucleic acid, a 2'-O-methyl group, a fluorescent compound, DAPI, a derivatized nucleotide, and a nucleotide isomer. In another preferred embodiment, the method further comprises the steps of measuring the electrical current between the two pools; comparing the electrical current value obtained at the first time the first polarity was induced with the electrical current value obtained at the time the second time the first polarity was induced. In another preferred embodiment the method further comprises the steps of measuring the electrical current between the two pools; comparing the electrical current value obtained at the first time the first polarity was induced with the electrical current value obtained at a later time. In a preferred embodiment, the compound is a protein. In a more preferred embodiment the protein is an enzyme. In a most preferred embodiment, the enzyme is selected from the group consisting of DNA polymerase, RNA polymerase, endonuclease, exonuclease, DNA ligase, DNase, uracil-DNA glycosidase, kinase, phosphatase, methylase, and acetylase. In another alternative embodiment, the method further comprises the steps of providing at least one reagent that initiates enzyme activity; introducing the reagent to the pool comprising the polynucleotide complex; and incubating the pool at a suitable temperature. In a more preferred embodiment, the reagent is selected from the group consisting of a deoxyribonucleotide and a cofactor. In a yet more preferred embodiment, the deoxyribonucleotide is introduced into the pool prior to introducing the cofactor. In another still more preferred embodiment, the cofactor is selected from the group consisting of $Mg^{2+}$, $Mn^{2+}$, $Ca^{2+}$, ATP, $NAD^+$, and $NADP^+$. In one embodiment the enzyme is introduced into the same pool as the polynucleotide. In an alternative embodiment, the enzyme is introduced into the opposite pool.

In yet another alternative embodiment the protein is a ligand receptor. In a more preferred embodiment the protein is a ligand receptor selected from the group consisting of nuclear receptors, such as, but not limited to, retinoic acid receptors (for example RAR, RXR) and the like, thyroid hormone receptors and the like, steroid hormone receptors and the like, peroxisome-proliferator activated receptors or the like, isoprenoid alcohol (for example, farnesol) receptors and the like, and orphan receptors and the like. Other proteins, for example proteins that interact with DNA or RNA, for example, transcriptional regulators, transcriptional enhancers, or methylases or demthylases, are well known to those of skill in the art. Many such proteins are known by those of skill in the art to have a role in disease or disorders, such as cancer or inflammatory disorders.

In another alternative embodiment, the protein can be a ribosome or a ribosomal protein; the protein can be a nucleotide binding protein such as a heteronuclear ribonucleoprotein complex, a small nuclear ribonucleoparticle, a polynucleotide transport protein, such as proteins that export RNA from the nucleus; the protein can be a viral protein or a bacterial protein, or the like.

Polypeptides

In another embodiment, the invention provides a method for controlling binding of compound, such as a drug composition, a drug candidate, a lipid, an oligonucleotide, a polynucleotide, a peptide, an oligopeptide, a polypeptide, a protein or an enzyme to a polypeptide, the method comprising: providing two separate, adjacent pools of a medium and an interface between the two pools, the interface having a channel so dimensioned as to allow sequential monomer-by-monomer passage from one pool to the other pool of only one polypeptide at a time; providing compound having binding activity to a polypeptide; providing a polypeptide comprising a modifiable amino acid residue or a moiety; introducing the polypeptide into one of the two pools; introducing the compound into one of the two pools; applying a potential difference between the two pools, thereby creating a first polarity; reversing the potential difference a first time, thereby creating a second polarity; reversing the potential difference a second time to create the first polarity, thereby controlling the binding of the compound to the polypeptide. In a preferred embodiment, the medium is electrically conductive. In a more preferred embodiment, the medium is an aqueous solution. In a preferred embodiment, the moiety is selected from the group consisting of a peptide nucleic acid, a 2'-O-methyl group, a fluorescent compound, a derivatized amino acid, and a amino acid isomer. In another preferred embodiment, the method further comprises the steps of measuring the electrical current between the two pools; comparing the electrical current value obtained at the first time the first polarity was induced with the electrical current value obtained at the time the second time the first polarity was induced. In another preferred embodiment the method further comprises the steps of measuring the electrical current between the two pools; comparing the electrical current value obtained at the first time the first polarity was induced with the electrical current value obtained at a later time. In a preferred embodiment, the compound is a protein. In a more preferred embodiment the protein is an enzyme. In a most preferred embodiment, the enzyme is selected from the group consisting of, protease, kinase, phosphatase, hydrolase, oxidoreductase, isomerase, transferase, methylase, ligase, lyase, lipase, and acetylase. In another alternative embodiment, the method further comprises the steps of providing at least one reagent that initiates enzyme activity; introducing the reagent to the pool comprising the polynucleotide complex; and incubating the pool at a suitable temperature. In a more preferred embodiment, the reagent is selected from the group consisting of an activator and a cofactor. In a most preferred embodiment, the activator is selected from the group consisting of ATP, $NAD^+$, $NADP^+$, diacylglycerol, phosphatidylserine, acetyl CoA, and S-adenosylmethionine. In a yet more preferred embodiment, the activator is introduced into the pool prior to introducing the cofactor. In another still more preferred embodiment, the cofactor is selected from the group consisting of $Mg^{2+}$, $Mn^{2+}$, $Ca^{2+}$, ATP, $NAD^+$, and $NADP^+$. In one embodiment the enzyme is introduced into the same pool as the polypeptide. In an alternative embodiment, the enzyme is introduced into the opposite pool.

In yet another alternative embodiment the protein is a ligand receptor. In a more preferred embodiment the protein is a ligand receptor selected from the group consisting of nuclear receptors, such as, but not limited to, receptors for retinoic acid (for example, receptors such as, RAR and RXR) and the like, thyroid hormone (for example, T3 and T4) and the like, steroid hormones such as androgens, estrogens, progesterones, cortisols, and the like, peroxisome-proliferator activated receptors or the like, isoprenoid alcohols (for example, farnesol) receptors and the like, and orphan receptors and the like, ligands of receptor proteins, such as, but not limited to, arachidonic acid derivatives such as eicosenoids and their derivatives, ethanolamides, small peptide hormones such as endorphins, GnRH, TSH, TRH, LH, or FSH, neurotransmitters such as chatecholamines, acetylcholine, 4-aminobutyrate, 5-hydroxytryptamine, glutamate, histamine, aspartate, antigens, domains involved in protein-protein interaction, such as PDZ domains, RDG domains, leucine zipper domains, insulin/ILR domains, MHC class I and MHC class II/TRC domains, EGF domains, plekstrin domains, domains involved in modified residue/protein interactions, such as SH2 and SH3 domains, other transcription factors, other enhancer factors, and the like.

The invention herein disclosed provides for devices and methods that can regulate the rate at which an individual polymer in a mixture is acted upon by another compound, for example, an enzyme. The devices and methods are also used to determine the nucleotide base sequence of a polynucleotide The invention is of particular use in the fields of molecular biology, structural biology, cell biology, molecular switches, molecular circuits, and molecular computational devices, and the manufacture thereof.

In one alternative embodiment, the invention provides a method for controlling binding of compound, such as a drug composition, a drug candidate, a lipid, an oligonucleotide, a polynucleotide, a peptide, an oligopeptide, a polypeptide, a protein or an enzyme to a partially double-stranded polynucleotide complex and the method resulting in identifying the sequence of a polynucleotide, the method comprising the steps of: providing two separate adjacent pools comprising a medium, an interface between the two pools, the interface having a channel so dimensioned as to allow sequential monomer-by-monomer passage from the cis-side of the channel to the trans-side of the channel of only one polynucleotide strand at a time; providing a compound having binding activity to a partially double-stranded polynucleotide complex; providing at least one protected deoxyribonucleotide, the protection comprising using a protecting moiety; providing an annealing agent; providing a polynucleotide complex comprising a first polynucleotide and a second polynucleotide, wherein a portion of the polynucleotide complex is double-stranded and a portion is single-stranded; introducing the polynucleotide complex into one of the two pools; applying a potential difference between the two pools, thereby creating a first polarity, the first polarity causing the single stranded portion of the polynucleotide to transpose through the channel to the trans-side; introducing the compound and the protected deoxyribonucleotide into the same pool; introducing the annealing agent into the other pool; allowing the annealing agent to bind to the single-stranded polynucleotide; allowing the compound and the protected deoxyribonucleotide to bind to the polynucleotide; allowing the protected deoxyribonucleotide to be incorporated into the polynucleotide; reversing the potential difference a first time, thereby creating a second polarity; allowing the protected deoxyribonucleotide to release the protecting moiety and become deprotected; measuring the abundance of the protecting moiety; reversing the potential difference a second time to create the first polarity; repeating any one of the steps, thereby controlling the binding of the compound to the double-stranded polynucleotide complex and determining the sequence of the polynucleotide. In a preferred embodiment, the medium is electrically conductive. In a more preferred embodiment, the medium is an aqueous medium. In one preferred embodiment, the moiety is selected from the group consisting of acridine, a peptide nucleic acid, a 2'-O-methyl group, a fluorescent compound, DAPI, anthocyanins, green fluorescent protein (GFP), β-glucuronidase, luciferase, Cy3, Cy5, a derivatized nucleotide, and a nucleotide isomer. In another preferred embodiment, the enzyme is selected from the group consisting of DNA polymerase, RNA polymerase, endonuclease, exonuclease, DNA ligase, DNase, uracil-DNA glycosidase, kinase, phosphatase, methylase, and acetylase. In one alternative embodiment, the method further comprises the steps of measuring the electrical current between the two pools; comparing the electrical current value obtained at the first time the first polarity was induced with the electrical current value obtained at the time the second time the first polarity was induced. In another alternative embodiment, the method further comprises the steps of measuring the electrical current between the two pools; comparing the electrical current value obtained at the first time the first polarity was induced with the electrical current value obtained at a later time. In a preferred embodiment, the compound is a protein. In a more preferred embodiment the protein is an enzyme. In a yet further alternative embodiment, the method further comprises the steps of providing at least one reagent that initiates enzyme activity; introducing the reagent to the pool comprising the polynucleotide complex; and incubating the pool at a temperature sufficient to maintain enzyme activity. In a preferred embodiment, the reagent is a cofactor. In a more preferred embodiment, the cofactor is selected from the group consisting of $Mg^{2+}$, $Mn^{2+}$, $Ca^{2+}$, ATP, $NAD^+$, $NADP^+$, and S-adenosylmethionine. In another preferred embodiment, the protected deoxyribonucleotide comprises a deoxyribonucleotide selected from the group consisting of dATP, dGTP, dTTP, dCTP, and dUTP. In another more preferred embodiment, the reagent is selected from the group consisting of ddATP, ddGTP, ddTTP, ddCTP, and ddUTP. In a yet other preferred embodiment, the aqueous medium of at least one pool comprises an annealing agent. In a more preferred embodiment, the annealing agent selected from the group consisting of a complementary oligonucleotide and streptavidin.

The invention also provides a method for sensing the position of a molecule relative to a pore, the method comprising: providing two separate, adjacent pools of a medium and a structure between the two pools, the structure having an ion-permeable pore; providing a polyion; providing a molecule having binding activity to the polyion; introducing the polyion into one of the two pools; introducing the molecule into the same pool; applying a potential difference between the two pools, thereby creating a first polarity; measuring a first electrical current between the two pools, thereby sensing the position of a molecule relative to the pore. In a preferred embodiment, the molecule is a macromolecule, wherein the macromolecule selected from the group consisting of proteases, kinases, phosphatases, hydrolases, oxidoreductases, isomerases, transferases, methylases, acetylases, ligases, lyases, a transmembrane receptor, a receptor tyrosine kinase, a T-cell receptor, an MHC receptor, and a nuclear receptor. In another preferred embodiment the medium is electrically conductive. In a more preferred embodiment, the medium is an aqueous solution. In another preferred embodiment, the structure further comprises a compound, wherein the compound is selected from the group consisting of a thiol group, a sulfide group, a phosphate group, a sulfate group, a cyano group, a piperidine group, an Fmoc group, and a Boc group, silicon nitride, bifunctional alkyl sulfide, and gold. In another preferred embodiment, the polyion is selected from the group consisting of polynucleotides, polypeptides, phospholipids, polysaccharides, and polyketides. In alternative embodiment, the method further comprises the steps of reversing the potential difference a first time, thereby creating a second polarity; reversing the potential difference a second time to create the first polarity, measuring a second electrical current between the two pools, thereby further sensing the position of the molecule relative to the pore. In another alternative embodiment, the method further comprises the steps of measuring the electrical current between the two pools; comparing the electrical current value obtained at the first time the first polarity was induced with the electrical current value obtained at a later time. In a still further alternative embodiment, the method further comprises the steps of providing reagents that initiate enzyme activity; introducing the reagents to the pool comprising the polynucleotide complex; and incubating the pool at a suitable temperature.

In a more preferred embodiment, the reagents are selected from the group consisting of an activator and a cofactor. In another more preferred embodiment, the activator is introduced into the pool prior to introducing the cofactor. In a still more preferred embodiment, the activator is selected from the group consisting of ATP, $NAD^+$, $NADP^+$, diacylglycerol, phosphatidylserine, eicosinoids, glycosyl phosphatidyl inositols, glycophosphoinositols, lipopolysaccharides, retinoic acid, calciferol, ascorbic acid, neuropeptides, enkephalins, endorphins, 4-aminobutyrate (GABA), 5-hydroxytryptamine (5-HT), catecholamines, acetyl CoA, and S-adenosylmethionine. In another still more preferred embodiment, the cofactor is selected from the group consisting of $Mg^{2+}$, $Mn^{2+}$, $Ca^{2+}$, ATP, $NAD^+$, and $NADP^+$.

In a preferred embodiment the pore or channel comprises a biological molecule, or a synthetic modified or altered biological molecule. Such biological molecules are, for example, but not limited to, an ion channel, such as a-hemolysin, a nucleoside channel, a peptide channel, a sugar transporter, a synaptic channel, a transmembrane receptor, such as GPCRs, a receptor tyrosine kinase, and the like, a T-cell receptor, an MHC receptor, a nuclear receptor, such as a steroid hormone receptor, a nuclear pore, or the like.

In an alternative embodiment, the compound comprises non-enzyme biological activity. The compound having non-enzyme biological activity can be, for example, but not limited to, proteins, peptides, antibodies, antigens, nucleic acids, peptide nucleic acids (PNAs), locked nucleic acids (LNAs), morpholinos, sugars, lipids, glycosyl phosphatidyl inositols, glycophosphoinositols, lipopolysaccharides, or the like. The compound can have antigenic activity. The compound can have ribozyme activity. The compound can have selective binding properties whereby the polymer binds to the compound under a particular controlled environmental condition, but not when the environmental conditions are changed. Such conditions can be, for example, but not limited to, change in $[H^+]$, change in environmental temperature, change in stringency, change in hydrophobicity, change in hydrophilicity, change in hydrophilicity, or the like.

In one embodiment the macromolecule comprises enzyme activity. The enzyme activity can be, for example, but not limited to, enzyme activity of proteases, kinases, phosphatases, hydrolases, oxidoreductases, isomerases, transferases, methylases, acetylases, ligases, lyases, and the like. In a more preferred embodiment the enzyme activity can be enzyme activity of DNA polymerase, RNA polymerase, endonuclease, exonuclease, DNA ligase, DNase, uracil-DNA glycosidase, kinase, phosphatase, methylase, acetylase, glucose oxidase, or the like. In an alternative embodiment, the macromolecule can comprise more that one enzyme activity, for example, the enzyme activity of a cytochrome P450 enzyme. In another alternative embodiment, the macromolecule can comprise more than one type of enzyme activity, for example, mammalian fatty acid synthase. In another embodiment the macromolecule comprises ribozyme activity.

In an alternative embodiment, the macromolecule comprises non-enzyme biological activity. The macromolecule having non-enzyme biological activity can be, for example, but not limited to, proteins, peptides, antibodies, antigens, nucleic acids, peptide nucleic acids (PNAs), locked nucleic acids (LNAs), morpholinos, sugars, phospholipids, lipids, glycosyl phosphatidyl inositols, glycophosphoinositols, lipopolysaccharides, or the like. The macromolecule can have polynucleotide-binding activity and/or polypeptide biosynthesis activity, such as, but not limited to, a ribosome or a nucleosome. The macromolecule can have antigenic activity. The macromolecule can have selective binding properties whereby the polymer binds to the macromolecule under a particular controlled environmental condition, but not when the environmental conditions are changed. Such conditions can be, for example, but not limited to, change in $[H^+]$, change in environmental temperature, change in stringency, change in hydrophobicity, change in hydrophilicity, or the like.

In another embodiment, the invention provides a compound, wherein the compound further comprises a linker molecule, the linker molecule selected from the group consisting of a thiol group, a sulfide group, a phosphate group, a sulfate group, a cyano group, a piperidine group, an Fmoc group, and a Boc group. In another embodiment the compound is selected from the group consisting of a bifunctional alkyl sulfide and gold.

In one embodiment the thin film comprises a plurality of pores. In one embodiment the device comprises a plurality of electrodes.

The invention also provides a finite state machine that can be used to detect and control binding of a molecule to a polymer. In one embodiment, the molecule is a protein. In a preferred embodiment, the protein is an enzyme. In one embodiment, the finite state machine can detect a polymer compound having a structural element that inhibits transposition of the polymer compound through a nanopore. In one preferred embodiment, the finite state machine can detect a polymer compound comprising a DNA hairpin structure in a nanopore, eject the compound comprising a DNA hairpin or DNA duplex structure from a nanopore after it has been detected but prior to unzipping the hairpin or DNA duplex structure. In an alternative embodiment the polymer compound comprises a derivatized nucleic acid. In yet another alternative embodiment, the polymer compound comprises a peptide nucleic acid.

In one embodiment the finite state machine can control binding of a molecule to a polymer at a rate of between about 5 Hz and 2000 Hz. The finite state machine can control binding of a molecule to a polymer at, for example, about 5 Hz, at about 10 Hz, at about 15 Hz, at about 20 Hz, at about 25 Hz, at about 30 Hz, at about 35 Hz, at about 40 Hz, at about 45 Hz, at about 50 Hz, at about 55 Hz, at about 60 Hz, at about 65 Hz, at about 70 Hz, at about 75 Hz, at about 80 Hz, at about 85 Hz, at about 90 Hz, at about 95 Hz, at about 100 Hz, at about 110 Hz, at about 120 Hz, at about 125 Hz, at about 130 Hz, at about 140 Hz, at about 150 Hz, at about 160 Hz, at about 170 Hz, at about 175 Hz, at about 180 Hz, at about 190 Hz, at about 200 Hz, at about 250 Hz, at about 300 Hz, at about 350 Hz, at about 400 Hz, at about 450 Hz, at about 500 Hz, at about 550 Hz, at about 600 Hz, at about 700 Hz, at about 750 Hz, at about 800 Hz, at about 850 Hz, at about 900 Hz, at about 950 Hz, at about 1000 Hz, at about 1125 Hz, at about 1150 Hz, at about 1175 Hz, at about 1200 Hz, at about 1250 Hz, at about 1300 Hz, at about 1350 Hz, at about 1400 Hz, at about 1450 Hz, at about 1500 Hz, at about 1550 Hz, at about 1600 Hz, at about 1700 Hz, at about 1750 Hz, at about 1800 Hz, at about 1850 Hz, at about 1900 Hz, at about 950 Hz, and at about 2000 Hz. In a preferred embodiment, the finite state machine can control binding of a molecule to a polymer at a rate of between about 25 Hz and about 250 Hz. In a more preferred embodiment the finite state machine can control binding of a molecule to a polymer at a rate of between about 45 Hz and about 120 Hz. In a most preferred embodiment the finite state machine can control binding of a molecule to a polymer at a rate of about 50 Hz.

The invention can be used to determine the nucleotide sequence of a polynucleotide. The invention can also be used to determine the relative affinity of an enzyme for binding a polynucleotide, thereby using the invention to identify novel enzyme compounds that bind to polynucleotides.

In one embodiment the compound comprises enzyme activity. The enzyme activity can be, for example, but not limited to, enzyme activity of proteases, kinases, phosphatases, hydrolases, oxidoreductases, isomerases, transferases, methylases, acetylases, ligases, lyases, and the like. In a more preferred embodiment the enzyme activity can be enzyme activity of DNA polymerase, RNA polymerase, endonuclease, exonuclease, DNA ligase, DNase, uracil-DNA glycosidase, kinase, phosphatase, methylase, acetylase, or the like.

In another embodiment the pore or channel is sized and shaped to allow passage of an activator, wherein the activator is selected from the group consisting of ATP, $NAD^+$, $NADP^+$, and any other biological activator.

In yet another embodiment the pore or channel is sized and shaped to allow passage of a cofactor, wherein the cofactor is selected from the group consisting of $Mg^{2+}$, $Mn^{2+}$, $Ca^{2+}$, ATP, $NAD^+$, $NADP^+$, and any other biological cofactor.

In a preferred embodiment the pore or channel comprises a biological molecule, or a synthetic modified or altered biological molecule. Such biological molecules are, for example, but not limited to, an ion channel, a nucleoside channel, a peptide channel, a sugar transporter, a synaptic channel, a transmembrane receptor, such as GPCRs and the like, a nuclear pore, or the like. In one preferred embodiment the biological molecule is α-hemolysin.

In an alternative, the compound comprises non-enzyme biological activity. The compound having non-enzyme biological activity can be, for example, but not limited to, proteins, peptides, antibodies, antigens, nucleic acids, peptide nucleic acids (PNAs), locked nucleic acids (LNAs), morpholinos, sugars, lipids, glycophosphoinositols, lipopolysaccharides, or the like. The compound can have antigenic activity. The compound can have selective binding properties whereby the polymer binds to the compound under a particular controlled environmental condition, but not when the environmental conditions are changed. Such conditions can be, for example, but not limited to, change in $[H^+]$, change in environmental temperature, change in stringency, change in hydrophobicity, change in hydrophilicity, or the like.

In yet another embodiment, the invention provides a method for controlling binding of compound, such as a drug composition, a drug candidate, a lipid, an oligonucleotide, a polynucleotide, a peptide, an oligopeptide, a polypeptide, a protein or an enzyme to a polynucleotide using voltage feedback control, the method resulting in repeated capture of and dissociation of the compound by the polynucleotide, the method comprising the steps of: providing two separate adjacent compartments comprising a medium, an interface between the two compartments, the interface having a channel so dimensioned as to allow sequential monomer-by-monomer passage from the cis-side of the channel to the trans-side of the channel of only one polynucleotide strand at a time; providing a compound having binding activity for a polynucleotide; providing a protected ribonucleotide; providing a polynucleotide-binding compound; providing a polynucleotide complex, wherein a portion of the polynucleotide complex is double-stranded and a portion is single-stranded; introducing the polynucleotide complex into one of the two chambers; applying a potential difference between the two chambers, thereby creating a first polarity, the first polarity causing the single stranded portion of the polynucleotide to transpose through the channel to the trans-side; introducing the protected ribonucleotide into the same chamber; introducing the compound into the same chamber; allowing the compound to bind to the polynucleotide; allowing the protected ribonucleotide to bind to the polynucleotide; measuring the electrical current through the channel thereby detecting the binding of the compound and the protected ribonucleotide to the polynucleotide; introducing the polynucleotide-binding compound into the other of the two chambers; decreasing the potential difference a first time, thereby creating a second polarity; allowing the polynucleotide-binding compound to bind to the single-stranded polynucleotide; reversing the potential difference, thereby creating a third polarity; reversing the potential difference a second time; measuring the electrical current through the channel, thereby detecting a polynucleotide alone or a polynucleotide bound to the compound and the protected ribonucleotide; repeating any one of the steps, thereby controlling the binding of the compound to the polynucleotide. In a preferred embodiment, the method further comprises the steps of measuring the electrical current between the two chambers; comparing the electrical current value obtained at the first time the first polarity was induced with the electrical current value obtained at the time the second time the first polarity was induced. In another preferred embodiment, the method further comprises the steps of measuring the electrical current between the two chambers; comparing the electrical current value obtained at the first time the first polarity was induced with the electrical current value obtained at a later time. In a preferred embodiment, the polynucleotide-binding compound is selected from the group consisting of an oligonucleotide complementary to the polynucleotide, a peptide nucleic acid, a locked nucleic acid, a derivatized nucleotide, and a nucleotide isomer. In another preferred embodiment, the compound is a protein. In a more preferred embodiment the protein is an enzyme. In most preferred embodiment, the enzyme is selected from the group consisting of DNA polymerase, RNA polymerase, endonuclease, exonuclease, DNA ligase, DNase, uracil-DNA glycosidase, kinase, phosphatase, methylase, and acetylase. In another preferred embodiment the medium is electrically conductive. In another preferred embodiment the medium is an aqueous medium. In another preferred embodiment the protected ribonucleotide comprises a deoxyribonucleotide selected from the group consisting of dATP, dGTP, TTP, dCTP, UTP, and dUTP. In another embodiment the protected ribonucleotide is selected from the group consisting of ATP, GTP, TTP, CTP, and tRNA.

The method may further comprise the steps of providing at least one reagent that initiates enzyme activity; introducing the reagent to the chamber comprising the polynucleotide complex; and incubating the chamber at a temperature sufficient to maintain enzyme activity. In a preferred embodiment the reagent is a cofactor. In a more preferred embodiment, the cofactor is selected from the group consisting of $Mg^{2+}$, $Mn^{2+}$, $Ca^{2+}$, ATP, $NAD^+$, $NADP^+$, and S-adenosylmethionine. In another preferred embodiment, the reagent is selected from the group consisting of ddATP, ddGTP, ddTTP, ddCTP, and ddUTP.

In another embodiment of the invention, the invention provides a method for controlling binding of compound, such as a drug composition, a drug candidate, a lipid, an oligonucleotide, a polynucleotide, a peptide, an oligopeptide, a polypeptide, a protein or an enzyme to a polynucleotide using voltage feedback control, the method resulting in identifying the sequence of a polynucleotide, the method comprising the steps of: providing two separate adjacent chambers comprising a medium, an interface between the two chambers, the interface having a channel so dimensioned as to allow sequential monomer-by-monomer passage from the cis-side of the channel to the trans-side of the channel of only one polynucleotide strand at a time; providing a compound having binding activity for a polynucleotide; providing a protected deoxyribonucleotide; providing a polynucleotide-binding compound; providing a polynucleotide complex, wherein a portion of the polynucleotide complex is double-stranded and a portion is single-stranded; introducing the polynucleotide complex into one of the two chambers; applying a potential difference between the two chambers, thereby creating a first polarity, the first polarity causing the single stranded portion of the polynucleotide to transpose through the channel to the trans-side; introducing the protected deoxyribonucleotide into the same chamber; introducing the compound into the same chamber; allowing the compound to bind to the polynucleotide; allowing the protected deoxyribonucleotide to bind to the polynucleotide; measuring the electrical current through the channel thereby detecting the binding of the compound and the protected deoxyribonucleotide to the polynucleotide; introducing the polynucleotide-binding compound into the other of the two chambers; decreasing the potential difference a first time, thereby creating a second polarity; allowing the polynucleotide-binding compound to bind to the single-stranded polynucleotide; reversing the potential difference, thereby creating a third polarity; reversing the potential difference a second time; measuring the electrical current through the channel, thereby detecting a polynucleotide alone or a polynucleotide bound to the compound and the protected deoxyribonucleotide; repeating any one of the steps, thereby controlling the binding of the compound to the polynucleotide. In a preferred embodiment, the method further comprises the steps of measuring the electrical current between the two chambers; comparing the electrical current value obtained at the first time the first polarity was induced with the electrical current value obtained at the time the second time the first polarity was induced. In another preferred embodiment, the method further comprises the steps of measuring the electrical current between the two chambers; comparing the electrical current value obtained at the first time the first polarity was induced with the electrical current value obtained at a later time. In a preferred embodiment, the polynucleotide-binding compound is selected from the group consisting of an oligonucleotide complementary to the polynucleotide, a peptide nucleic acid, a locked nucleic acid, a derivatized nucleotide, and a nucleotide isomer. In another preferred embodiment, the compound is a protein. In a more preferred embodiment the protein is an enzyme. In a most preferred embodiment, the enzyme is selected from the group consisting of DNA polymerase, RNA polymerase, endonuclease, exonuclease, DNA ligase, DNase, uracil-DNA glycosidase, kinase, phosphatase, methylase, and acetylase. In another preferred embodiment the medium is electrically conductive. In another preferred embodiment the medium is an aqueous medium. In another preferred embodiment the protected deoxyribonucleotide comprises a deoxyribonucleotide selected from the group consisting of dATP, dGTP, TTP, dCTP, UTP, and dUTP. The method may further comprise the steps of providing at least one reagent that initiates enzyme activity; introducing the reagent to the chamber comprising the polynucleotide complex; and incubating the chamber at a temperature sufficient to maintain enzyme activity. In a preferred embodiment the reagent is a cofactor. In a more preferred embodiment, the cofactor is selected from the group consisting of $Mg^{2+}$, $Mn^{2+}$, $Ca^{2+}$, ATP, $NAD^+$, $NADP^+$, and S-adenosylmethionine. In another preferred embodiment, the reagent is selected from the group consisting of ddATP, ddGTP, ddTTP, ddCTP, and ddUTP.

The invention also provides a method for controlling movement of a polynucleotide using voltage feedback control, the method resulting in identifying the sequence of a polynucleotide, the method comprising the steps of: providing two separate adjacent chambers comprising a medium, an interface between the two chambers, the interface comprising a material having at least one channel therethrough and wherein one chamber is on the cis-side of the interface and the other chamber is on the trans-side of the interface, the channel so dimensioned as to allow sequential monomer-by-monomer passage from the cis-side of the channel to the trans-side of the channel of only one polynucleotide strand at a time; providing an enzyme having binding activity for a polynucleotide; providing a blocking oligomer; providing a polynucleotide complex, wherein a portion of the polynucleotide complex is double-stranded and a portion is single-stranded; providing a complimentary oligomer, wherein the complimentary oligomer is complementary to a portion of the single stranded polynucleotide; providing a substrate; introducing the polynucleotide complex into one of the two chambers; introducing the blocking oligomer into the same chamber; allowing the blocking oligomer to bind to the polynucleotide complex; introducing the enzyme into the same chamber; introducing the complementary oligomer into the other chamber; applying a potential difference between the two chambers, thereby creating a first polarity, the first polarity causing the single stranded portion of the polynucleotide to transpose through the channel to the trans-side thereby stripping the blocking oligomer from the polynucleotide complex; measuring the electrical current through the channel thereby detecting the polynucleotide; decreasing the potential difference a first time, thereby creating a second polarity; allowing the complementary oligomer to bind to the single-stranded polynucleotide; reversing the potential difference, thereby creating a third polarity; providing conditions to allow the enzyme to bind to the polynucleotide complex; providing conditions to allow the enzyme to incorporate substrate into the polynucleotide, thereby increasing length of the double-stranded portion; reversing the potential difference a second time; measuring the electrical current through the channel, thereby detecting a polynucleotide having incorporated substrate or a polynucleotide bound to the enzyme; repeating any one of the steps, thereby controlling the synthesis of the polynucleotide. In one preferred embodiment there are a plurality of channels. In another preferred embodiment the blocking oligomer is selected from the group consisting of an oligonucleotide having partial complementarity to a portion of the polynucleotide complex. In a more preferred embodiment the oligonucleotide having partial complementarity to a portion of the polynucleotide complex further comprises a duplex structure at one end of the oligonucleotide and a blocking moiety at the other end of the oligonucleotide. In another more preferred embodiment the oligonucleotide having partial complementarity to a portion of the polynucleotide complex further comprises a hairpin loop structure at one end of the oligonucleotide. In an alternative embodiment the blocking moiety is selected from the group consisting of acridine, a peptide nucleic acid, a 2'-O-methyl group, a fluorescent compound, DAPI, an anthocyanin, green fluorescent protein (GFP), β-glucuronidase, luciferase, Cy3, Cy5, a derivatized nucleotide, and a nucleotide isomer. In another alternative embodiment the blocking moiety blocks the binding of the compound, protein, and/or enzyme to the polynucleotide complex. In yet another alternative embodiment the blocking moiety blocks the biological activity of the compound, protein, and/or enzyme upon the polynucleotide complex. In still another alternative embodiment the blocking moiety blocks the strand displacement within the polynucleotide complex. In still yet another alternative embodiment the blocking moiety blocks replication and/or extension of the strand within the polynucleotide complex. In another embodiment the complementary oligomer is selected from the group consisting of an oligonucleotide complementary to the polynucleotide, a peptide nucleic acid, a locked nucleic acid, a derivatized nucleotide, a nucleotide isomer, and a DNA aptamer. In a preferred embodiment the enzyme is selected from the group consisting of DNA polymerase, RNA polymerase, endonuclease, exonuclease, DNA ligase, DNase, uracil-DNA glycosidase, topoisomerase, telomerase, DNA-repair enzyme; DNA-handling enzyme, helicase, primase, gyrase, kinase, phosphatase, methylase, acetylase, histone, transcription factor, and ribosome. In an alternative embodiment the step of allowing the blocking oligomer to bind to the polynucleotide complex is performed prior to introducing the polynucleotide complex and the blocking oligomer into the same chamber, and is followed by a step of introducing the polynucleotide complex and the blocking oligomer into the chamber. In another embodiment the method further comprises the steps of providing at least one reagent that initiates enzyme activity; introducing the reagent to the chamber comprising the polynucleotide complex; and incubating the chamber at a temperature sufficient to maintain enzyme activity. In a preferred embodiment the reagent is a cofactor. In a more preferred embodiment the cofactor is selected from the group consisting of $Mg^{2+}$, $Mn^{2+}$, $Ca^{2+}$, ATP, $NAD^+$, $NADP^+$, and S-adenosylmethionine. In a preferred embodiment the medium is electrically conductive. In another preferred embodiment the medium is an aqueous medium. In a preferred embodiment the substrate comprises a deoxyribonucleotide selected from the group consisting of dATP, dGTP, TTP, dCTP, UTP, and dUTP. In another embodiment the substrate comprises a ribonucleotide selected from the group consisting of ATP, GTP, TTP, CTP, and tRNA.

In a preferred embodiment the method controls the synthesis of a polynucleotide, the method resulting in identifying the sequence of a polynucleotide.

The invention also provides a polynucleotide sequencing system comprising (a) a structure comprising an ion-permeable passage connecting a first chamber and a second chamber, wherein a polynucleotide to be sequenced is placed with a blocking oligomer in the first chamber; (b) an enzyme having a binding affinity for a polynucleotide of at least $10^6$ $M^{-1} \cdot s^{-1}$ (c) a electronic power source for creating a potential difference between the two chambers; (d) a detection system operative to detect a property of a the polynucleotide moving relative to the ion-permeable passage. In one embodiment the structure further comprises a lipid bilayer. In another embodiment the blocking oligomer binds to the polynucleotide to be sequenced under stringent conditions. In a yet further embodiment the enzyme is selected from the group consisting of DNA polymerase, RNA polymerase, endonuclease, exonuclease, DNA ligase, DNase, uracil-DNA glycosidase, topoisomerase, telomerase, DNA-repair enzyme; DNA-handling enzyme, helicase, primase, gyrase, kinase, phosphatase, methylase, acetylase, histone, transcription factor, and ribosome. In a further embodiment the property of the polynucleotide is that of base identity at the 3' end of the double-stranded portion of the polynucleotide.

The invention also provides a blocking oligomer, wherein the blocking oligomer comprises a single stranded oligonucleotide, the single stranded oligonucleotide comprising a duplex structure at one end of the oligonucleotide and a blocking moiety at the other end of the oligonucleotide. In one embodiment a portion of the blocking oligomer further comprises a non-oligonucleotide composition wherein the non-oligonucleotide composition is selected from the group consisting of a polymer, a monomer, a dimer, a multimer, an acid, a base, an organic compound, and an inorganic compound. In one preferred embodiment, the non-oligonucleotide composition permits efficient removal of the blocking oligomer from a polynucleotide to which a portion of the blocking oligonucletide is bound or to which it is hybridized. In another embodiment the blocking moiety is selected from the group consisting of acridine, a peptide nucleic acid, a 2'-O-methyl group, a fluorescent compound, DAPI, an anthocyanin, green fluorescent protein (GFP), β-glucuronidase, luciferase, Cy3, Cy5, a derivatized nucleotide, and a nucleotide isomer. In another embodiment the blocking oligomer binds to a polynucleotide to be sequenced under stringent conditions. In a preferred embodiment the blocking oligomer comprises between about 5 and 30 nucleotides. In a more preferred embodiment the blocking oligomer comprises between about 15 and 25 nucleotides.

In one embodiment the thin film comprises a plurality of pores. In one embodiment the device comprises a plurality of electrodes.

BRIEF DESCRIPTION OF THE DRAWINGS

FIG. 17 illustrates repeated KF binding events using a single polynucleotide oligomer.

FIG. 18 illustrates an exemplary embodiment of the invention using a blocking molecule that prevents binding of a polynucleotide by a DNA-binding molecule. A strategy is shown for restricting DNA synthesis to individual DNA substrate molecules captured in a nanopore using blocking oligomers.

DETAILED DESCRIPTION OF THE INVENTION

Figure 1:
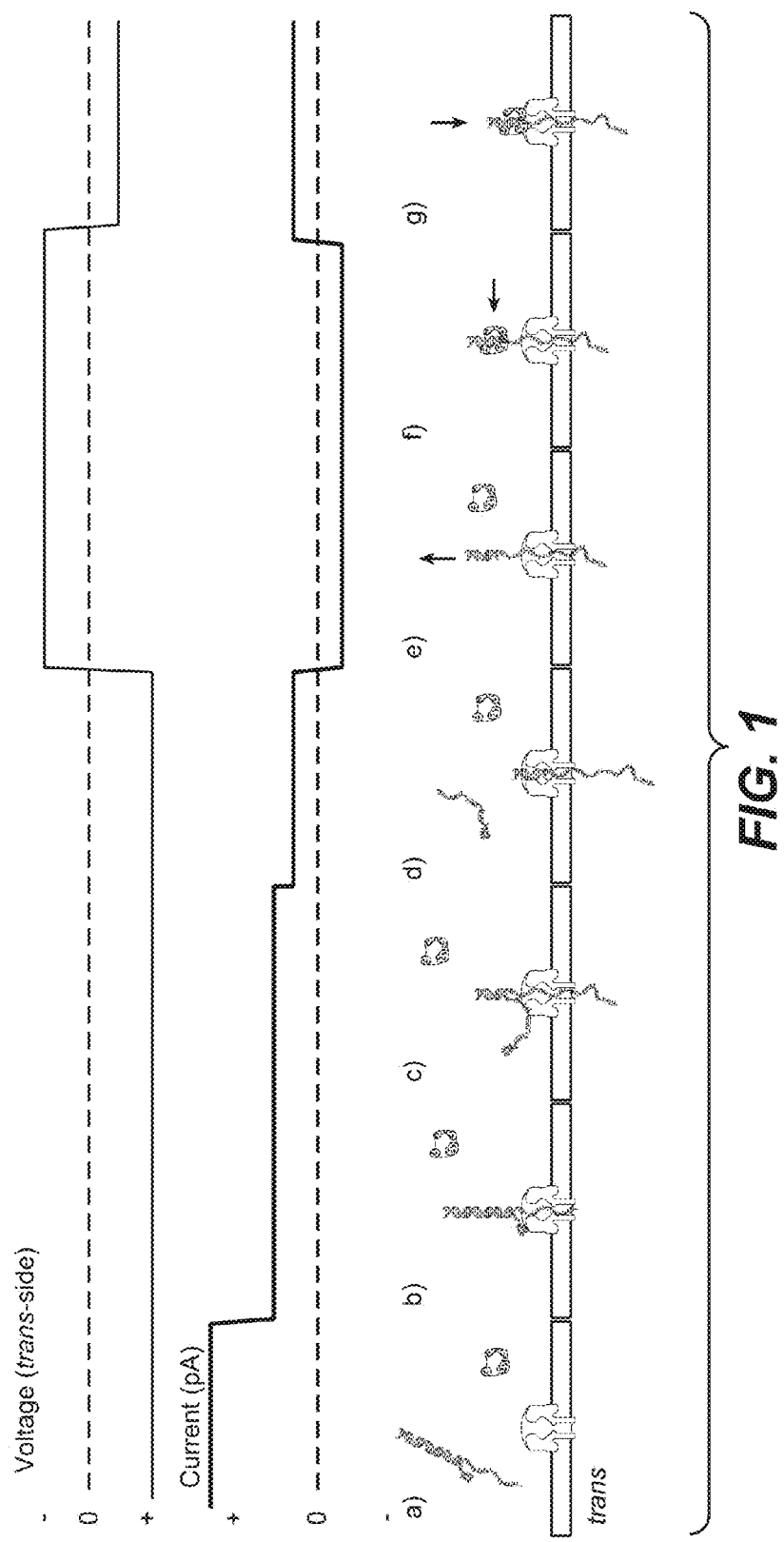
FIG. 1 illustrates an embodiment of the invention whereby enzyme binding to a polynucleotide is prevented by a blocking oligomer.

The embodiments disclosed in this document are illustrative and exemplary and are not meant to limit the invention. Other embodiments can be utilized and structural changes can be made without departing from the scope of the claims of the present invention.

The invention provides a method for sequencing a polynucleotide without the need for reversible or irreversible incorporation of a terminator nucleotide into the replicated strand. The invention also provides for specific activation of nucleotide-binding enzymes and/or proteins at a nanopore. In particular the invention provides for a feedback control of these reactions. The invention may also be used to identify drug candidates and/or drug targets.

As used herein and in the appended claims, the singular forms "a," "an," and "the" include plural reference unless the context clearly dictates otherwise. Thus, for example, a reference to "a nanopore" includes a plurality of such nanopores, and a reference to "a signal" is a reference to one or more signals and equivalents thereof, and so forth.

By "polynucleotide" is meant DNA or RNA, including any naturally occurring, synthetic, or modified nucleotide. Nucleotides include, but are not limited to, ATP, dATP, CTP, dCTP, GTP, dGTP, UTP, TTP, dUTP, 5-methyl-CTP, 5-methyl-dCTP, ITP, dITP, 2-amino-adenosine-TP, 2-amino-deoxyadenosine-TP, 2-thiothymidine triphosphate, pyrrolopyrimidine triphosphate, 2-thiocytidine as well as the alpha-thiotriphosphates for all of the above, and 2'-O-methyl-ribonucleotide triphosphates for all the above bases. Modified bases include, but are not limited to, 5-Br-UTP, 5-Br-dUTP, 5-F-UTP, 5-F-dUTP, 5-propynyl dCTP, and 5-propynyl-dUTP.

By "transport property" is meant a property measurable during polymer movement with respect to a nanopore. The transport property may be, for example, a function of the solvent, the polymer, a label on the polymer, other solutes (for example, ions), or an interaction between the nanopore and the solvent or polymer.

The term "ligand" means any composition having a binding affinity for another molecule and whereby binding of the ligand to the other molecule results in an increase or, alternatively, a decrease, in biological activity of the other molecule. Such other molecules may also be termed "ligand receptor".

A "hairpin structure" is defined as an oligonucleotide having a nucleotide sequence that is about 6 to about 100 nucleotides in length, the first half of which nucleotide sequence is at least partially complementary to the second part thereof, thereby causing the polynucleotide to fold onto itself, forming a secondary hairpin structure.

A "hairpin shaped precursor" is defined as a hairpin structure that is processed by a Microprocessor complex and then by a Dicer enzyme complex, yielding an oligonucleotide that is about 16 to about 24 nucleotides in length.

"Identity" or "similarity" refers to sequence similarity between two polynucleotide sequences or between two polypeptide sequences, with identity being a more strict comparison. The phrases "percent identity" and "% identity" refer to the percentage of sequence similarity found in a comparison of two or more polynucleotide sequences or two or more polypeptide sequences. "Sequence similarity" refers to the percent similarity in base pair sequence (as determined by any suitable method) between two or more polynucleotide sequences. Two or more sequences can be anywhere from 0-100% similar, or any integer value there between. Identity or similarity can be determined by comparing a position in each sequence that may be aligned for purposes of comparison. When a position in the compared sequence is occupied by the same nucleotide base or amino acid, then the molecules are identical at that position. A degree of similarity or identity between polynucleotide sequences is a function of the number of identical or matching nucleotides at positions shared by the polynucleotide sequences. A degree of identity of polypeptide sequences is a function of the number of identical amino acids at positions shared by the polypeptide sequences. A degree of homology or similarity of polypeptide sequences is a function of the number of amino acids at positions shared by the polypeptide sequences.

The term "incompatible" refers to the chemical property of a molecule whereby two molecules or portions thereof cannot interact with one another, physically, chemically, or both. For example, a portion of a polymer comprising nucleotides can be incompatible with a portion of a polymer comprising nucleotides and another chemical moiety, such as for example, acridine, a peptide nucleic acid, a 2'-O-methyl group, a fluorescent compound, DAPI, a derivatized nucleotide, a nucleotide isomer, or the like. In another example, a portion of a polymer comprising amino acid residues can be incompatible with a portion of a polymer comprising amino acid residues and another chemical moiety, such as, for example, a sulfate group, a phosphate group, an acetyl group, a cyano group, a piperidine group, a fluorescent group, a sialic acid group, a mannose group, or the like.

"Alignment" refers to a number of DNA or amino acid sequences aligned by lengthwise comparison so that components in common (such as nucleotide bases or amino acid residues) may be visually and readily identified. The fraction or percentage of components in common is related to the homology or identity between the sequences. Alignments may be used to identify conserved domains and relatedness within these domains. An alignment may suitably be determined by means of computer programs known in the art, such as MACVECTOR software (1999) (Accelrys, Inc., San Diego, Calif.).

The terms "highly stringent" or "highly stringent condition" refer to conditions that permit hybridization of DNA strands whose sequences are highly complementary, wherein these same conditions exclude hybridization of significantly mismatched DNAs. Polynucleotide sequences capable of hybridizing under stringent conditions with the polynucleotides of the present invention may be, for example, variants of the disclosed polynucleotide sequences, including allelic or splice variants, or sequences that encode orthologs or paralogs of presently disclosed polypeptides. Polynucleotide hybridization methods are disclosed in detail by Kashima et al. (1985) Nature 313: 402-404, and Sambrook et al. (1989) Molecular Cloning: A Laboratory Manual, 2nd Ed., Cold Spring Harbor Laboratory, Cold Spring Harbor, N.Y. ("Sambrook"); and by Haymes et al., "Nucleic Acid Hybridization: A Practical Approach", IRL Press, Washington, D.C. (1985), which references are incorporated herein by reference.

In general, stringency is determined by the incubation temperature, ionic strength of the solution, and concentration of denaturing agents (for example, formamide) used in a hybridization and washing procedure (for a more detailed description of establishing and determining stringency, see below). The degree to which two nucleic acids hybridize under various conditions of stringency is correlated with the extent of their similarity. Thus, similar polynucleotide sequences from a variety of sources, such as within an organism's genome (as in the case of paralogs) or from another organism (as in the case of orthologs) that may perform similar functions can be isolated on the basis of their ability to hybridize with known peptide-encoding sequences. Numerous variations are possible in the conditions and means by which polynucleotide hybridization can be performed to isolate sequences having similarity to sequences known in the art and are not limited to those explicitly disclosed herein. Such an approach may be used to isolate polynucleotide sequences having various degrees of similarity with disclosed sequences, such as, for example, sequences having 60% identity, or more preferably greater than about 70% identity, most preferably 72% or greater identity with disclosed sequences.

Devices that can be used to carry out the methods of the instant invention are described in for example, U.S. Pat. No. 5,795,782, U.S. Pat. No. 6,015,714, U.S. Pat. No. 6,267,872, U.S. Pat. No. 6,362,002, U.S. Pat. No. 6,746,594, U.S. Pat. No. 6,428,959, U.S. Pat. No. 6,617,113, U.S. Pat. No. 7,189,503, and in copending patent application U.S. Ser. No. 12/080,684, filed 4 Apr. 2008 and PCT/US08/00467, filed 4 Apr. 2008, each of which is hereby incorporated by reference in their entirety. The invention is best understood by the examples and methods disclosed herein.

It is now understood that a means to control the time at which enzymatic activity begins for an individual polymer in a mixture would be an advantage. That is, absent such a control, initiation of enzyme activity (for example by addition of $Mg^{2+}$ cofactor to a bath containing enzyme and DNA) would begin at once and that enzyme-polynucleotide complexes would necessarily be at many points along the target strands when captured by the nanopore in a time series. At least five methods can be used to overcome these potential multiple interactions:
a) Microfluidics.

A factor for inducing enzyme activity may be added only after an enzyme-polynucleotide complex is captured by the pore. After that polynucleotide is processed, the bath can be flushed and a new population of polynucleotide targets added absent the inducing factor. The cycle is then repeated.
b) Protein Engineering.

By covalently linking an enzyme to a pore, it can be possible to have only one enzyme in the system and it will be immediately adjacent to the pore (some methods to achieve this are articulated in U.S. application Ser. No. 10/739,585).
c) Block Activity of Enzymes in Bulk Phase Using an Agent Released Only by Capture of a Complex in the Nanopore.

This is illustrated by examples in the figures (FIGS. 1 and 2) and described herein.

Figure 2:
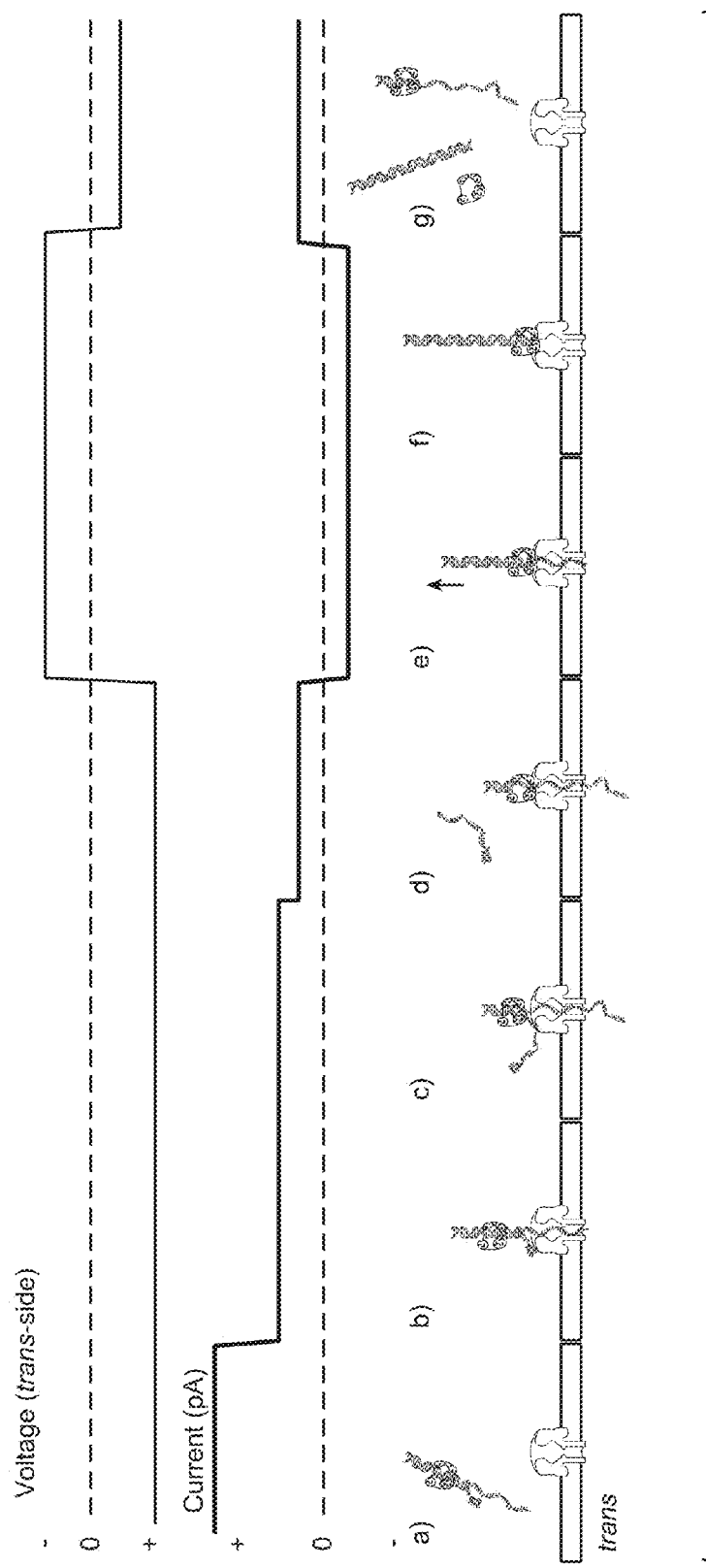
FIG. 2 illustrates an embodiment of the invention whereby enzyme catalytic activity upon a polynucleotide is prevented by a blocking oligomer.

Assume a DNA primer-template pair (at about 1 µM) in a solution that contains all required dNTPs (at about 200 µM each), $Mg^{2+}$ (at about 5 mM), and a processive DNA polymerase (at about 1 µM). The solution is in contact with a single nanopore (for example, α-hemolysin) with an applied voltage such that negatively charged DNA is drawn into the pore. Each primer-template pair is also annealed to a sequence specific molecule at (or close to) the first base that will be added to the primer strand (position n=0). This molecule may have any of numerous structures but will likely be PNA or 2'-O-methyl substituted DNA in the early trials. This blocking molecule either inhibits binding of the polymerase at the initiation site (FIG. 1) or it allows binding but prevents strand synthesis (FIG. 2). The blocking molecule includes a loop that is sufficiently large that it cannot enter the nanopore. Thus, when the strand is pulled into the pore under applied voltage, this loop is hung-up at the pore orifice. This initiates unzipping of the block from the primer template and the blocking molecule dissociates. Polymerase binding and polymerase-catalyzed strand synthesis can follow. The point of this method is that only the strand captured by the nanopore is unlocked from the blocking molecule at the instant it is to be examined. When optimized, a 100 µl volume containing 1 µM of DNA primer/template represents one nanopore-activated molecule in $6 \times 10^{13}$ molecules total.

In an alternative scenario, a blocking molecule, such as a blocking oligomer, may be used to prevent (block) interaction of the DNA template or polynucleotide complex with a binding molecule. The binding molecule may be a compound, such as, but not limited to, a drug composition, a drug candidate, a protein, a peptide, or an enzyme, for example. The blocking oligomer may comprise a blocking moiety at one end of the molecule wherein the blocking moiety interacts with the DNA template or polynucleotide complex to prevent binding of the binding molecule to the DNA template or polynucleotide complex. It may block the biological activity of binding molecule upon the DNA template or polynucleotide complex. It may block the strand displacement within the DNA template or polynucleotide complex. It may block replication and/or extension of the strand within the DNA template or polynucleotide complex. In some cases, it may be preferred to use a blocking oligomer that comprises several moieties, each of which may interact with the DNA template or polynucleotide complex by different means and wherein the blocking oligomer comprises less than 50% of complementary nucleotides. In some circumstances it may desirable for the blocking oligomer to comprise a hairpin loop structure that may alter the binding affinity of a binding molecule to the DNA template or polynucleotide complex. Alternatively, it may be desirable for the blocking primer to comprise a duplex structure that may alter the interaction between a binding molecule to the DNA template or polynucleotide complex. The blocking oligomer may alternatively comprise an oligonucleotide that it not complementary to a polynucleotide to be sequenced. The blocking oligomer may also alternatively comprise a non-oligonucleotide composition whereby the non-oligonucleotide cannot interact with a polynucleotide to be sequenced. These alternative compositions are useful in use to permit efficient removal of the blocking oligomer from a polynucleotide to which it is bound.
d) Deliver a Cofactor Through the Pore from the Trans-Side to the Cis-Side (Containing Enzyme).

This can effectively restrict the required factor to the volume immediately adjacent to the pore. An example is $Mg^{2+}$. This is illustrated by examples in the figure (FIG. 3) and described herein.

Figure 3:
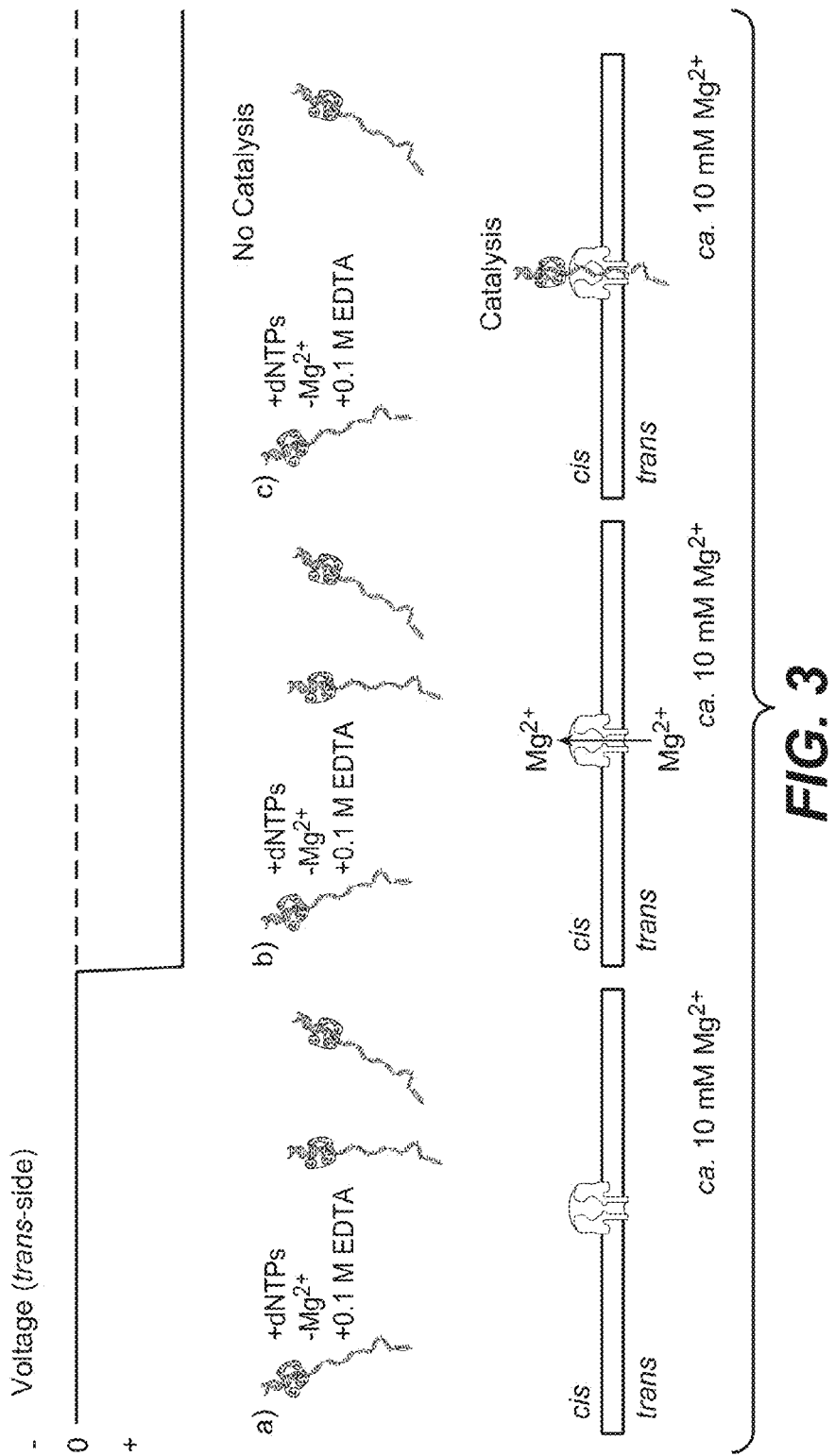
FIG. 3 illustrates an embodiment of the invention whereby enzyme catalytic activity upon a polynucleotide is activated by injection of $Mg^{2+}$ across the nanopore.

An example of this approach is illustrated in FIG. 3. $Mg^{2+}$ is a co-factor essential for catalytic activity by many DNA and/or RNA modifying enzymes including polynucleotide polymerases. In this scenario, $Mg^{2+}$ at greater than millimolar concentrations are added to the trans compartment. The cis compartment comprises all the other reagents, enzymes, and substrates necessary for catalysis. The cis compartment also comprises trace concentrations of EDTA (at about 0.1 mM) to ensure that free $[Mg^{2+}]$ on the cis side is effectively zero in bulk phase. Since $Mg^{2+}$ is a divalent cation under physiological conditions, an applied voltage that attracts a polynucleotide into the nanopore (trans side+) would drive $Mg^{2+}$ in the opposite direction towards the cis compartment. Thus, in the volume (area of medium) immediately adjacent to the pore aperture, the free $[Mg^{2+}]$ is a function of the voltage-driven flux from the trans side to the cis side across the nanopore minus the $Mg^{2+}$ fraction complexed by 0.1 mM EDTA and minus the rate of $Mg^{2+}$ diffusion away from the volume (area of medium) adjacent to the nanopore aperture. $[Mg^{2+}]$ in the bulk volume remains effectively zero and is dominated by EDTA complexation of divalent metal(s).

e) Deliver ssDNA Template Through the Pore from the Trans Side to the Cis Side Containing Enzyme.

This can effectively restrict enzyme processing of the template to the molecule captured in the pore. All other template strands are isolated from enzymes by the impermeable layer (a bilayer for example) supporting the channel.

Enzymes that interact with polynucleotides are known to those of skill in the art and can include, but are not limited to, DNA polymerase such as a DNA polymerase selected from *E. coli* DNA polymerase I, *E. coli* DNA polymerase I Large Fragment (Klenow fragment), phage T7 DNA polymerase, Phi-29 DNA polymerase, *Thermus aquaticus* (Taq) DNA polymerase, *Thermus flavus* (Tfl) DNA polymerase, *Thermus Thermophilus* (Tth) DNA polymerase, *Thermococcus litoralis* (Tli) DNA polymerase, *Pyrococcus furiosus* (Pfu) DNA polymerase, VENT DNA polymerase, *Bacillus stearothermophilus* (Bst) DNA polymerase, AMV reverse transcriptase, MMLV reverse transcriptase, and HIV-1 reverse transcriptase, RNA polymerase such as RNA polymerase selected from T7 RNA polymerase, T3 RNA polymerase, SP6 RNA polymerase, and *E. coli* RNA polymerase, and an exonuclease such as exonuclease Lambda, T7 Exonuclease, Exo III, $RecJ_1$ Exonuclease, Exo I, and Exo T.

Nanopore-Coupled Sequencing by Synthesis

This is a technique for sequencing of single DNA molecules. It combines features of conventional sequencing by synthesis (SBS) with novel nanopore analysis of single DNA molecules under electronic and biochemical feedback control. It relies upon 3' terminator technology, specifically reversible terminator technology.

Figure 4:
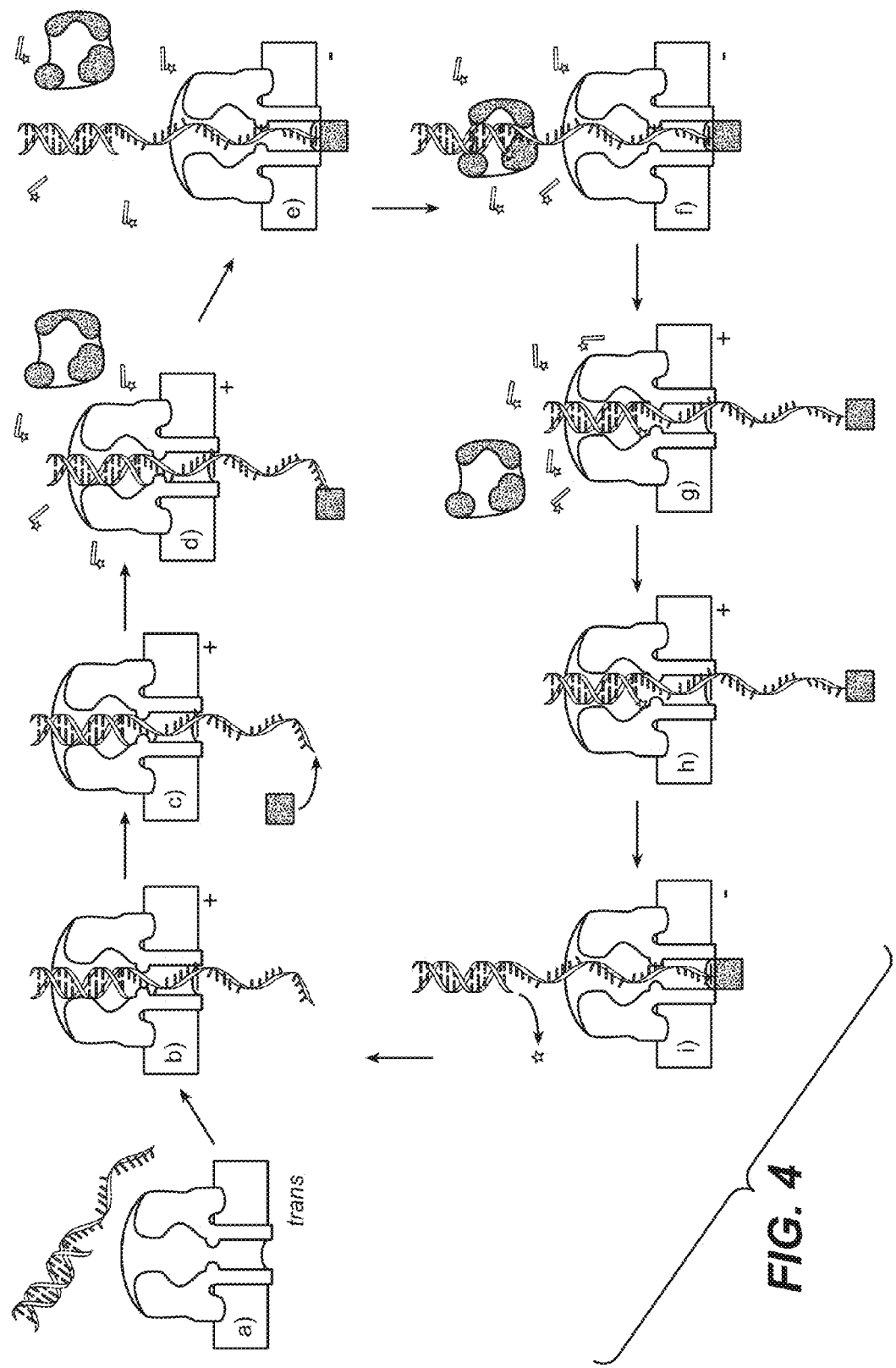
FIG. 4 illustrates an embodiment of the invention showing a method for sequencing single polynucleotide molecules.

The basic strategy is outlined in FIG. 4 for a single nanopore. Our laboratory has developed a strategy to perform this analysis on a chip with up to 400,000 pores. Design and fabrication of such a chip are disclosed below.

As illustrated in FIG. 4, A DNA molecule with both doubled-stranded and single-stranded segments is captured in a nanoscale pore under an applied voltage (trans side positive) (Step a: FIG. 4). DNA of this nature can be generated by timed exonuclease digestion of restriction fragments from genomic DNA or from BAC clones etc. The nanopore is large enough to permit translocation of the ssDNA segment, but the double-stranded segment cannot translocate because its diameter is too large to fit through the narrowest part of the pore. The a-hemolysin pore is ideal for this and is therefore used to illustrate the technique. Strand capture and entry of the duplex segment into the pore vestibule can be confirmed based on current amplitude. Once this is achieved, the voltage is reduced under feedback control (Step b: FIG. 4). At this point, the duplex terminus can be examined and identified by any of several techniques. For example, an earlier patent from this laboratory demonstrated that duplex termini can be identified based on DC current impedance alone. At the same time, the 5'-end of the ssDNA on the trans side of the channel is annealed to an agent (for example, a complementary oligonucleotide or streptavidin) that keeps the strand in the pore indefinitely.

Once the DNA strand is captured and the terminus identified, the cis compartment is perfused with a buffer containing $Mg^{2+}$, a DNA polymerase (for example, the Klenow fragment (KF) of DNA polymerase), and each of the four dNTPs protected with a distinct reversible terminator or by an identical reversible terminator (Step c: FIG. 4). The membrane potential is then reversed thus driving the duplex terminus of the target strand into the cis compartment containing the polymerase and substrates (Step c: FIG. 4). Sufficient time is then allowed for the correct protected dNTP to be added to the target (Step e: FIG. 4). When that time has elapsed, the voltage is reversed once again (trans-side positive (Step f: FIG. 4). The duplex terminus is pulled next to the pore's limiting-aperture where the identity of the added nucleotide is established. If no protected nucleotide has been added, the signal will be the same as in Step b. If this is the case, Steps d to f are repeated until the correct nucleotide is added and identified. Following confirmed addition of the protected nucleotide, the cis compartment is perfused and a deprotecting buffer is added (Step g: FIG. 4). Alternatively, we envision a scenario where a deprotecting agent located only near the nanopore is activated or deactivated under our control that would eliminate the need for perfusion. The deprotecting agent may be an enzyme (for example, alkaline phosphatase), light, or a solute (for example, palladium to catalyze deallylation). After perfusion, a trans-side negative potential is established, driving the duplex terminus into the cis compartment where the reversible terminator can be removed (Step h: FIG. 4). Following this reaction, a trans-side positive potential is re-established, drawing the duplex terminus back to the limiting aperture where it can be examined to determine if deprotection has been successfully achieved, and to confirm the identity of the last base (Step i: FIG. 4). In the event that deprotection is not successful, steps h and i are repeated. If deprotection was successful, the cycle is repeated at step b.

Figure 5:
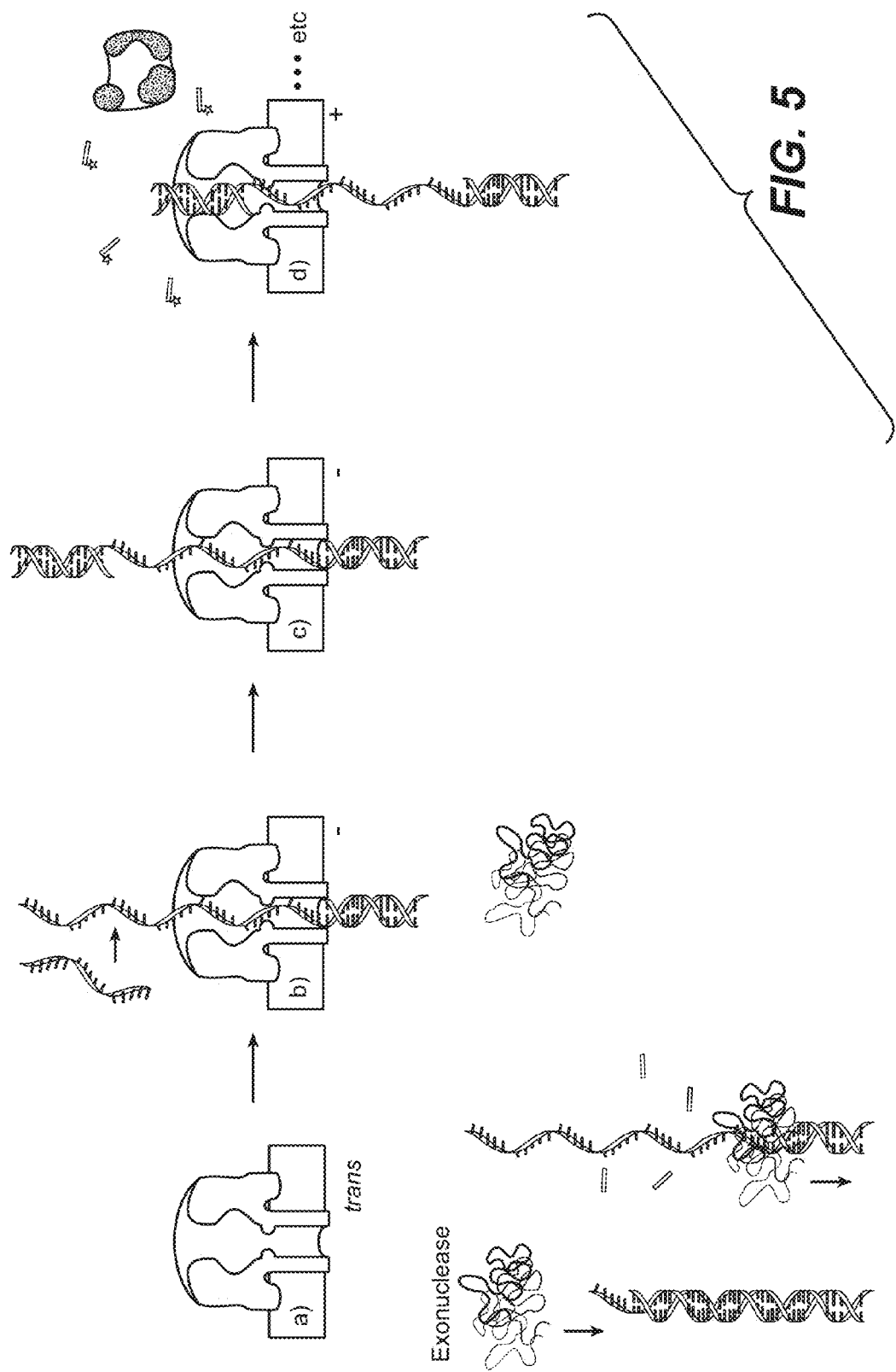
FIG. 5 illustrates an embodiment of the invention showing an alternative method for sequencing single polynucleotide molecules.

The scenario illustrated in FIG. 5 is similar to that illustrated in FIG. 4 except that exonuclease digestion takes place on the trans side of the channel and the DNA is captured in reverse orientation compared to FIG. 4. In this strategy, the template strand is held in place on the cis side by the primer from which strand synthesis originates. The advantage of this scenario is that ssDNA fed into to the nanopore can be generated in blocks by a series of timed exonuclease digestions in the trans compartment. Thus, most of the template would be as dsDNA. For example, if the exonuclease cut at 10 ms per base (on average), a 1000 base overhang could be generated at the end of a 20 kb dsDNA target. When about 1000 bases were successfully filled in by nanopore-coupled SBS, the exonuclease (or a required cofactor) could be re-added to the trans compartment and allowed to react for an additional 10 seconds. The newly generated ssDNA would be filled in base-by-base in the cis compartment as before. This would be repeated in approximately two rounds of 1000 bases to complete the 20 kb fragment.

The pore aperture can vary in dimensions, for example it can have a diameter of between about 0.5 nm and 10 nm in size. For example, the diameter can be about 0.5 nm, 1 nm, 1.25 nm, 1.5 nm, 1.75 nm, 2 nm, 2.25 nm, 2.5 nm, 2.75 nm, 3 nm, 3.5 nm, 4 nm, 4.5 nm, 5 nm, 6 nm, 7 nm, 8 nm, 9 nm, 10 nm, or any dimension there between.

Nanopore-coupled sequencing by synthesis has several advantages over conventional SBS, but the main advantages are these:

1) Nucleotide addition and reversible terminator removal can be directly measured on the individual target strand.

2) The system is controlled both electronically and biochemically so that nucleotide addition and deprotection steps can be repeated rapidly until they are successful.

3) A very long DNA molecule can be captured, manipulated, and quantitatively retained in the pore for an indefinite period.

4) The volume of reagents that are used can be very small (on the order of 1000, and it is possible that a given volume can be recycled hundreds of times. With further development, it may be possible to control activation and deactivation of the deprotection step at the nanopore orifice. This would completely eliminate the need for perfusion.

As is true with conventional SBS, this assay can be performed in parallel. We envision as many as 400,000 independently addressable pores on a 1 cm×1 cm chip that can be fabricated using conventional lithography (see separate disclosure below).

Here we propose polynucleotides that can be used to place and attach macromolecules and other polyanions/polycations at the nanopore aperture. Such macromolecules and polymers can be, for example, a polynucleotide-binding protein, such as, but not limited to a polynucleotide polymerase at the nanopore orifice. A nanopore has the useful property of bringing virtually any desired macromolecular structure to a defined site that can be specified by the user. After being placed at the nanopore site, macromolecular functions can be monitored by the user in a variety of ways. This method can be applied to macromolecules such as, but not limited to, enzymes, receptor proteins, ribozymes, and ribosomes. The method can be applied either to biological pores, or to solid state pores produced in thin inorganic membranes.

The basis of this invention is that a sufficiently long strand of an ionized polymer can be attached to the desired macromolecule, either by covalent or non-covalent bonds. The polymer is then drawn through the nanopore by an electrical voltage applied across the membrane. In some applications, it may be necessary to regulate the force on the macromolecule by varying the voltage acting across the pore. As a result, the macromolecule is placed at the site of the pore with sub-nanometer precision. The macromolecule is then maintained at the pore site either by the electrical force produced by the transmembrane voltage, or by a covalent bond that is engineered between the macromolecule and the pore, or the surface adjacent to the pore. More than one macromolecule can be attached in series if desired.

Functions of the single macromolecule can then be monitored by electrical effects produced at the pore. For instance, the ionic current through the pore can be measured and molecular functions are detected as modulations of the current. Alternatively, an electrode such as a carbon nanotube is placed across the pore and molecular functions are detected by modulations of the electronic current through the nanotube.

Exemplary Uses of the Invention (1) A nanopore device can be used to monitor the turnover of enzymes such as exonucleases and polymerases, which have important applications in DNA sequencing.

(2) A nanopore device can function as a biosensor to monitor the interaction between soluble substances such as enzyme substrates or signaling molecules. Examples include blood components such as glucose, uric acid and urea, hormones such as steroids and cytokines, and pharmaceutical agents, such as, for example, statins or b-blockers, that exert their function by binding to receptor molecules.

(3) A nanopore device can monitor in real time the function of important biological structures such as ribosomes, and perform this operation with a single functional unit.

Figure 6:
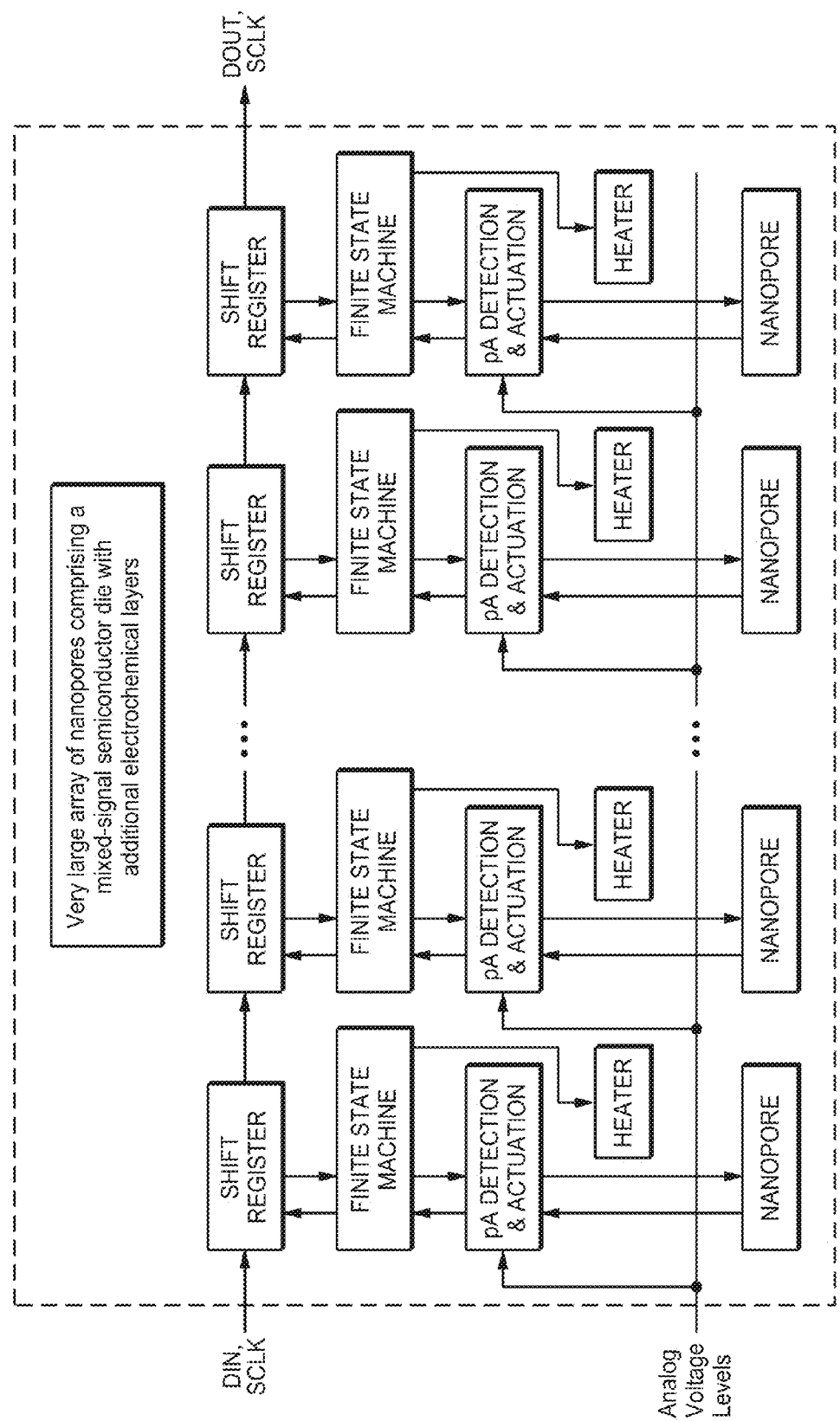
FIG. 6 illustrates a flow chart disclosing the system of one embodiment of the invention.

FIG. 6 illustrates a flow chart disclosing the method of using the invention as manufactured.

Biological nanopores have utility in sequencing of polynucleotides but, due to the low current used (approximately in the tens of picoamps), detection using high-throughput of a single nanopore sequencing device may be limited to approximately 1000 base pairs per second. Manufacturing arrays of biological nanopores that can operate independently of each other, such as used in the manufacture of very large arrays of integrated circuits, a very large scale array of nanopores may perform millions of biochemical reactions and analyses in a single second.

The array elements may be manufactured in a step-wise parallel manner, similar to the manufacture of transistors on integrated circuits. All, or most, of the similar layers of each array element are created in a sequence of single process steps that simultaneously take place on all. Or most, of the array elements.

In order that the each of the hundreds of thousands of biological nanopore elements may be in communication with one another using a minimum number of wired connections, a serial interface and addressable logic can be used to multiplex the large amount of data entering and exiting the array (see flowchart on FIG. 6).

The finite state machine can be created using state-of-the-art commercially available 65 nm process technology, for example from Taiwan Semiconductor Manufacturing Company, Taiwan). A 600×600 array of nanopores can perform 360,000 biochemical reaction and detection/sensing steps at a rate of 1000 Hz. This may enable sequencing of polynucleotides, for example, to proceed at a rate of 360 million baser per second per 1 cm×1 cm die cut from the semiconductor wafer.

Exemplary means for applying an electric field between the cis- and trans-chambers are, for example, electrodes comprising an immersed anode and an immersed cathode, that are connected to a voltage source. Such electrodes can be made from, for example silver chloride, or any other compound having similar physical and/or chemical properties.

Detection

Time-dependent transport properties of the nanopore aperture may be measured by any suitable technique. The transport properties may be a function of the medium used to transport the polynucleotide, solutes (for example, ions) in the liquid, the polynucleotide (for example, chemical structure of the monomers), or labels on the polynucleotide. Exemplary transport properties include current, conductance, resistance, capacitance, charge, concentration, optical properties (for example, fluorescence and Raman scattering), and chemical structure. Desirably, the transport property is current.

Exemplary means for detecting the current between the cis and the trans chambers have been described in Astier et al. (2007, Chem. Phys. Chem. 8: 2189-2194), WO 00/79257, U.S. Pat. Nos. 646,594, 6,673,615, 6,627,067, 6,464,842, 6,362,002, 6,267,872, 6,015,714, and 5,795,782 and U.S. Publication Nos. 2004/0121525, 2003/0104428, and 2003/0104428, and can include, but are not limited to, electrodes directly associated with the channel or pore at or near the pore aperture, electrodes placed within the cis and the trans chambers, ad insulated glass micro-electrodes. The electrodes may be capable of, but not limited to, detecting ionic current differences across the two chambers or electron tunneling currents across the pore aperture or channel aperture. In another embodiment, the transport property is electron flow across the diameter of the aperture, which may be monitored by electrodes disposed adjacent to or abutting on the nanopore circumference. Such electrodes can be attached to an Axopatch 200B amplifier for amplifying a signal.

Applications and/or uses of the invention disclosed herein may include, but not be limited to the following:
1. Assay of relative or absolute gene expression levels as indicated by mRNA, rRNA, and tRNA. This includes natural, mutated, and pathogenic nucleic acids and polynucleotides.
2. Assay of allelic expressions.
3. Haplotype assays and phasing of multiple SNPs within chromosomes.
4. Assay of DNA methylation state.
5. Assay of mRNA alternate splicing and level of splice variants.
6. Assay of RNA transport.
7. Assay of protein-nucleic acid complexes in mRNA, rRNA, and DNA.
8. Assay of the presence of microbe or viral content in food and environmental samples via DNA, rRNA, or mRNA.
9. Identification of microbe or viral content in food and environmental samples via DNA, rRNA, or mRNA.
10. Identification of pathologies via DNA, rRNA, or mRNA in plants, human, microbes, and animals.
11. Assay of nucleic acids in medical diagnosis.
12. Quantitative nuclear run off assays.
13. Assay of gene rearrangements at DNA and RNA levels, including, but not limited to those found in immune responses.
14. Assay of gene transfer in microbes, viruses and mitochondria.
15. Assay of genetic evolution.
16. Forensic assays.
17. Drug discovery.

Filtered Derivative for Adaptive Terminal Step Detection Using a Finite-State Machine (FSM)

Constant voltage experiments with DNA alone and with DNA, Klenow fragment (KF) of DNA polymerase, and complementary dNTP, may be used to determine the thresholds used for detecting the terminal step, that is, dissociation of KF/dNTP from DNA. A filtered derivative of the ionic current amplitude, in addition to the filtered amplitude, may be used to detect the terminal step. In practice, the filtered amplitude is thresholded as disclosed herein, and the filtered derivative is monitored for deflections above a set threshold. Preliminary analysis using the exponentially weighted mean filter has shown that the filtered derivative, applied to the filtered amplitude, deflects by an order of magnitude in the presence of the terminal step. Experiments using both the filtered amplitude and filtered derivative are conducted, tuning the derivative filter and deflection threshold to ensure robust detection of KF dissociation.

Deflections of the derivative may be monitored for terminal step-level deflections, in principle, for any applied voltage in real time using a common (minimum) deflection threshold. In this approach, terminal step detection using only the filtered derivative, and not thresholding of the filtered amplitude is tested. Robust detection using only the filtered derivative may increase the range of voltages that can be used to probe the DNA for KF binding, without requiring identification of filtered current amplitude ranges for each probing voltage. In addition to monitoring the filtered derivative for deflections, logic that monitors the filtered amplitude for relative amplitude changes, without using preset thresholds is developed. The goal is a more adaptive ionic current filtering logic that can robustly detect KF dissociation for a broad range of (possibly varying) probing voltages, using the filtered amplitude and/or filtered derivative, without dependence on present amplitude thresholds.

Polynucleotides homologous to other polynucleotides may be identified by hybridization to each other under stringent or under highly stringent conditions. Single-stranded polynucleotides hybridize when they associate based on a variety of well characterized physical-chemical forces, such as hydrogen bonding, solvent exclusion, base stacking and the like. The stringency of a hybridization reflects the degree of sequence identity of the nucleic acids involved, such that the higher the stringency, the more similar are the two polynucleotide strands. Stringency is influenced by a variety of factors, including temperature, salt concentration and composition, organic and non-organic additives, solvents, etc. present in both the hybridization and wash solutions and incubations (and number thereof), as described in more detail in the references cited above.

Stability of DNA duplexes is affected by such factors as base composition, length, and degree of base pair mismatch. Hybridization conditions may be adjusted to allow DNAs of different sequence relatedness to hybridize. The melting temperature ($T_m$) is defined as the temperature when 50% of the duplex molecules have dissociated into their constituent single strands. The melting temperature of a perfectly matched duplex, where the hybridization buffer contains formamide as a denaturing agent, may be estimated by the following equations:

$$T_m(°\text{ C.}) = 81.5 + 16.6(\log[\text{Na}^+]) + 0.41(\% G+C) - 0.62(\% \text{ formamide}) - 500/L \quad \text{(I) DNA-DNA}$$

$$T_m(°\text{ C.}) = 79.8 + 18.5(\log[\text{Na}^+]) + 0.58(\% G+C) + 0.12(\% G+C)^2 - 0.5(\% \text{ formamide}) - 820/L \quad \text{(II) DNA-RNA}$$

$$T_m(°\text{ C.}) = 79.8 + 18.5(\log[\text{Na}^+]) + 0.58(\% G+C) + 0.12(\% G+C)^2 - 0.35(\% \text{ formamide}) - 820/L \quad \text{(III) RNA-RNA}$$

where L is the length of the duplex formed, [Na$^+$] is the molar concentration of the sodium ion in the hybridization or washing solution, and % G+C is the percentage of (guanine+cytosine) bases in the hybrid. For imperfectly matched hybrids, approximately 1° C. is required to reduce the melting temperature for each 1% mismatch.

Hybridization experiments are generally conducted in a buffer of pH between pH 6.8 to 7.4, although the rate of hybridization is nearly independent of pH at ionic strengths likely to be used in the hybridization buffer (Anderson and Young (1985) "Quantitative Filter Hybridisation." In: Hames and Higgins, editors, Nucleic Acid Hybridisation. A Practical Approach. Oxford, IRL Press, 73-111). In addition, one or more of the following may be used to reduce non-specific hybridization: sonicated salmon sperm DNA or another non-complementary DNA, bovine serum albumin, sodium pyrophosphate, sodium dodecylsulfate (SDS), polyvinyl-pyrrolidone, ficoll, and Denhardt's solution. Dextran sulfate and polyethylene glycol 6000 act to exclude DNA from solution, thus raising the effective probe DNA concentration and the hybridization signal within a given unit of time. In some instances, conditions of even greater stringency may be desirable or required to reduce non-specific and/or background hybridization. These conditions may be created with the use of higher temperature, lower ionic strength and higher concentration of a denaturing agent such as formamide.

Stringency conditions can be adjusted to screen for moderately similar fragments such as homologous sequences from distantly related organisms, or to highly similar fragments such as genes that duplicate functional enzymes from closely related organisms. The stringency can be adjusted either during the hybridization step or in the post-hybridization washes. Salt (for example, NaCl) concentration, formamide concentration, hybridization temperature and probe lengths are variables that can be used to alter stringency (as described by the formula above). As a general guidelines high stringency is typically performed at $T_m$–5° C. to $T_m$–20° C., moderate stringency at $T_m$–20° C. to $T_m$–35° C. and low stringency at $T_m$–35° C. to $T_m$–50° C. for duplex>150 base pairs. Hybridization may be performed at low to moderate stringency (25-50° C. below $T_m$), followed by post-hybridization washes at increasing stringencies. Maximum rates of hybridization in solution are determined empirically to occur at $T_m$–25° C. for DNA-DNA duplex and $T_m$–15° C. for RNA-DNA duplex. Optionally, the degree of dissociation may be assessed after each wash step to determine the need for subsequent, higher stringency wash steps.

High stringency conditions may be used to select for polynucleotide sequences with high degrees of identity to the disclosed sequences. An example of stringent hybridization conditions obtained in a filter-based method such as a Southern or northern blot for hybridization of complementary nucleic acids that have more than 100 complementary residues is about 5° C. to 20° C. lower than the thermal melting point ($T_m$) for the specific sequence at a defined ionic strength and pH. Conditions used for hybridization may include about 0.02 M to about 0.15 M sodium chloride, about 0.5% to about 5% casein, about 0.02% SDS or about 0.1% N-laurylsarcosine, about 0.001 M to about 0.03 M sodium citrate, at hybridization temperatures between about 50° C. and about 70° C. More preferably, high stringency conditions are about 0.02 M sodium chloride, about 0.5% casein, about 0.02% SDS, about 0.001 M sodium citrate, at a temperature of about 50° C. polynucleotide molecules that hybridize under stringent conditions will typically hybridize to a probe based on either the entire DNA molecule or selected portions, for example, to a unique subsequence, of the DNA.

Stringent salt concentration will ordinarily be less than about 750 mM NaCl and 75 mM trisodium citrate. Increasingly stringent conditions may be obtained with less than about 500 mM NaCl and 50 mM trisodium citrate, to even greater stringency with less than about 250 mM NaCl and 25 mM trisodium citrate. Low stringency hybridization can be obtained in the absence of organic solvent, for example, formamide, whereas high stringency hybridization may be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. with formamide present. Varying additional parameters, such as hybridization time, the concentration of detergent, for example, sodium dodecyl sulfate (SDS) and ionic strength, are well known to those skilled in the art. Various levels of stringency are accomplished by combining these various conditions as needed.

The washing steps that follow hybridization may also vary in stringency; the post-hybridization wash steps primarily determine hybridization specificity, with the most critical factors being temperature and the ionic strength of the final wash solution. Wash stringency can be increased by decreasing salt concentration or by increasing the wash temperature. Stringent salt concentration for the wash steps will preferably be less than about 30 mM NaCl and 3 mM trisodium citrate, and most preferably less than about 15 mM NaCl and 1.5 mM trisodium citrate.

Thus, hybridization and wash conditions that may be used to bind and remove polynucleotides with less than the desired homology to the polynucleotide sequences or their complements that encode the present transcription factors include, for example:

6×SSC at 65° C.;
50% formamide, 4×SSC at 42° C.; or
0.5×SSC, 0.1% SDS at 65° C.;

with, for example, two wash steps of 10-30 minutes each. Useful variations on these conditions will be readily apparent to those skilled in the art.

A person of skill in the art would not expect substantial variation among polynucleotide species encompassed within the scope of the present invention because the highly stringent conditions set forth in the above formulae yield structurally similar polynucleotides.

If desired, one may employ wash steps of even greater stringency, including about 0.2×SSC, 0.1% SDS at 65° C. and washing twice, each wash step being about 30 min, or about 0.1×SSC, 0.1% SDS at 65° C. and washing twice for 30 min. The temperature for the wash solutions will ordinarily be at least about 25° C., and for greater stringency at least about 42° C. Hybridization stringency may be increased further by using the same conditions as in the hybridization steps, with the wash temperature raised about 3° C. to about 5° C., and stringency may be increased even further by using the same conditions except the wash temperature is raised about 6° C. to about 9° C. For identification of less closely related homologs, wash steps may be performed at a lower temperature, for example, 50° C.

An example of a low stringency wash step employs a solution and conditions of at least 25° C. in 30 mM NaCl, 3 mM trisodium citrate, and 0.1% SDS over 30 min. Greater stringency may be obtained at 42° C. in 15 mM NaCl, with 1.5 mM trisodium citrate, and 0.1% SDS over 30 min. Even higher stringency wash conditions are obtained at 65° C. to 68° C. in a solution of 15 mM NaCl, 1.5 mM trisodium citrate, and 0.1% SDS. Wash procedures will generally employ at least two final wash steps. Additional variations on these conditions will be readily apparent to those skilled in the art (for example, in US Patent Application No. 20010010913).

Stringency conditions can be selected such that an oligonucleotide that is perfectly complementary to the coding oligonucleotide hybridizes to the coding oligonucleotide with at least about a 5-10× higher signal to noise ratio than the ratio for hybridization of the perfectly complementary oligonucleotide to a polynucleotide encoding a transcription factor known as of the filing date of the application. It may be desirable to select conditions for a particular assay such that a higher signal to noise ratio, that is, about 15× or more, is obtained. Accordingly, a subject polynucleotide will hybridize to a unique coding oligonucleotide with at least a 2× or greater signal to noise ratio as compared to hybridization of the coding oligonucleotide to a polynucleotide encoding known polypeptide. The particular signal will depend on the label used in the relevant assay, for example, a fluorescent label, a colorimetric label, a radioactive label, or the like. Labeled hybridization or PCR probes for detecting related polynucleotide sequences may be produced by oligolabeling, nick translation, end-labeling, or PCR amplification using a labeled nucleotide.

Encompassed by the invention are polynucleotide sequences that are capable of hybridizing to polynucleotides and fragments thereof under various conditions of stringency (for example, in Wahl and Berger (1987) Methods Enzymol. 152: 399-407, and Kimmel (1987) Methods Enzymol. 152: 507-511). Estimates of homology are provided by either DNA-DNA or DNA-RNA hybridization under conditions of stringency as is well understood by those skilled in the art (Hames and Higgins, Editors (1985) Nucleic Acid Hybridisation: A Practical Approach, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

Exemplary Characterization and Uses of the Invention

Sequencing

In one embodiment, the invention may be used to perform sequence analysis of polynucleotides. The analyses have an advantage over the prior art and the current art in that a single analysis may be performed at a single site, thereby resulting in considerable cost savings for reagents, substrates, reporter molecules, and the like. Of additional import is the rapidity of the sequencing reaction and the signal generated, thereby resulting in an improvement over the prior art.

Other methods for sequencing nucleic acids are well known in the art and may be used to practice any of the embodiments of the invention. These methods employ enzymes such as the Klenow fragment of DNA polymerase I, SEQUENASE, Taq DNA polymerase and thermostable T7 DNA polymerase (Amersham Pharmacia Biotech, Piscataway N.J.), or combinations of polymerases and proofreading exonucleases such as those found in the ELONGASE amplification system (Life Technologies, Gaithersburg Md.). Preferably, sequence preparation is automated with machines such as the HYDRA microdispenser (Robbins Scientific, Sunnyvale Calif.), MICROLAB 2200 system (Hamilton, Reno Nev.), and the DNA ENGINE thermal cycler (PTC200; MJ Research, Watertown Mass.). Machines used for sequencing include the ABI PRISM 3700, 377 or 373 DNA sequencing systems (PE Biosystems), the MEGABACE 1000 DNA sequencing system (Amersham Pharmacia Biotech), and the like. The sequences may be analyzed using a variety of algorithms that are well known in the art and described in Ausubel et al. (1997; Short Protocols in Molecular Biology, John Wiley & Sons, New York N.Y., unit 7.7) and Meyers (1995; Molecular Biology and Biotechnology, Wiley VCH, New York N.Y., pp. 856-853).

Shotgun sequencing is used to generate more sequence from cloned inserts derived from multiple sources. Shotgun sequencing methods are well known in the art and use thermostable DNA polymerases, heat-labile DNA polymerases, and primers chosen from representative regions flanking the polynucleotide molecules of interest. Incomplete assembled sequences are inspected for identity using various algorithms or programs such as CONSED (Gordon (1998) Genome Res. 8: 195-202) that are well known in the art. Contaminating sequences including vector or chimeric sequences or deleted sequences can be removed or restored, respectively, organizing the incomplete assembled sequences into finished sequences.

Extension of a Polynucleotide Sequence

The sequences of the invention may be extended using various PCR-based methods known in the art. For example, the XL-PCR kit (PE Biosystems), nested primers, and commercially available cDNA or genomic DNA libraries may be used to extend the polynucleotide sequence. For all PCR-based methods, primers may be designed using commercially available software, such as OLIGO 4.06 primer analysis software (National Biosciences, Plymouth Minn.) to be about 22 to 30 nucleotides in length, to have a GC content of about 50% or more, and to anneal to a target molecule at temperatures from about 55° C. to about 68° C. When extending a sequence to recover regulatory elements, it is preferable to use genomic, rather than cDNA libraries.

Use of Polynucleotides with the Invention

Hybridization

Polynucleotides and fragments thereof can be used in hybridization technologies for various purposes. A probe may be designed or derived from unique regions such as the 5' regulatory region or from a conserved motif such as a receptor signature and used in protocols to identify naturally occurring molecules encoding the polynucleotide protein, allelic variants, or related molecules. The probe may be DNA or RNA, is usually single stranded and should have at least 50% sequence identity to any of the polynucleotide sequences. Hybridization probes may be produced using oligolabeling, nick translation, end-labeling, or PCR amplification in the presence of labeled nucleotide. A vector containing the polynucleotide or a fragment thereof may be used to produce an mRNA probe in vitro by addition of an RNA polymerase and labeled nucleotides. These procedures may be conducted using commercially available kits such as those provided by Amersham Pharmacia Biotech.

The stringency of hybridization is determined by G+C content of the probe, salt concentration, and temperature. In particular, stringency can be increased by reducing the concentration of salt or raising the hybridization temperature. In solutions used for some membrane based hybridizations, addition of an organic solvent such as formamide allows the reaction to occur at a lower temperature. Hybridization can be performed at low stringency with buffers, such as 5×SSC with 1% sodium dodecyl sulfate (SDS) at 60° C., which permits the formation of a hybridization complex between polynucleotide sequences that contain some mismatches. Subsequent washes are performed at higher stringency with buffers such as 0.2×SSC with 0.1% SDS at either 45° C. (medium stringency) or 68° C. (high stringency). At high stringency, hybridization complexes will remain stable only where the polynucleotides are completely complementary. In some membrane-based hybridizations, preferably 35%, or most preferably 50%, formamide can be added to the hybridization solution to reduce the temperature at which hybridization is performed, and background signals can be reduced by the use of other detergents such as Sarkosyl or Triton X-100 and a blocking agent such as denatured salmon sperm DNA. Selection of components and conditions for hybridization are well known to those skilled in the art and are reviewed in Ausubel (supra) and Sambrook et al. ((1989) Molecular Cloning. A Laboratory Manual, Cold Spring Harbor Press, Plainview N.Y.).

Microarrays may be prepared and analyzed using methods known in the art. Oligonucleotides may be used as either probes or targets in a microarray. The microarray can be used to monitor the expression level of large numbers of genes simultaneously and to identify genetic variants, mutations, and single nucleotide polymorphisms. Such information may be used to determine gene function; to understand the genetic basis of a condition, disease, or disorder; to diagnose a condition, disease, or disorder; and to develop and monitor the activities of therapeutic agents. (See, for example, Brennan et al. (1995) U.S. Pat. No. 5,474,796;

Schena et al. (1996) Proc. Natl. Acad. Sci. 93:10614-10619; Baldeschweiler et al. (1995) PCT application WO95/251116; Shalon et al. (1995) PCT application WO95/35505; Heller et al. (1997) Proc. Natl. Acad. Sci. 94:2150-2155; and Heller et al. (1997) U.S. Pat. No. 5,605,662.)

Hybridization probes are also useful in mapping the naturally occurring genomic sequence. The probes may be hybridized to: (a) a particular chromosome, (b) a specific region of a chromosome, or (c) artificial chromosome construction such as human artificial chromosome (HAC), yeast artificial chromosome (YAC), bacterial artificial chromosome (BAC), bacterial P1 construction, or single chromosome cDNA libraries.

Labeling of Molecules for Assay

A wide variety of labels and conjugation techniques are known by those skilled in the art and may be used in various nucleic acid, amino acid, and antibody assays. Synthesis of labeled molecules may be achieved using Promega (Madison Wis.) or Amersham Pharmacia Biotech kits for incorporation of a labeled nucleotide such as $^{32}$P-dCTP, Cy3-dCTP or Cy5-dCTP or amino acid such as $^{35}$S-methionine. Nucleotides and amino acids may be directly labeled with a variety of substances including fluorescent, chemiluminescent, or chromogenic agents, and the like, by chemical conjugation to amines, thiols and other groups present in the molecules using reagents such as BIODIPY or FITC (Molecular Probes, Eugene Oreg.).

Feedback Control of Single Tethered Polymers to Repeatedly Probe Polymer-binding Macromolecules This section explains the basic mechanisms of Klenow Fragment (KF) polymerase and how dissociation of KF from its DNA template can be detected by monitoring the pore current amplitude and event dwell times. Furthermore, the identity of the next base to be added by KF can be found through the presence of long dwell time events (such as, for example, but not limited to >20 msec). The long dwell time events can then be detected and reacted to using dynamic voltage control using a finite state machine (FSM).

It has been shown that KF bound to a DNA hairpin captured in a nanopore can be differentiated from DNA hairpin alone based on current amplitude. Also, the identity the next base to be added the to a DNA hairpin can be identified based on event dwell time. The ability to detect and react to different DNA/enzyme configurations and identify the base being catalyzed by KF is a strong motivator for the control of enzyme function and development of a nanopore-based sequencing method, though further detection and control precision is necessary.

The automated detection and control of single DNA hairpin molecules using the nanopore system is now described. Precise control of single DNA molecules is necessary to make multiple sequential base identifications as would be employed in nanopore-based sequencing. DNA hairpin events are detected and it is shown that their dwell time can be regulated. The results presented demonstrate the level of control necessary for regulation of repeated enzyme binding events with a single piece of DNA captured in a nanopore.

It has been shown that individual DNA hairpins can be detected and controlled based on the amplitude of the Nanopore current signal. The DNA hairpin's dwell time can be extended by reducing the applied voltage upon detection of a hairpin in the pore. Longer dwell times provide more signal that can be used to identify the terminal base pair of the hairpin using machine learning methods (See for example, Vercoutere, et al. (2001) Nat. Biotechnol, 19(3): 248-252; and Akeson (2003) Nucleic acids research, 31: 1311-1318). An extension of the control demonstrated here allows for the use of a single DNA hairpin to capture multiple enzymes, as shown below.

In Examples XX through XXXIX, the repeated capture of enzymes with a single DNA hairpin is demonstrated. Multiple enzyme experiments can be performed rapidly, offering higher throughput compared to atomic force spectroscopy (AFM) and optical tweezer methods, which require manual attachment to the molecules to be measured (See Elio et al. (2005) Nature, 438(7067): 460-465; and Greenleaf and Block (2006) Science, 313(5788): 801). The ability to rapidly probe DNA/enzyme interactions provides further motivation for nanopore-based sequencing.

Basic detection and control of a single DNA hairpin for repeated capture of KF has been demonstrated. Real time detection of enzyme dissociation can be made by recognizing the terminal step present in the nanopore current signal of binary and ternary complex translocation events. Repeatedly probing an enzyme using a single piece of DNA achieves the mechanical action necessary for quick reading of long sequences of DNA using a nanopore. More work needs to be done to regulate single base additions by KF, which is also necessary for sequencing using a nanopore. The terminal step detection methods presented here offer satisfactory results, but fewer false detects are necessary for sequencing using enzyme fishing to be practical.

Improvements to the enzyme fishing mechanism have been proposed. The exponentially weighted moving average filter replace the moving average filter used previously to reduce computational complexity and improve signal smoothing. An enzyme dissociation check that can confirm fishing may be performed with a bare DNA hairpin to ensure each detected enzyme event is a new enzyme binding event. This is important for use of statistical models for sequencing because models assume new enzyme binding events. Higher signal-to-noise can be achieved through use of a longer DNA hairpins that would allow the use of higher control voltages. Reliable detection and reaction to DNA/enzyme unbinding will allow for accurate base identification from repeated enzyme event data.

FIGS. 18 through 25 show how a blocking molecule, in this case a blocking oligonucleotide, can be used to limit enzyme activity to one molecule or complex using a nanopore. Experimental details are more fully described in Examples XXXIV-XXXIX below.

In FIG. 18, DNA primer/template pairs are pre-annealed with a functionalized blocking oligomer that inhibits strand displacement and replication by A-family DNA polymerases (a). Upon nanopore capture (b), a non-complementary tail on the blocking oligomer allows the nanopore to unzip the block as the template is driven into the pore vestibule. The nanopore acts as an electronic helicase. Once the blocking oligomer is removed a finite state machine (FSM) commands a reduction of the membrane potential allowing a complementary oligomer to bind the DNA template in the trans compartment (c) while the dsDNA/ssDNA junction is protected from polymerases in the pore vestibule. Once tethered in this manner, the DNA can be repeatedly 'fished' at defined intervals into the buffer compartment containing enzymes and nucleotide triphosphate (dNTP/rNTP) substrates (d), and then probed for enzyme binding (e) or catalysis under picoNewton forces (f). After one DNA template has been examined, it can be automatically ejected (f)-(g), and another template captured in rapid succession.

Figure 19:
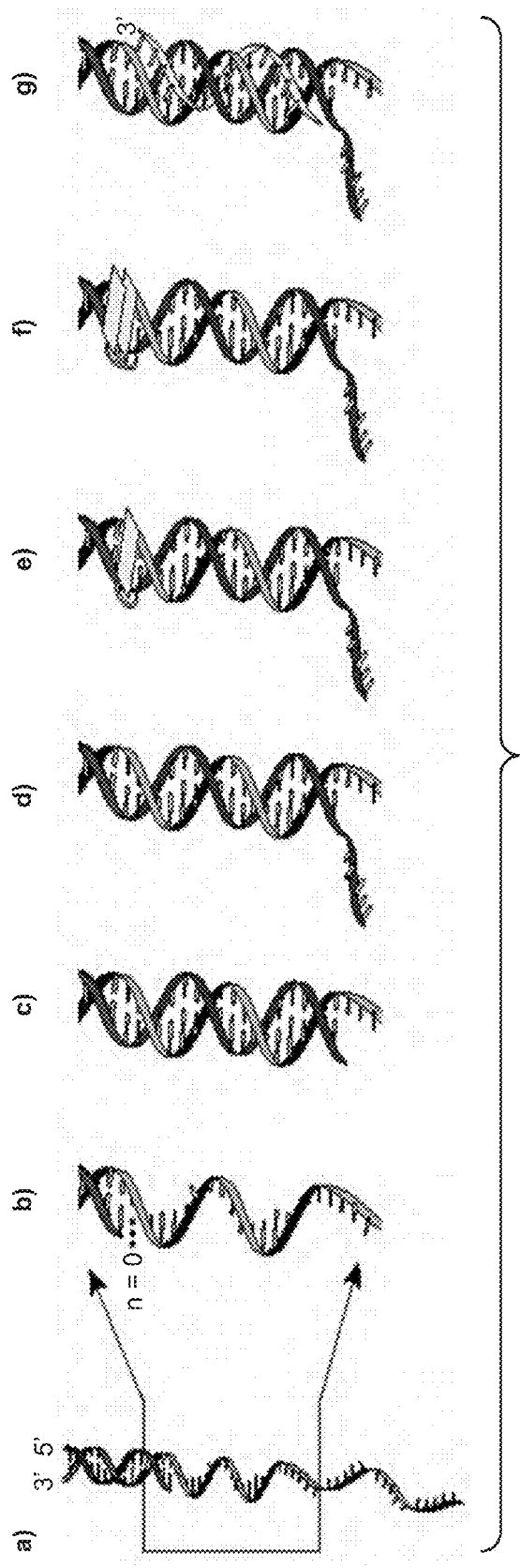
FIG. 19 illustrates exemplary blocking oligomer structures used to inhibit bulk phase DNA synthesis.

FIG. 19 illustrates exemplary blocking oligomer structures that may be used to inhibit bulk phase DNA synthesis. FIG. 19(a) represents a DNA polymerase substrate consisting of a 79 mer template strand (tan and black) and a 23 mer primer strand (dark blue). In (b), the single-stranded region of the template beyond the 3"end of the primer strand is magnified. This region is the target for a series of oligonucleotides (c)-(g) intended to inhibit DNA synthesis in the bulk phase bathing the nanopore. These blocking structures are (c), a standard DNA oligonucleotide (red) complementary to 25 template nucleotides; (d), the oligonucleotide shown in (c), extended on its 3"end by 7 non-complementary cytosine residues; (e), the oligonucleotide shown in (d), with a single acridine residue at its 5"terminus; (f), the oligonucleotide shown in (d), with two acridine residues at its 5' terminus; and (g), a pyrimidine:purine-purine triple helix. The purine-rich third strand of the triple helix is shown in light blue. In panels (e) and (f), acridine residues are depicted as yellow rectangles intercalated into the DNA helix. Two versions of the oligonucleotide shown in e can be used; in one (referred to as "e.i" in the caption for FIG. 20), acridine replaced the 5"base in the sequence of (d), in the other (referred to as "e.ii" in the caption for FIG. 20), the 5' base is present and acridine is incorporated as a 5' extension. For the oligonucleotide in (f), acridine is incorporated at both of these positions. n=0 is the position at which a DNA polymerase would add the first incoming nucleotide during replication.

Figure 20:
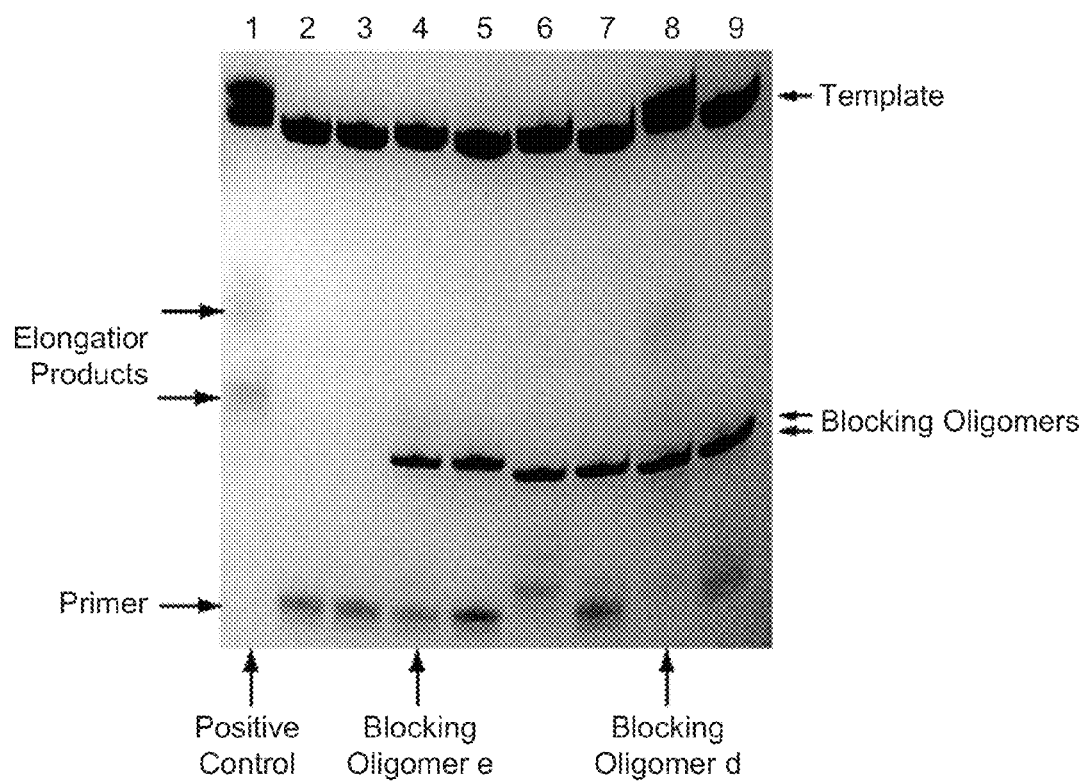
FIG. 20 illustrates blocking oligomer-inhibition of bulk phase primer extension (DNA synthesis) by T7 DNA polymerase (exo-).
Figure 21:
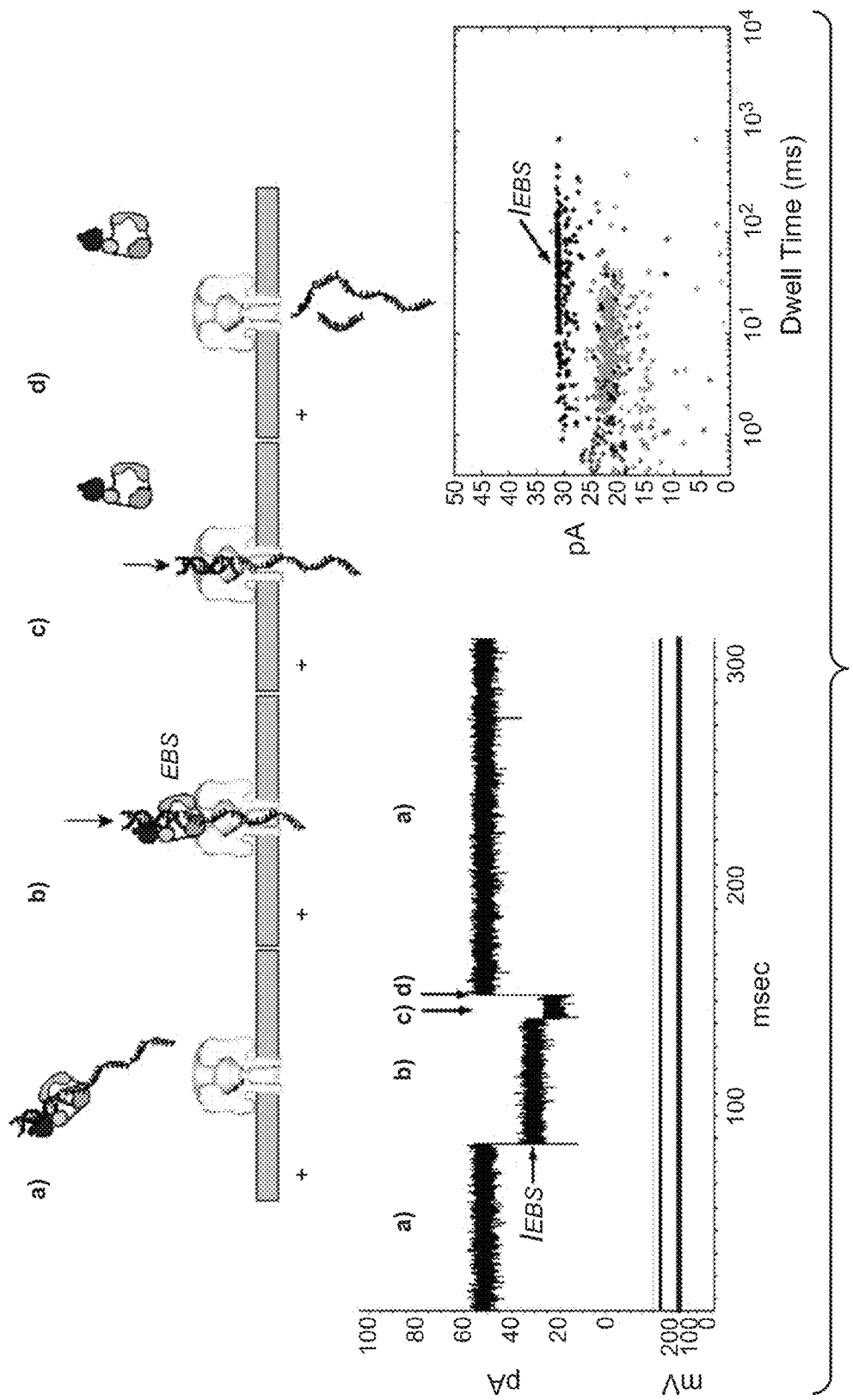
FIG. 21 illustrates a result whereby the nanopore device reliably reports capture of polymerase-DNA-dNTP complexes formed in the bulk phase.
Figure 22:
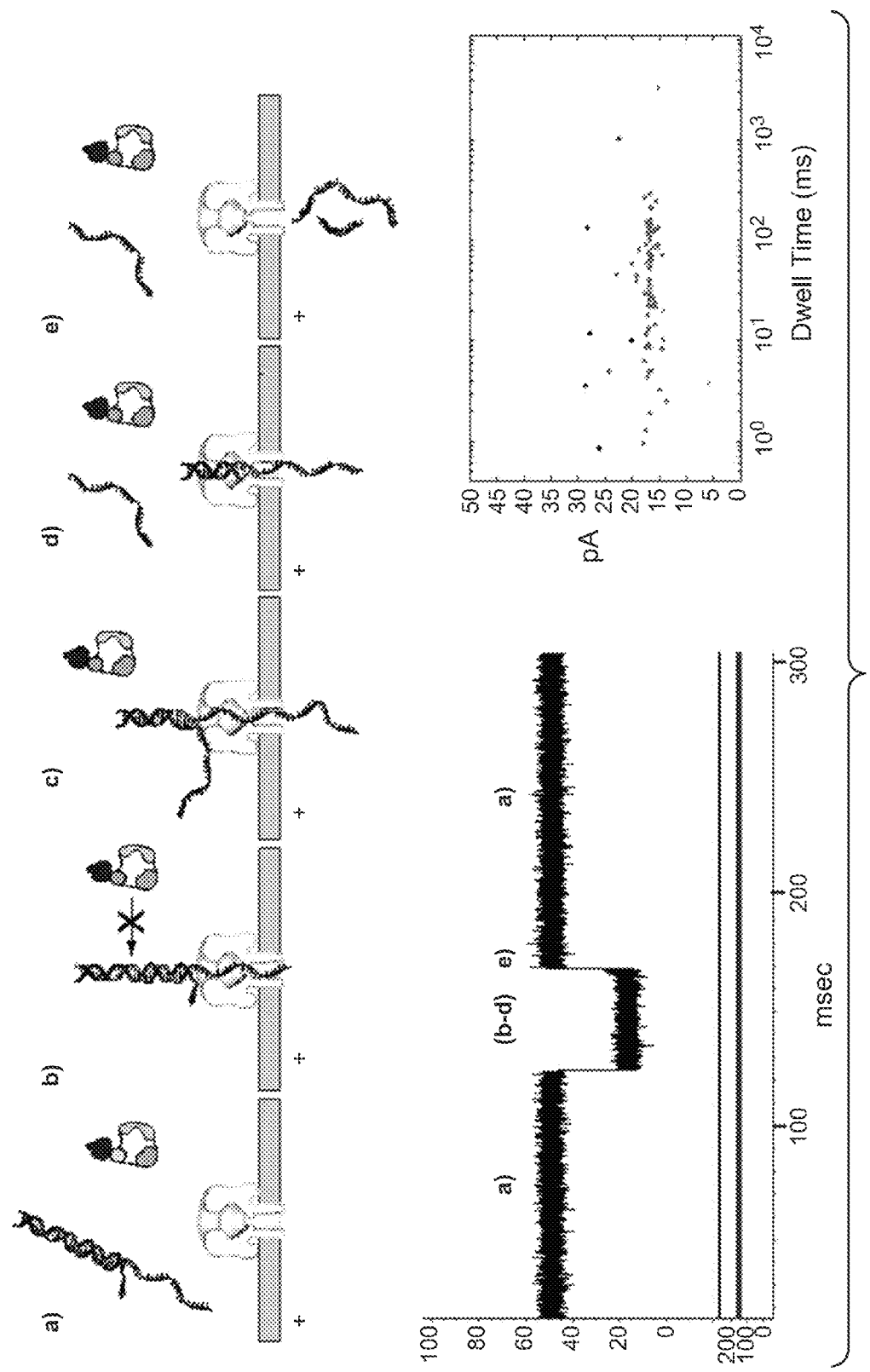
FIG. 22 illustrates evidence using a nanopore that the blocking oligomers prevent T7 DNA polymerase binding in bulk phase.
Figure 23:
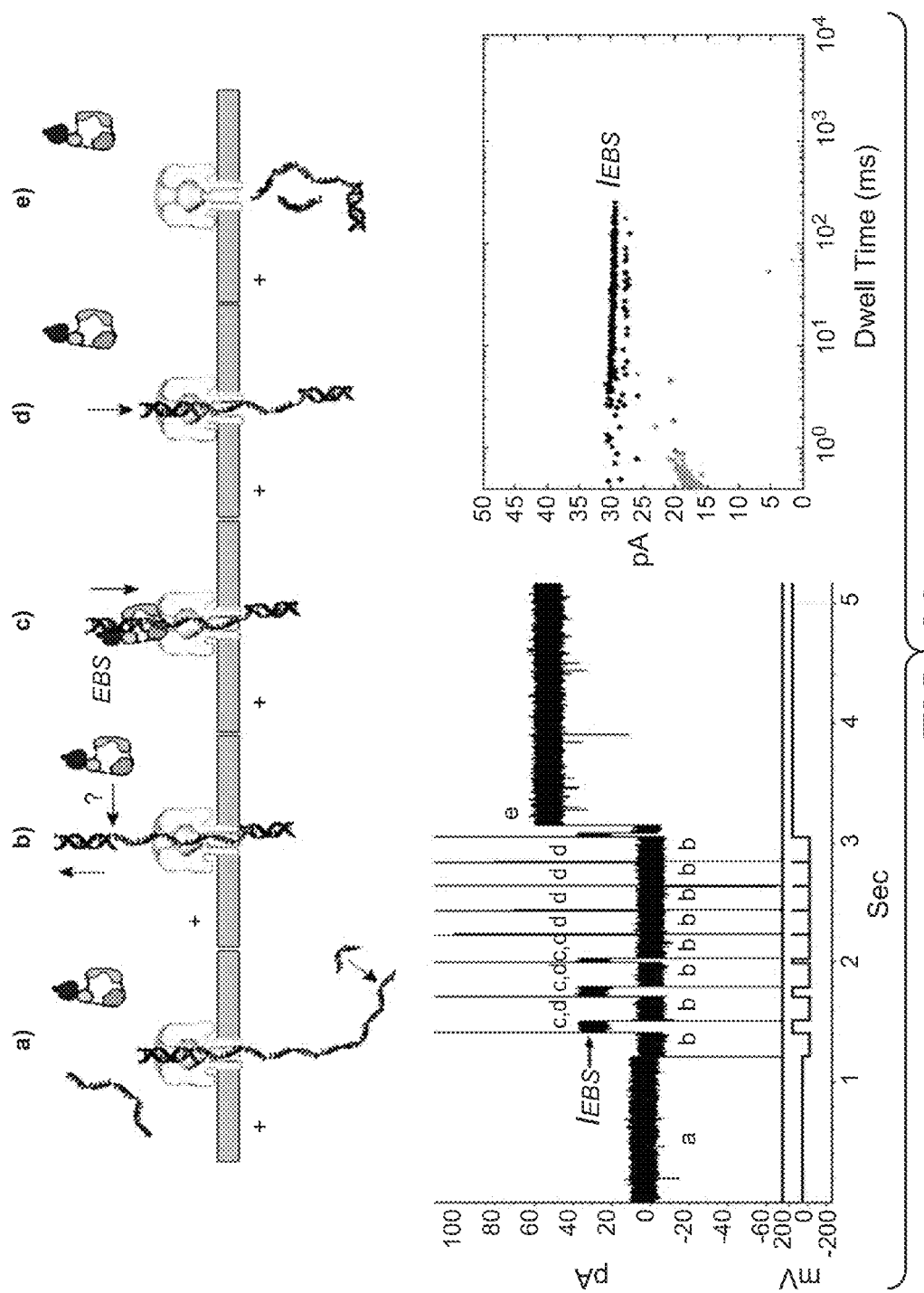
FIG. 23 shows binding of T7 DNA pol to individual DNA substrates is activated electronically at the nanopore.

FIG. 22 shows a key finding that the long, higher amplitude current segments characteristic of polymerase binding without blocking oligomer ($I_{EBS}$ in FIG. 21, see plot of current and 2-D plot) are absent in the presence of the blocking oligomer. A 2-D plot of dwell time vs. amplitude of hundreds of similar events is also included in FIG. 21. The near complete absence of events with EBS amplitudes is consistent with the near complete inhibition of primer extension observed by gel electrophoresis (FIG. 20). Similar experiments may be used to validate the efficacy of more advanced blocking oligomers (FIG. 19) for prevention of ternary complex formation in bulk phase.

Figure 25B:
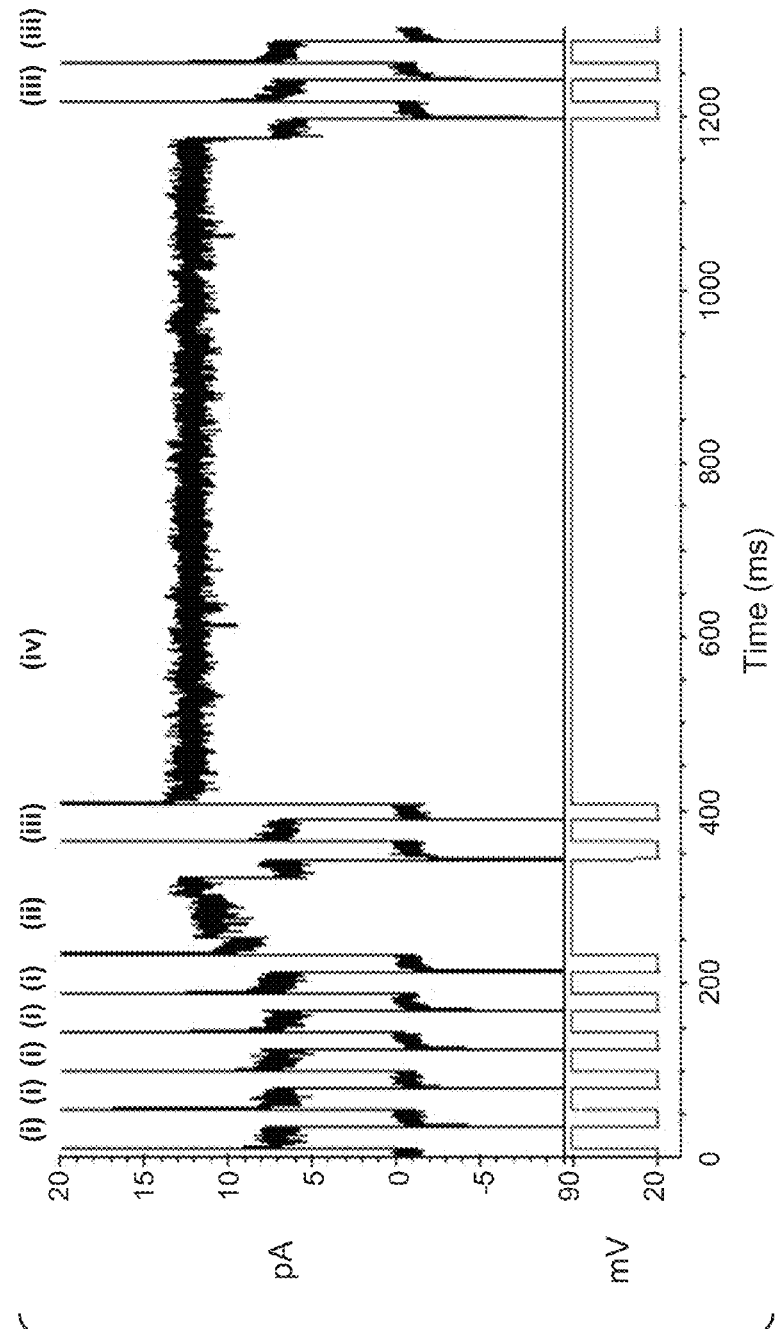
FIG. 25 shows that DNA translocation through the nanopore in real time is driven by T7 DNA polymerase.

We have demonstrated control of DNA displacement at single nucleotide precision on the nanopore FIG. 25. That is, combining active control and the blocking oligomer strategy we showed that T7 DNA polymerase can be used to translocate ssDNA in a biopore. This real time experiment documented enzymatic displacement of three nucleotides under a 90 mV resistive load, and therefore establishes polymerase regulation of DNA in the nanopore.

Diagnostics

The polynucleotides, fragments, oligonucleotides, complementary RNA and DNA molecules, and PNAs may be used to detect and quantify altered gene expression, absence/presence versus excess, expression of mRNAs or to monitor mRNA levels during therapeutic intervention. Conditions, diseases or disorders associated with altered expression include idiopathic pulmonary arterial hypertension, secondary pulmonary hypertension, a cell proliferative disorder, particularly anaplastic oligodendroglioma, astrocytoma, oligoastrocytoma, glioblastoma, meningioma, ganglioneuroma, neuronal neoplasm, multiple sclerosis, Huntington's disease, breast adenocarcinoma, prostate adenocarcinoma, stomach adenocarcinoma, metastasizing neuroendocrine carcinoma, nonproliferative fibrocystic and proliferative fibrocystic breast disease, gallbladder cholecystitis and cholelithiasis, osteoarthritis, and rheumatoid arthritis; acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, benign prostatic hyperplasia, bronchitis, Chediak-Higashi syndrome, cholecystitis, Crohn's disease, atopic dermatitis, dermatomyositis, diabetes mellitus, emphysema, erythroblastosis fetalis, erythema nodosum, atrophic gastritis, glomerulonephritis, Goodpasture's syndrome, gout, chronic granulomatous diseases, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polycystic ovary syndrome, polymyositis, psoriasis, Reiter's syndrome, rheumatoid arthritis, scleroderma, severe combined immunodeficiency disease (SCID), Sjogren's syndrome, systemic anaphylaxis, systemic lupus erythematosus, systemic sclerosis, thrombocytopenic purpura, ulcerative colitis, uveitis, Werner syndrome, hemodialysis, extracorporeal circulation, viral, bacterial, fungal, parasitic, protozoal, and helminthic infection; a disorder of prolactin production, infertility, including tubal disease, ovulatory defects, and endometriosis, a disruption of the estrous cycle, a disruption of the menstrual cycle, polycystic ovary syndrome, ovarian hyperstimulation syndrome, an endometrial or ovarian tumor, a uterine fibroid, autoimmune disorders, an ectopic pregnancy, and teratogenesis; cancer of the breast, fibrocystic breast disease, and galactorrhea; a disruption of spermatogenesis, abnormal sperm physiology, benign prostatic hyperplasia, prostatitis, Peyronie's disease, impotence, gynecomastia; actinic keratosis, arteriosclerosis, bursitis, cirrhosis, hepatitis, mixed connective tissue disease (MCTD), myelofibrosis, paroxysmal nocturnal hemoglobinuria, polycythemia vera, primary thrombocythemia, complications of cancer, cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In another aspect, the polynucleotide of the invention.

The polynucleotides, fragments, oligonucleotides, complementary RNA and DNA molecules, and PNAs, or fragments thereof, may be used to detect and quantify altered gene expression; absence, presence, or excess expression of mRNAs; or to monitor mRNA levels during therapeutic intervention. Disorders associated with altered expression include akathesia, Alzheimer's disease, amnesia, amyotrophic lateral sclerosis, ataxias, bipolar disorder, catatonia, cerebral palsy, cerebrovascular disease Creutzfeldt-Jakob disease, dementia, depression, Down's syndrome, tardive dyskinesia, dystonias, epilepsy, Huntington's disease, multiple sclerosis, muscular dystrophy, neuralgias, neurofibromatosis, neuropathies, Parkinson's disease, Pick's disease, retinitis pigmentosa, schizophrenia, seasonal affective disorder, senile dementia, stroke, Tourette's syndrome and cancers including adenocarcinomas, melanomas, and teratocarcinomas, particularly of the brain. These cDNAs can also be utilized as markers of treatment efficacy against the diseases noted above and other brain disorders, conditions, and diseases over a period ranging from several days to months. The diagnostic assay may use hybridization or amplification technology to compare gene expression in a biological sample from a patient to standard samples in order to detect altered gene expression. Qualitative or quantitative methods for this comparison are well known in the art.

The diagnostic assay may use hybridization or amplification technology to compare gene expression in a biological sample from a patient to standard samples in order to detect altered gene expression. Qualitative or quantitative methods for this comparison are well known in the art.

For example, the polynucleotide or probe may be labeled by standard methods and added to a biological sample from a patient under conditions for the formation of hybridization complexes. After an incubation period, the sample is washed and the amount of label (or signal) associated with hybridization complexes, is quantified and compared with a standard value. If the amount of label in the patient sample is significantly altered in comparison to the standard value, then the presence of the associated condition, disease or disorder is indicated.

In order to provide a basis for the diagnosis of a condition, disease or disorder associated with gene expression, a normal or standard expression profile is established. This may be accomplished by combining a biological sample taken from normal subjects, either animal or human, with a probe under conditions for hybridization or amplification. Standard hybridization may be quantified by comparing the values obtained using normal subjects with values from an experiment in which a known amount of a substantially purified target sequence is used. Standard values obtained in this manner may be compared with values obtained from samples from patients who are symptomatic for a particular condition, disease, or disorder. Deviation from standard values toward those associated with a particular condition is used to diagnose that condition.

Such assays may also be used to evaluate the efficacy of a particular therapeutic treatment regimen in animal studies and in clinical trial or to monitor the treatment of an individual patient. Once the presence of a condition is established and a treatment protocol is initiated, diagnostic assays may be repeated on a regular basis to determine if the level of expression in the patient begins to approximate the level that is observed in a normal subject. The results obtained from successive assays may be used to show the efficacy of treatment over a period ranging from several days to months.

Purification of Ligand

The polynucleotide or a fragment thereof may be used to purify a ligand from a sample. A method for using a polynucleotide or a fragment thereof to purify a ligand would involve combining the polynucleotide or a fragment thereof with a sample under conditions to allow specific binding, detecting specific binding, recovering the bound protein, and using an appropriate agent to separate the polynucleotide from the purified ligand.

In additional embodiments, the polynucleotides may be used in any molecular biology techniques that have yet to be developed, provided the new techniques rely on properties of polynucleotides that are currently known, including, but not limited to, such properties as the triplet genetic code and specific base pair interactions.

To our knowledge, we are the first investigators to use an FPGA to control and measure complexes in a nanopore. (See Hornblower et al. (2007) Nature Meth. 4: 315-317.) We believe that similar functionality could be achieved with an appropriate microprocessor. FSM logic has been used as part of a machine learning approach used to identify the terminal base pair of the blunt end of DNA hairpins (see Vercoutere, et al. (2001) Nat. Biotechnol, 19(3): 248-252; Winters-Hilt et al. (2003) Biophys. J., 84(2): 967-976). This is a much different application of an FSM in which its primary role was for training the machine learning models offline; our FSM functionality is used for online voltage control.

Direct control of ssDNA in a nanopore (no enzymes) has been demonstrated (Bates et al (2003) Biophysical Journal, 84: 2366-2372) in which detection of DNA is based on monitoring the raw amplitude relative to a threshold level. Voltage level changes, comparable to those employed in Wilson et al. ((2008) ibid), were commanded to explore the zero and low voltage effects on ssDNA-pore interactions. In contrast to thresholding the raw ionic current amplitude, our approach filters the current in real time (details given in the Examples).

Alternative methods for single-molecule sensing and manipulation include optical tweezers and atomic force microscopy (see Bustamante et al. (2003) Nature, 421: 423-427). For example, optical trapping has been used to sequence DNA by attaching a processive enzyme to a polystyrene bead (see Abbondanzieri et al (2005) Nature, 438(24):460-465; and Greenleaf and Block (2006) Science, 313:801). At present, greater spatial and temporal resolution of single DNA molecule polymerization has been achieved than with nanopores. However, these methods generally require more preparative steps, and far fewer molecules can be analyzed over a common time period.

Our invention uses feedback control of a single tethered DNA molecule suspended in a nanopore for repeated capture and subsequent dissociation of individual DNA-binding enzymes. There are two phases to our implementation.

First, a single DNA molecule with single and double stranded segments is captured, by the single-stranded end, and then tethered, by making the single-stranded segment double-stranded on the trans side. In this configuration, with double-stranded segments on both cis and trans sides of the channel, the DNA will remain in the channel until a sufficient voltage force unzips the double-stranded segments from the cis or trans side. The length of the single-stranded segment in the channel is chosen such that, under negative voltages, exposure of the single-to-double stranded (ss-ds) junction in the cis chamber is sufficiently available for KF binding.

In the second phase, the tethered DNA is used for repeated capture and dissociation of KF enzymes in the cis chamber of the nanopore. By analogy with fishing, the DNA is the line and bait (with the ss-ds junction as the hook), and the enzymes are the fish (which can be caught only one at a time). Details are now given on our setup, control logic, related approaches in the literature, and our initial demonstration of repeated KF binding to a tethered DNA molecule in a nanopore.

Impact and Refinement of Tethered DNA Capability

For the purpose of exploring the interaction of enzymes that bind or modify DNA or RNA (exonucleases, kinases, and other polymerases), with DNA or RNA captured in a nanopore, we consider that the invention disclosed herein will have the following technological impacts:

Substantial Increase in Data Throughput.

In the tethered configuration, a negative voltage is used in fishing mode, and a positive voltage is used for probing mode. In probing mode, all information contained in the ionic current can be used for characterization of the polymer alone or polymer-enzyme interactions, at any desired probing voltage. In non-tethered configuration, independent events (including capture, blockage of nanopore, and eventual translocation of polymer) contain the information relevant for analysis of polymer alone or polymer-enzyme interactions. A sufficient voltage is required for capture of each molecule, the time between events is not controllable, and lower capture voltages increase the time between events. Thus, the tethered configuration increases the throughput of analyzable data, by increasing the number of analyzable events over a common period and by increasing the range of probing voltages.

Reduction in Non-Analyzable Data.

In probing mode, the ionic current contains information about the tethered polymer alone or the interaction of an enzyme bound to the tethered polymer. In non-tethered configuration, up to 50% of events recorded within an experiment can be unrelated to the kinetics of interest. For example, brief blockades caused by the ds-end of a DNA hairpin contacting the cis-side of the pore would be included in data in the non-tethered configuration, but not in the tethered configuration.

Substantial Increase in Sensitivity of Nanopore Sensor for Real-Time Detection of the Addition of Biological Components in Cis Chamber.

Post-experiment analysis demonstrates the sensitivity of nanopore sensors for detection of the presence of $Mg^{2+}$ cofactor and complementary dNTP of KF. In both cases, detection is based on the increase in dwell time for the KF-bound portion of binary/ternary events. By monitoring the dwell time of KF-bound portions of events in real time, the tethered configuration offers a new capability for online detection of addition of $Mg^{2+}$ and complementary dNTP components to the cis-chamber. The same capability can be utilized with other enzymes and their corresponding event-sensitive components. In our future tethered DNA experiments with KF, real-time detection capabilities will be explored as a function of fishing time, dNTP concentration, $Mg^{2+}$ concentration, and probing voltage.

Screening of Drug Candidates

Another aspect of the invention is to use the methods disclosed herein to analyse and detect binding of an activated DNA-binding molecule, for example, a transcriptional regulator such as a transcription factor, a nucleotide polymerase, an transcriptional enhancer, and a regulatory polynucleotide, or the like, that will only bind the DNA in the presence of a ligand. In one typical example, the ligand is a drug candidate and the DNA-binding molecule is a transcription factor that is activated by an endogenous ligand. In another alternative, the DNA-binding molecule will only bind the DNA in the absence of a ligand. Such ligands having either activity or both activities are well known in the art and are disclosed herein. For example, typical ligands such as, but not limited to, retinoic acid, thyroid hormone (for example, T3 and T4), steroid hormones such as androgens, estrogens, progesterones, cortisols, and the like, peroxisome-proliferators, isoprenoid alcohols (for example, farnesol), as well as products of intermediary metabolism, such as, but not limited to, sugars and their derivatives, lipids and their derivatives, nucleotiside co-factors and the like, and nucleic acids, such as, but not limited to, miRNAs, asRNAs, and products of pseudogenes, may be the endogenous (naturally-occurring) ligand. It is desirable and one of the considerations of the invention, that candidate synthetic drugs that have homologies, structural, chemical, and/or spatial, may be identified using the methods disclosed herein and may be used in various therapies for diseases and disorders, for example, neurological disorders, reproductive disorders, disorders of metabolism, metaplasia, such as cancer, and inflammatory disorders.

The methods disclosed herein can provide for high-throughput screening of such candidate drugs at low cost and having a high rate of confidence in any data so derived.

The invention will be more readily understood by reference to the following examples, which are included merely for purposes of illustration of certain aspects and embodiments of the present invention and not as limitations.

EXAMPLES

Herein are described several examples to demonstrate the capability of measuring macromolecules and polanions or polycations.

Example I

Enzyme Binding is Prevented by a Blocking Oligomer

For an illustration of this method, see FIGS. 1(a) through 1(g). (a) In this scenario, the blocking oligomer is bound to the primer/template in bulk phase. Structure of the ternary complex prevents binding of the enzyme to the junction between the dsDNA and ssDNA segments of the target DNA where the first nucleotide would be incorporated. (b) Capture of a blocked primer/template under an applied voltage (trans side positive) threads the ssDNA into the pore and perches the dsDNA above the vestibule. This occurs because the loop at the end of the blocking oligomer is too large to enter the vestibule. The current reports capture of the complex in this state. (c) Under the applied voltage, the ssDNA segment advances in the pore toward the trans-side and processively unzips base-pairs between the blocking oligomer and the template. The energy cost of releasing each base pair independently is small (about 2.5 kcal/mol), so it proceeds rapidly under force. During this unzipping process the current is the same as in (b) because the dsDNA segment cannot enter the vestibule. (d) Release of the blocking oligomer following unzipping. Absent the blocking oligomer, the dsDNA segment of the target DNA can enter the pore vestibule. This results in a measurable reduction in current that signals release of the blocking oligomer and activation of the target DNA. (e) Voltage reversal exposes the activated dsDNA/ssDNA junction for enzyme binding. By reversing voltage, the negatively charged DNA is driven back into the cis compartment. (f) Absent the blocking oligomer, enzymes can bind to the DNA at the targeted position (the dsDNA/ssDNA junction in this example). (g) Probing for bound enzyme or DNA modification. Following a defined amount of time (typically hundreds of microseconds to seconds), the voltage can be reversed once again to its original polarity, thus pulling the DNA back into the nanopore. Current readout can be used to determine if an enzyme has been bound (shown) or if the DNA duplex terminus has been modified (not shown). If the result is negative, steps (e)-(g) can be repeated.

Example II

Enzyme Catalysis is Prevented by a Blocking Oligomer

For an illustration of this method, see FIGS. 2(a) through 2(g). (a) In this scenario, the blocking oligomer is bound to the primer/template in bulk phase. Structure of the ternary complex permits binding of the enzyme to the target DNA but catalysis and processing along the template are prevented. (b) Capture of a blocked primer/template under an applied voltage (trans-side positive) threads the ssDNA into the pore and perches the dsDNA above the vestibule. This occurs because the loop at the end of the blocking oligomer is too large to enter the vestibule. The current reports capture of the complex in this state. (c) Under the applied voltage, the ssDNA segment advances in the pore toward the trans-side and processively unzips base-pairs between the blocking oligomer and the template. The energy cost of releasing each base pair independently is small (about 2.5 kcal/mol), so it proceeds rapidly under force. During this unzipping process the current is the same as in (b) because the dsDNA segment cannot enter the vestibule. (d) Release of the blocking oligomer following unzipping results in activation of the complex. Unlike the scenario disclosed in FIG. 1, the dsDNA segment of the target DNA cannot enter the pore vestibule when the block dissociates because the bound enzyme is too large to enter. Thus the average current does not change. (e) Reducing the applied voltage permits the enzyme to proceed. There remains sufficient ionic current for analysis. (f) The template strand is copied to completion. (g) The complex dissociates and the nanopore is now ready to capture and activate another DNA target (see step a).

Example III

Enzyme Catalysis is Activated by Injection of $Mg^{2+}$ Across a Nanopore

For an illustration of this method, see FIGS. 3(a) through 3(c). (a) In this example scenario, the cis compartment contains all components necessary for DNA polymerase activity except for $Mg^{2+}$. Thus, no catalysis can take place. (b) When voltage is applied (trans-side +), $Mg^{2+}$ is driven across the pore into the cis compartment. (c) When a DNA-polymerase complex is captured by the pore, the $Mg^{2+}$ concentration in the volume immediately adjacent to the pore is sufficiently high to permit $Mg^{2+}$ occupation of the two critical loci in the enzyme's catalytic site. Polymerization of the copied strand can then occur. Ternary complexes in the bulk phase cannot catalyze DNA synthesis because the $Mg^{2+}$ concentration distal from the pore is essentially zero. This scenario could be applied to other substances that are required for DNA synthesis and that are small enough to permeate the nanopore under controlled conditions.

Example IV

Measuring Polymerase Activity Using a Biological Nanopore, α-Hemolysin

The polymerase activity of DNA polymerase I is largely contained in a smaller structure called the Klenow fragment. In this application, the Klenow fragment is allowed to bind to a strand of DNA (the template) that has undergone complementary base pairing with an oligomer of defined base sequence. The protein is drawn to the pore and the ionic current through the pore is thereby reduced. Two different enzymatic functions can be monitored. 1) When the protein is released from its binding site on the primer-template complex, a characteristic transient reduction of ionic current is produced. 2) When the enzyme is supplied by the appropriate dNTP substrate, a characteristic lengthening of the residence time of the enzyme in the pore is produced. Incorrect dNTP substrates do not alter the residence time.

Example V

Detecting Ligand Binding to a Receptor Protein

The cytoplasmic estradiol receptor is covalently linked to a 100mer of polyaspartic acid by formation of an appropriate covalent bond, such as that produced by a cross-linking agent. The receptor is positioned at a 3 nm diameter silicon nitride pore by the electric field acting on the polyaspartic acid in its anionic form. The pore has a monolayer of a bifunctional alkyl sulfide attached to a gold layer on the pore. After positioning, the receptor is covalently bonded to the pore by formation of disulfide bonds between the alkyl groups on the pore and cysteine groups on the receptor. When estradiol is present, it binds to the high affinity site on the receptor and alters ionic current though the pore, thereby providing a means of detecting this steroid hormone with single-molecule sensitivity.

Example VI

Detecting Glucose Oxidase Activity

Following the procedure outlined in Example V, a glucose oxidase molecule is attached to a silicon nitride pore. When glucose is present, the enzymatic action produces detectable transient changes in the ionic current through the pore as the glucose binds to the active site, oxidation, and release of products.

Example VII

Monitoring Ribosome Function

A ribosome preparation is exposed to a specific mRNA in the presence of a commonly used translation system such as cytosolic extract of E. coli. The system is maintained near 0° C. in order to inhibit ribosome function. Alternatively ribosomes may be inactivated by excluding a required cofactor such as an elongation factor or tRNAs. When a single ribosome attaches to the mRNA, it can be positioned at the pore by drawing the mRNA through the pore by the action of a transmembrane voltage of 100 mV or more. The mixture is then rapidly warmed to 25° C. to initiate protein synthesis or addition of a required cofactor. The individual steps of protein synthesis are then monitored by the combined effects on ionic current that are produced by mRNA being drawn through the pore by the ribosome action, and cyclic conformational changes of the ribosome as it proceeds through the steps of translation.

Example VIII

Figure 7:
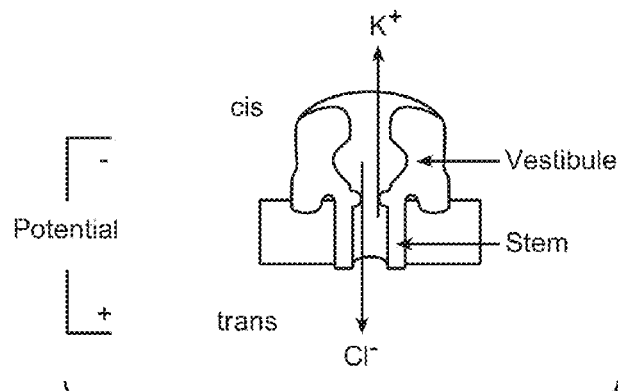
FIG. 7 illustrates a single α-hemolysin protein channel (mushroom shape) inserted into lipid bilayer. Under applied potential (trans-side positive), $K^+$ ions flow to the cis side, and Cl— ions flow to the trans side. The vestibule and stem of the pore channel are shown.
Figure 8:
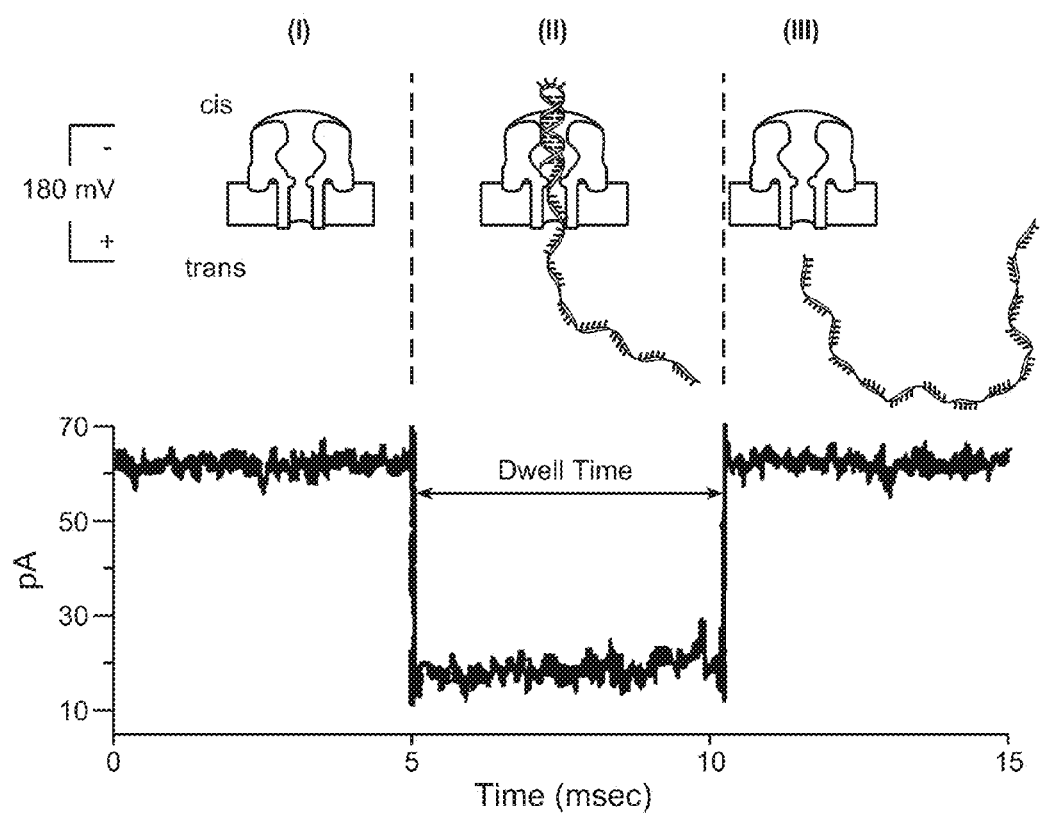
FIG. 8 illustrates a schematic of nanopore and DNA (top), and plot of representative ionic current signal (bottom) during a 20 base pair hairpin DNA translocation event under 180 mV applied potential. (I) At 180 mV, KCl ions pass through the open channel resulting in ~64 pA current. (II) Upon capture of the single-stranded end of the DNA molecule into the cis opening of the pore, the flow of ions is reduced to ~20 pA. (III) After ~5 msec, the voltage unzips the hairpin, causing ssDNA to pass through the pore into the trans chamber, completing the measured blockaded event. The duration of the event is referred to as dwell time.

Feedback Control of a Single Tethered DNA Molecule Suspended in a Nanopore to Repeatedly Probe DNA-Binding Enzymes In the biological nanopore setup, a planar lipid bilayer is created across a 50-100 μm TEFLON aperture in a KCl solution, and a single α-hemolysin protein channel self-inserts into the planar lipid. The channel (pore) is 15 nm in length and varies in diameter. The cis-opening of the pore is 2.6 nm wide, opening to a 3.6 nm vestibule before narrowing to a limiting 1.5 nm width at the beginning of the stem. The remainder of the stem up to the trans-opening is 2 nm wide. The vestibule is large enough for double-stranded DNA (dsDNA) to enter, but the limiting stem is just wide enough for single-stranded DNA (ssDNA) to pass through. AgCl electrodes are used to apply a potential across the bilayer that produces an ionic current through the pore (FIG. 7). The field created by this voltage pulls the negatively charged phosphate backbone of the ssDNA or RNA through the pore, passing from the cis side to the trans side of the pore with the trans-side voltage positive. As molecules translocate, the pore becomes partially blocked by the translocating molecule, causing a drop in current. These translocation events can be characterized by the amplitude of the attenuated (blockade) current and the time the molecule spends in the pore, defined as the dwell time. A schematic of the nanopore system and an example DNA translocation event is shown in FIG. 8. The DNA shown in FIG. 8 has single and double-stranded segments, with the double-stranded segment as a 20 base pair hairpin (20 bphp). The DNA is captured by the single-stranded end into the nanopore, and translocates once the voltage field force causes the hairpin to unzip within the vestibule. This configuration has utility towards a part of the instant invention. The utility of the double-stranded segment is that it extends the dwell time (by stopping translocation) of the DNA, briefly, until the voltage shears the segment into single stranded DNA and the DNA translocates. Additionally, longer double-stranded segments yield longer dwell times at a given voltage. In contrast, for ssDNA or RNA, translocation rates reach up to 2 nucleotides/μsec with no pauses in translocation under capture-level voltages.

We note that the double-stranded segment may alternatively be formed by annealing a primer DNA segment, with the complementary bases, to the end of single-stranded DNA. The key is that, in our configuration, the captured DNA molecule must have single and double-stranded segments. This structure facilitates capture and retention: the single-stranded end is captured, and the double-stranded end increases the dwell time, providing time to detect capture and react by reducing the voltage to a hold level (explained in more detail below). Another key reason for using this DNA structure is that the enzyme exploited in our proposed approach binds to the DNA precisely at the single-to-double stranded junction of the DNA.

Example IX

Nanopores and Enzymes

We have used biological nanopores to probe the interaction of enzyme with a captured DNA molecule. Under an applied voltage, the ssDNA end of enzyme-bound DNA is captured in the nanopore, with the enzyme residing on top of the nanopore being too large to translocate through it. Kinetics of *Escherichia coli* exonuclease I (ExoI) binding to ssDNA has been quantified using voltage ramps for nanopore-based force spectroscopy. Specifically, upon detection of capture of ssDNA, voltage is automated to briefly hold the ssDNA-ExoI complex, then implement a voltage ramp until ExoI dissociates and the ssDNA translocates through the pore. The time-to-dissociation under the applied voltage ramp is in turn used to estimate binding rate constants.

Figure 9A:
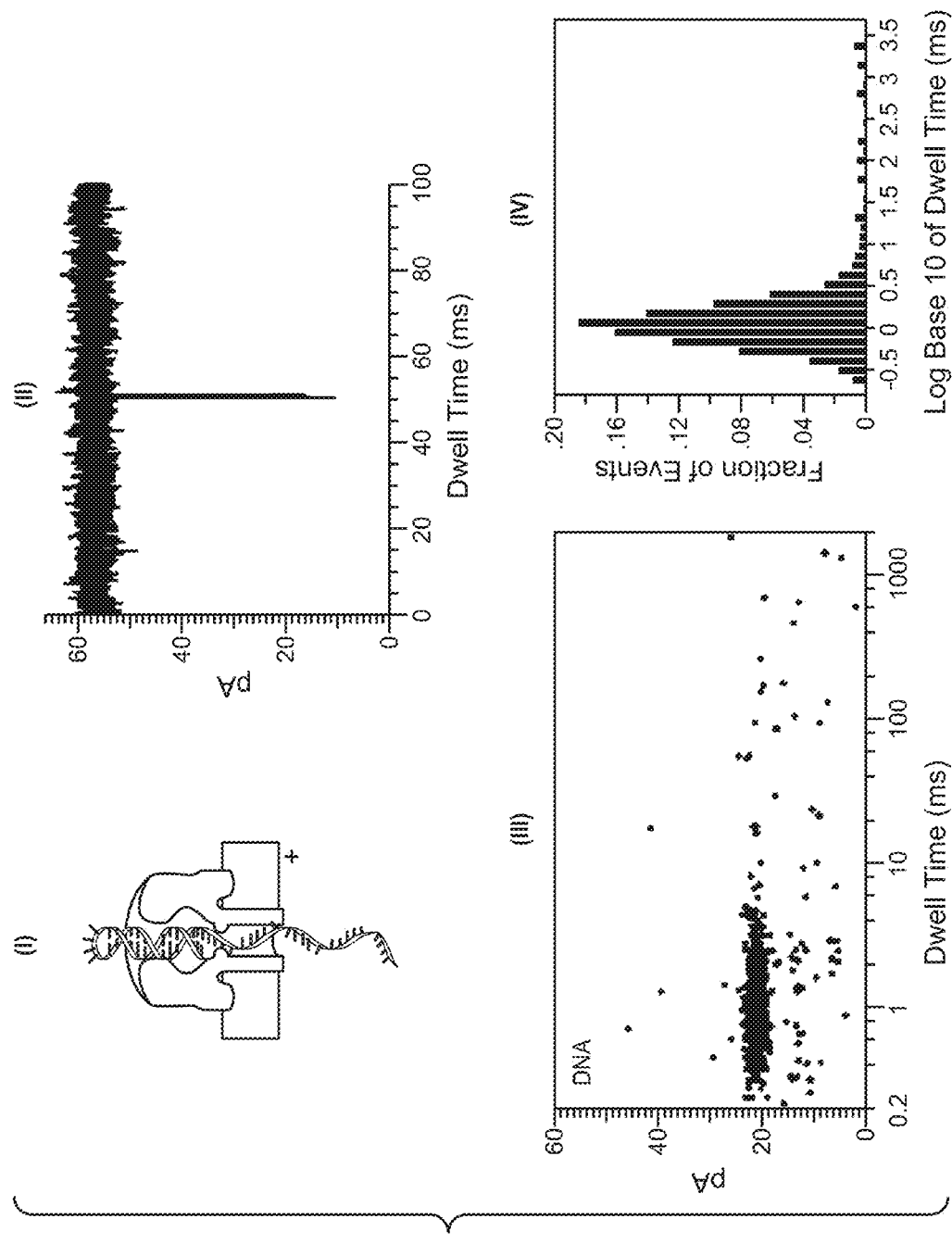
FIG. 9A depicts translocation through the nanopore of DNA alone (14 bp hairpin with a 36 nucleotide 5' overhang and 2'-3' dideoxycytidine terminus, template base at n=0 is C), while translocation of the 14 bphp from complexes with KF, or from complexes with KF and dGTP, are shown in FIGS. 9B and 9C, respectively. For each of FIGS. 9A, 9B and 9C, a diagram of the nanopore with the associated complex (I), a current trace (II), and a dwell time event plot (III) are presented. In IV, probability histograms of the base 10 logarithm of dwell time data are shown in solid. Close examination of the event plot in FIG. 9C(III) reveals that most long dwell time events are within 22 to 24 pA. An open bar subset histogram for the events within 22 to 24 pA is overlaid on probability histogram (FIG. 9C(IV)), revealing that the chosen range is dominated by long dwell time events.
Figure 9B:
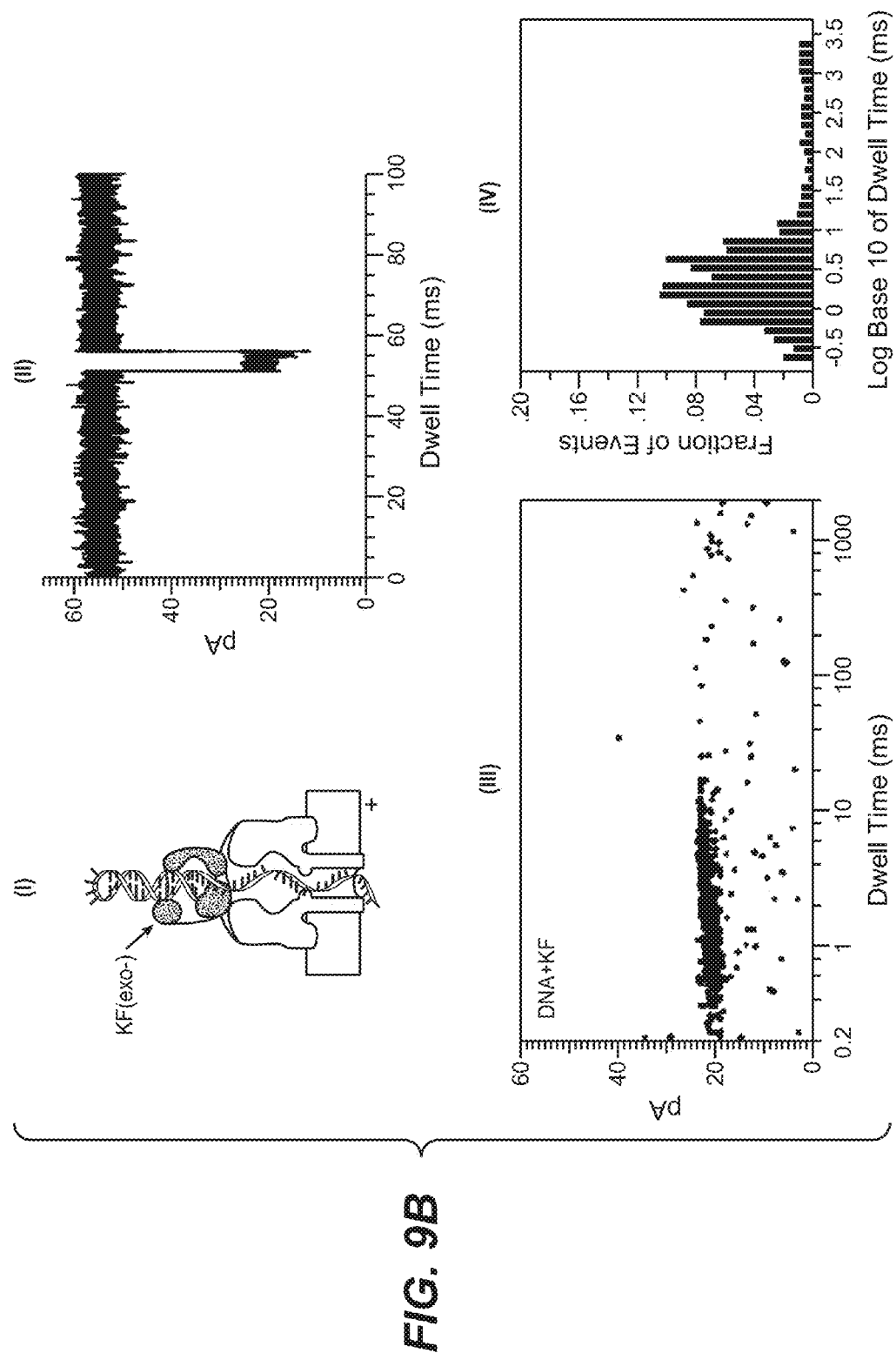
FIG. 9 illustrates means for distinguishing DNA, DNA/KF complexes, or DNA/KF/dNTP complexes in the nanopore device.

Previously (see Benner, et al. (2007) Nature Nanotechnology, 2: 718-724) we have explored the interaction of DNA with the Klenow fragment (KF) of *Escherichia coli* DNA polymerase I. In the absence of KF, capture and subsequent unzipping of 14 bphp at constant 180 mV reveals blockades with 20 pA mean amplitude and 1 msec median dwell time (FIG. 9a). Addition of 2 μM KF yielded a new population of events attributable to binary complexes (DNA/KF) with higher mean amplitude (23 pA), and resulted in an event plot (FIG. 9bII) with a longer dwell time (3 msec median of all events). Addition of 200 μM deoxyguanosine triphosphate (dGTP), the dNTP complementary to the DNA template base in the KF catalytic site, extended the dwell time of the new population to 133 msec median, attributable to a higher stability bond within ternary complexes (DNA/KF/dGTP).

Our tethered DNA configuration described in the next section leverages a significant structural feature exhibited by KF-bound DNA events (with or without the complementary dNTP, that is, binary or ternary complexes), now described. Closer investigation of the binary and ternary complex blockades revealed a two-step pattern in greater than 90% and 97% of the blockades, respectively. The first step has a 23 pA mean amplitude, followed by a brief (1 msec median dwell time) second step, referred to as the terminal step at 20 pA mean amplitude. It was demonstrated that the transition from step one to step two resulted in dissociation of KF (for binary and ternary complexes) from DNA, followed by hairpin dropping into the pore vestibule until translocation occurred. Thus, the terminal step kinetics are precisely the DNA duplex unzipping kinetics.

The consistent presence of the terminal step within enzyme-bound DNA events is mechanistically of importance to our invention. In particular, for an enzyme-bound DNA complex captured in the nanopore under a constant voltage, the terminal step makes it possible to detect in real-time that enzyme has dissociated from the DNA, on the basis of the change in amplitude (from 23 pA to 20 pA at 180 mV in our recent work with KF).

Example X

Detection and Control of DNA and KF-Bound DNA in a Nanopore

In this approach, the voltage control logic is programmed using a finite state machine (FSM) within the LabVIEW 8 software, and the FSM logic is implemented on a field-programmable gate array (FPGA) hardware system. Our first implementation of FSM/FPGA voltage control demonstrated efficient automated detection of individual ternary complexes, based on the characteristic 23 pA amplitude and a dwell time of at least 20 msec. For all events that remained within the threshold range of 21.2-26.8 pA for 20 ms, the voltage was reversed to expel the complex back into the cis chamber, rather than waiting (>100 msec median dwell time) for dissociation of enzyme and DNA translocation to the trans side. The control logic had the effect of concentrating the dwell time of the detected ternary complex events, from a median dwell time of 123 msec (235 msec interquartile range (IQR)) without FSM/FPGA control, to a median dwell time of 23 msec (0.3 msec IQR) with FSM/FPGA control. Since less than 2% of DNA and binary events were longer than 20 msec, the waiting period of 20 msec ensured that nearly all controlled events were ternary complexes.

In our second implementation of FSM/FPGA voltage control, we demonstrated efficient automated detection of individual DNA complexes (no KF enzyme present in cis-chamber), based on the characteristic 20 pA amplitude (Wilson et al. (2008) Rapid finite state machine control of individual DNA molecules in a nanopore. In International Conference on Biomedical Electronics and Devices (BIO-DEVICES), to appear, Madeira, Portugal). For all events that fell within a threshold range of 20+2.8 pA, the voltage was promptly reduced to extend the DNA dwell time. In a second experiment, for all DNA events that fell within a threshold around the 20 pA level, the voltage was promptly reversed to expel the DNA back into the cis chamber prior to translocation. Both implementations (detecting and reacting to enzyme-bound DNA events and detecting and reacting to enzyme-free DNA events) were foundational achievements, and prompted us to attempt to detect and discern between both types of events individually, and in real time.

Example XI

Equipment

A patch-clamp amplifier, Molecular Devices AxoPatch 200B, regulates the applied voltage and measures the ionic current through the channel. The data are recorded using the Molecular Devices Digidata 1440A digitizer, sampled at 50 kHz and low-pass filtered at 5 kHz with a four-pole Bessel filter. One of our stations uses a different patch clamp, the A-M Systems Model 2400.

Example XII

Control Logic: Hardware and Software

The voltage control logic is programmed using a finite state machine (FSM) within the LabVIEW 8 software. The FSM logic is implemented on a field-programmable gate array (FPGA) hardware system, National Instruments PCI-7831R. An FPGA is a reconfigurable hardware platform that permits fast measurement and voltage reaction times (1 μsec output sample time). An FSM is a logic construct in which program execution is broken up into a series of individual states. Each state has a command associated with it, and transitions between states are a function of system measurements. Measurements of the pore current are processed and passed to the FSM as inputs. Changes in the FSM control logic are made as necessary, without the need to re-compile and re-route the design to run on the FPGA. This achieves a balance between speed and flexibility, by enabling the system to react to events on the order of a microsecond, while also allowing for the control logic to be reconfigured as necessary between experiments.

Example XIII

Filtering and Thresholding Ionic Current

Our control logic requires efficient detection of ionic current blockades (events) that result from DNA alone or KF-bound DNA. Further, the logic must be able to efficiently distinguish between these two event types. At 180 mV, mean amplitudes for DNA alone and KF-bound DNA are 20 pA and 23 pA, respectively; a difference of 3 pA. To distinguish DNA alone from KF-bound DNA events in real time, the incoming current signal on the FPGA is filtered and thresholded.

Threshold levels are determined a priori, by constant voltage experiments with the biological components to be detected in the cis chamber. In our experiments with KF, amplitude thresholds consistent with KF-bound or KF-free event amplitudes were identified at 180 mV and 150 mV. At 180 mV, for example, the threshold identified and used to detect DNA alone events was 20±2.8 pA; the threshold identified and used to detect KF-bound DNA events in was 24±2.8 pA. In our experiments to date, one or two thresholds have been implemented at a time. In future work, more than two thresholds may be utilized at the same time, to distinguish multiple macromolecular states that are known to differ based on the attenuated amplitude.

Filtering is used to mitigate noise. Since the ionic current peak-to-peak noise routinely exceeds 3 pA at 180 mV, DNA alone and KF-bound DNA events would not be reliably distinguishable by monitoring the raw current amplitude. By filtering the current amplitude, we have demonstrated detection of DNA alone events and KF-bound DNA events in real time. A windowed mean filter has been used in our experiments so far, including in our initial demonstration shown in the Examples above. Recently, a superior exponentially-weighted mean filter was identified and will be used in new experiments. Details on the two filters are given below.

Example XIV

Moving Average Filter

Every 5.3 sec, the FPGA samples the ionic current and computes a windowed mean amplitude, using a window size of 0.75 msec. If the mean enters a chosen threshold range, the FPGA detects entry and continues to monitor the mean, re-checking the threshold every 0.2 msec. If the mean remains within the threshold range for four consecutive checks, the FSM logic diagnoses the blockade as an event type known to be consistent with the chosen threshold.

In the absence of a change in voltage, the expected time delay between the start of an event and diagnosis of an event is 1.35 msec; 0.75 msec for the windowed mean to first enter the threshold, and 0.6 msec for three more confirmed tests. In practice, the diagnosis time ranges from 1.1 to 2.5 msec. The mean filter was implemented in our invention's initial demonstration (detailed below).

Example XV

Exponentially-Weighted Moving Average Filter

Through post-experiment analysis, our mean filter was shown to falsely detect terminal steps within ternary events. Specifically, the FSM/FPGA was programmed to detect ternary level amplitudes, wait until the terminal step, and upon detection of the terminal step, reverse the voltage to expel the unbound DNA into the cis chamber. Examination of the data showed voltage reversal for many events in which no terminal step was clearly present, although the presence of terminal steps in ternary events is high (97%) with no voltage reversal.

To improve the FSM's robustness to false detections of terminal steps, an exponentially-weighted moving average (EWMA) filter is now being explored to replace the mean filter. The EWMA filter represents a digital implementation of an analog RC filter commonly used for signal smoothing in electrical engineering applications. The filter calculates a moving average that places exponentially less significance on past samples and allows the filtered signal to better track the real signal. EWMA filtering also performs signal smoothing more efficiently than a simple moving average due to its recursive implementation:

$$\bar{i}(t)=(1-\alpha)i(t)+\alpha\bar{i}(t-1), \quad (1)$$

where i and $\bar{i}$ are unfiltered and filtered current signals, respectively, and t is the sample number. Filtering the data from the terminal step detection experiments offline, with α=0.9, showed a substantial improvement in robustness to false positives over the mean filter. As with the mean filter, four consecutive threshold tests will be used for event diagnosis, waiting 0.2 msec between threshold tests.

In the absence of a change in voltage, the expected time delay between the start of an event and diagnosis of an event is 0.7 msec; 0.1 msec for the EWMA to first enter the threshold, and 0.6 msec for three more confirmed tests. More rigorous evaluation of EWMA detection times will be part of our ongoing work.

Example XVI

Time Scales for Changing the Voltage Field Force

When the magnitude of the voltage across the membrane changes, a capacitive transient is superimposed on the measured ionic current. The transient is present in all alpha-hemolysin nanopore studies that involve voltage change (see, for example, Bates et al. (2003) supra), and necessarily masks some information in the measured current for a defined and manageable segment of each event. In our invention, the transient implies that, when the control logic is programmed to diagnose an event type after a voltage change, the filtered current amplitude will not enter a chosen threshold(s) for event diagnosis until the transient has sufficiently settled.

The settling time for the transient is proportional to the net change in voltage. In the voltage control experiment, the changes in applied voltage are from 180 mV to −50 mV, and −50 mV to 180 mV. For a net change of 230 mV (absolute value), we observe that 98% of transients have sufficiently decayed for accurate thresholding after 2.5 msec. In our initial tethered DNA experiments, voltages changes were 200 mV and 170 mV (absolute value). Transients resulting from voltage changes are observable in FIGS. 12-13.

In the presence of a change in voltage, the time required for diagnosis of an event (as a DNA event or an enzyme-bound DNA event) is expected to match the voltage transient settling time. This is because the transient settling time is typically longer than the time required for the filtered amplitude to converge onto the measured ionic current signal. Thus, diagnosis time is expected to be at most 2.5 msec for voltage changes of 230 mV (absolute value), and less than 2.5 msec for smaller voltage changes.

Example XVII

Tethered DNA Configuration

In our initial tethered DNA experiments, a single DNA 20 bphp was captured in the pore, tethered, and threaded back and forth through the pore under voltage control for repeated KF binding and unbinding to the ss-ds junction in the cis chamber. In the experiment, 1 µM 100mer DNA, 5 mM $MgCl_2$, 2 µM KF, and 200 µM of dGTP were present in the cis well of the pore. Thus, each event results from DNA alone or a ternary complex captured in the nanopore.

The DNA oligomer is designed for tethering. Specifically, the 3' end is formed into a 20 base pair hairpin, and 2 µM of 20mer primer complementary to the 5' end is present in the trans chamber. Upon capture of the 5' end, voltage is reduced to hold the DNA in the pore, but not unzip the 3'-end hairpin in the vestibule (if an unbound DNA molecule was captured) or dissociate KF/dGTP from the ss-ds junction (if a ternary complex was captured). After a sufficient time period, the 20mer primer anneals to the 5' end, creating a 20mer duplex on the trans side of the pore. Details of our experiments are provided.

Figure 10:
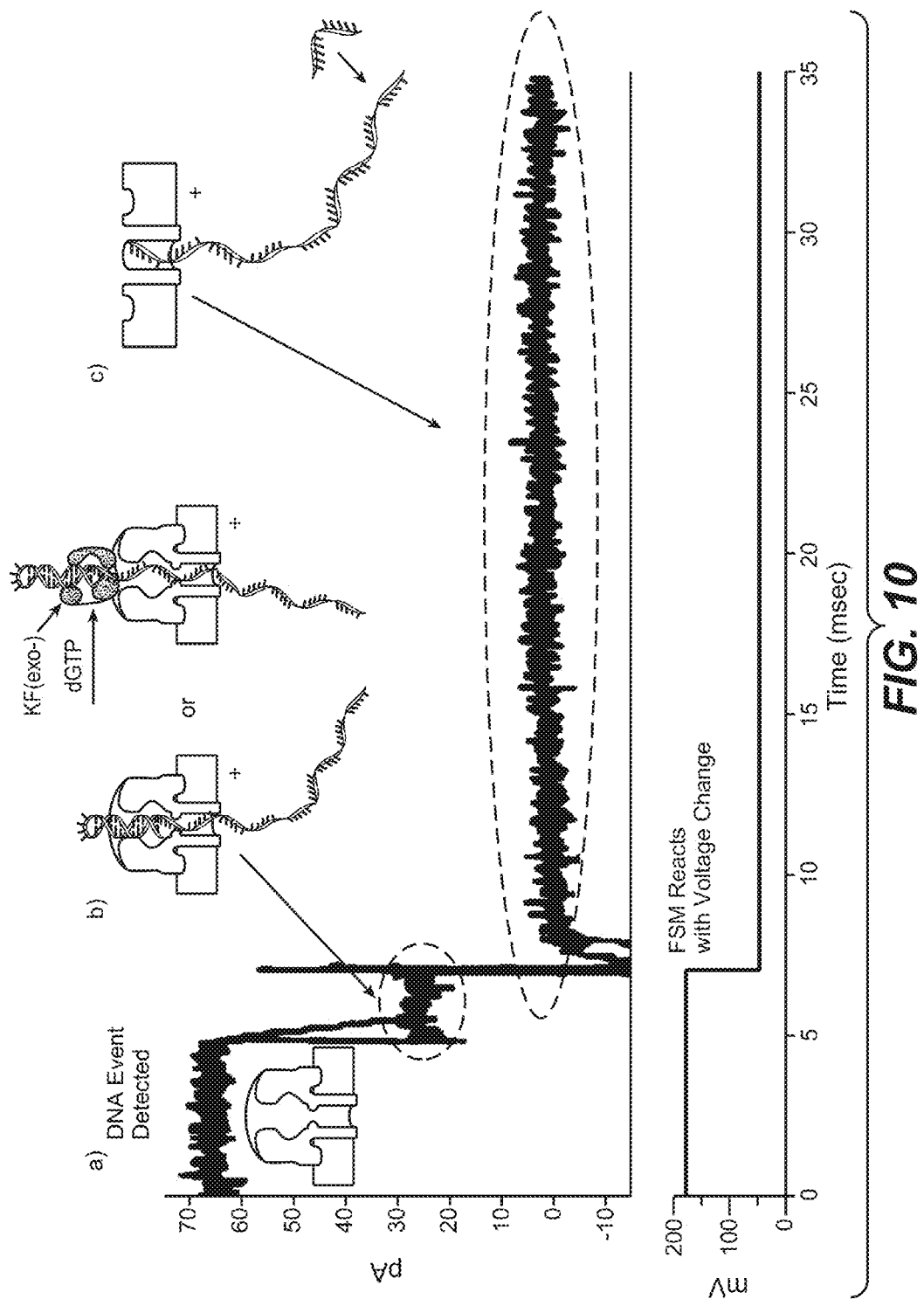
FIG. 10 illustrates tethering of a captured DNA oligomer by annealing a trans-side primer. (a) The finite-state machine (FSM) monitors the open channel current for translocation events. (b) Captured molecule causes the current to attenuate, and the FSM diagnoses an event (DNA or DNA/KF/dGTP) based on the threshold [15.75, 26.75] pA. (c) Upon event diagnosis, the FSM reduces the applied voltage to 50 mV for 20 sec, during which time the 20mer primer anneals to the 5' end. The graphic shows a close up of the lower half of nanopore, with the 5' end and 20mer primer in the trans chamber.

In the experiment, 180 mV applied voltage was used to capture each DNA molecule in the pore with the 5' end translocating into the trans chamber. When a DNA event (threshold of [15.75, 21.25] pA) or a KF-bound DNA event (threshold of [21.25, 26.75] pA) was diagnosed using the mean filter, the FSM reduced the potential to 50 mV, to hold the molecule in the pore but not unzip the hairpin or dissociate KF/dGTP. The 50 mV hold voltage was applied for 20 sec, a period sufficient for the 20mer primer to anneal to the 5' end of the DNA in the trans chamber. The initial tethering phase of a captured DNA molecule is shown in FIG. 10.

After 20 sec, the FSM reversed the voltage to −20 mV, forcing the DNA toward the cis side of the pore with enough force to abut the 5' duplex against the trans-side end of the channel, and dangle the ss-ds junction of the 3' end hairpin into the cis chamber. The −20 mV voltage was found to be small enough to not unzip the 5'-end primer duplex. The amount of time at the −20 mV voltage is referred to as the fishing time $t_{fish}$, measured in seconds. Application of −20 mV for tfish seconds is referred to as the fishing mode of the control logic.

After $t_{fish}$=5 seconds at −20 mV, the FSM changed the voltage to 180 mV, then monitored (thresholded) the mean filtered amplitude to diagnose the identity of the molecule in the pore as either DNA alone or enzyme-bound DNA. If unbound DNA was diagnosed ([15.75, 21.25] pA threshold), voltage was revered to −20 mV to restart the fishing mode. Otherwise, the FSM continued to monitor the filtered amplitude. Within a KF/dGTP-bound event, upon diagnosis of the terminal step ([15.75, 21.25] pA threshold), voltage was reversed to −20 mV to restart the fishing mode.

Figure 11:
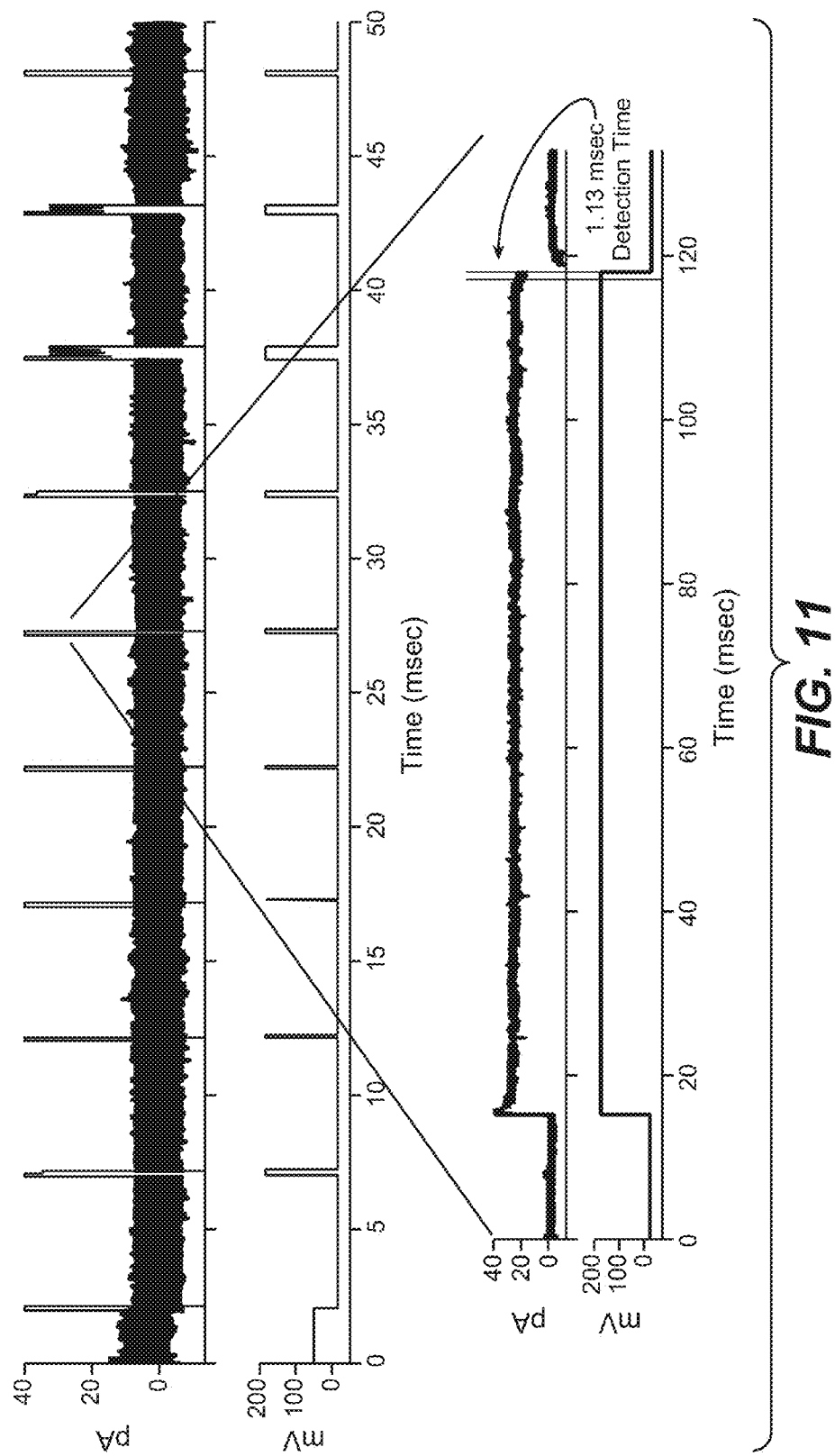
FIG. 11 illustrates a time course of ionic current signal in tethered DNA experiment. First 2 seconds shows the end of the 20 sec tethering waiting period (50 mV applied) for 5'-end primer to anneal in trans chamber. Fishing time of $t_{fish}$=5 seconds used, with nine probe events shown. Probe event number 5 is blown-up to show details of an enzyme-bound event, with terminal step and subsequent terminal step diagnosis after 1.13 msec. Since enzyme-bound events last ~100 msec, the control logic is primarily in fishing mode in this experiment.

Application of 180 mV until unbound DNA is diagnosed (by DNA alone or by reaching the terminal step of an enzyme-bound event) is referred to as the probing mode of the control logic. The first nine fish-then-probe actions within a tethered DNA experiment are displayed in FIG. 11. Once the DNA is tethered, and the FSM logic begins the fish-then-probe cycle, only the unbound DNA threshold is used for diagnosis, of unbound DNA or of a terminal step within and enzyme-bound DNA event. The FSM logic repeats the fishing mode then probing mode cycle until the tethered DNA molecule translocates through the pore, and the open channel current is detected. DNA translocates if the 3'-end hairpin is unzipped or if the 5'-end duplex is unzipped. We expect that DNA translocation is most likely to occur by unzipping the 3'-end hairpin, since unzipping at 180 mV can happen faster than DNA event diagnosis. The −20 mV voltage, on the other hand, is less likely to unzip the 5'-end duplex, even for fishing times on the order of minutes. Post experiment analysis can be used to determine the frequency of DNA translocation in probing mode versus fishing mode. When the tethered DNA translocates and current returns to the open channel value, the FSM resets and monitors the current for another event to tether a new DNA molecule.

Figure 12:
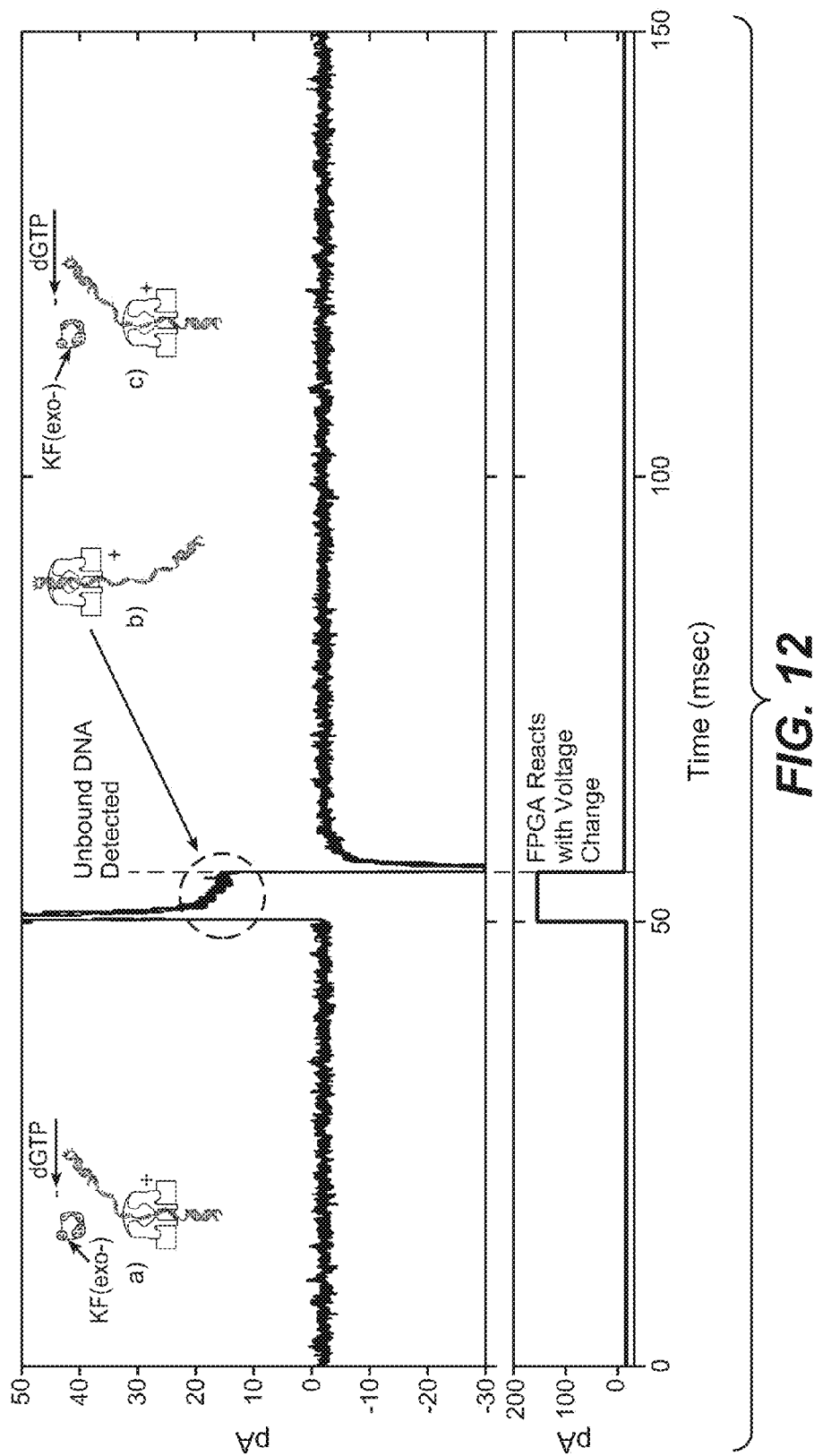
FIG. 12 illustrates fishing and probing of tethered DNA molecule in a nanopore. (a) Fishing mode, with $t_{fish}$=0.521 sec. (b) Probing mode, in which the FSM applies 150 mV until a DNA alone event is diagnosed with threshold [7.5, 15.5] pA. In the event shown, DNA alone is diagnosed as soon as the transient settles, with no enzyme bound to the DNA, and the fishing mode is restarted. (c) Fishing mode.
Figure 13:
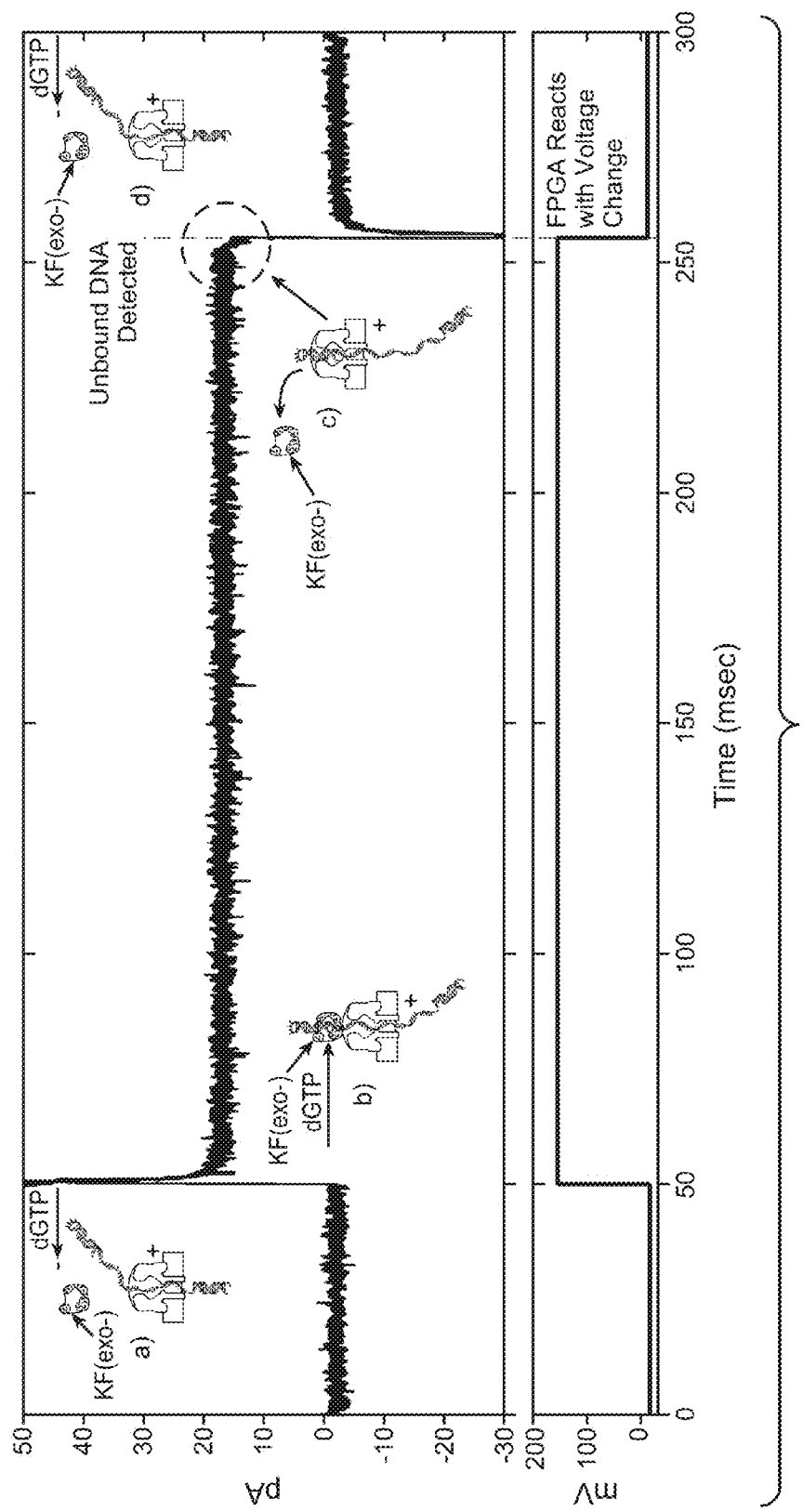
FIG. 13 illustrates another method for fishing and probing of tethered DNA molecule in a nanopore. (a) Fishing mode, with $t_{fish}$=0.521 sec. (b) Probing mode, in which the FSM applies 150 mV until a DNA alone event is diagnosed. In the event shown, enzyme-bound DNA is diagnosed, and the FSM continues to monitor the filtered amplitude. (c) The terminal step is diagnosed, using the [7.5, 15.5] pA threshold, and the fishing phase is restarted. (d) Fishing mode.

In a second experiment a lower capture and probing voltage of 150 mV was used, and a faster fishing time of $t_{fish}$=0.521 seconds was used. Based on experiments with DNA alone and DNA with KF and dGTP at constant 150 mV, the unbound DNA threshold was set to [7.5, 15.5] pA and the KF/dGTP-bound DNA threshold was set to [19, 27] pA. Fishing and probing modes are shown in FIG. 12, where probing reveals a DNA alone event. Fishing and probing modes are shown again in FIG. 13, where probing reveals an enzyme-bound DNA event. The FSM captured and tethered eight independent DNA molecules. In total, 337 enzyme-bound DNA events occurred in probing mode over a time period of 380 seconds. Analysis of the data shows the FSM/FPGA correctly diagnosed the terminal step in these events 72% of the time. In the remaining 28%, fishing was restarted before a terminal step actually occurred in the enzyme-bound DNA event (referred to as a false positive). Offline analysis showed that the EWMA filter resulted in zero false positives in this data. Online implementation of the EWMA filter in future tethered DNA experiments will be used to gauge and improve the robustness of the filter to false positives. An "unbound-DNA check" mechanism can be explored to rule out/minimize false positives. The mechanism works as follows: at the end of each probing mode, fish for a period too short to expose the ss-ds junction in the cis-chamber, then re-probe to ensure the DNA is unbound; if unbound, being fishing for period $t_{fish}$; if bound, wait until terminal step detected. Identification of the brief fishing period used to confirm that the DNA is unbound will be part of our ongoing work.

Example XVIII

Rapid Detection and Control to Probe Individual DNA and Enzyme-Bound DNA Molecules in a Nanopore In the biological nanopore setup, a planar lipid bilayer is created across a 20 µm TELON aperture in a KCl solution. A single α-hemolysin protein channel is inserted into the planar lipid. The channel (pore) is 15 nm in length and varies in diameter. The cis-opening of the pore is 2.6 nm wide, opening to a 3.6 nm vestibule before narrowing to a limiting 1.5 nm width at the beginning of the stem. The remainder of the stem up to the trans-opening is 2 nm wide. The vestibule is large enough for double-stranded DNA (dsDNA) to enter, but the limiting stem is just wide enough for ssDNA to pass through. Across the bilayer, AgCl electrodes are used to apply a potential that produces an ionic current through the pore (FIG. 7). The field created by this voltage pulls the negatively charged phosphate backbone of the ssDNA or RNA through the pore, passing from the cis side to the trans side of the pore with the trans-side voltage positive. As molecules translocate, the pore becomes partially blocked by the translocating molecule, causing a momentary drop in current. These translocation events can be characterized by the amplitude of the blockade current and the time the molecule spends in the pore, defined as the dwell time. The DNA used in the experiments presented here are comprised of ssDNA and dsDNA segments. Specifically, for the non-FPGA experiments disclosed herein, a 14 base pair hairpin (14 bphp) 67 nucleotides in total length was used. For the rest of the experiments, a DNA oligomer that is 79 nucleotides total in length, with a 20 bphp was used. The hairpin was formed by folding the 3' end over itself, creating 14 or 20 base pairs. The hairpin is thus the double-stranded segment, with the single-stranded segment 35 nucleotides long for both the 14 and 20 bphp (4 unpaired bases in the doubled-stranded end loop). Upon capture of the ssDNA end, the hairpin enters the pore vestibule and remains until the hairpin is unzipped. A schematic of the nanopore system and an example 20 bphp translocation event is illustrated in FIG. 8.

Correlations between the ionic current amplitude and features of individual DNA or RNA molecules translocating through the pore has been shown through various assays using α-hemolysin nanopores. A near direct correlation between the number of molecules passing through the pore and the number of current drops has been demonstrated. Homopolymers of ssDNA and block copolymers of RNA are also distinguishable based on the measurable differences in the blockade current amplitude or kinetics. However, translocation rates are too fast (up to 2 nucleotides/p sec) for sequencing individual nucleotides in heterogeneous single-stranded polymers using existing biological nanopores. Here and in other studies, DNA with single and double stranded segments is used to increase the dwell time of nucleotides in the pore (0.5-5 msec, depending on applied voltage and dsDNA segment length). For example, blunt-ended hairpins, those with no single-stranded overhang, ranging from 3 to 9 bases long are used in Vercoutere et al (2001; Nat. Biotechnol, 19(3): 248-252, and Vercoutere et al. (2003) *Nucleic Acids Research*, 31: 1311-1318), where machine learning methods were applied to the extended dwell time events to identify (sequence) the terminal base pair made up of the 3' and 5' ends of the ssDNA.

Example XIX

Voltage Control Using FSM/FPGA

The nanopore system is setup in a 0.3 mM KCl solution. A patch-clamp amplifier, Molecular Devices AxoPatch 200B, regulates the applied voltage and measures the ionic current through the channel. The data are recorded using the Molecular Devices Digidata 1440A digitizer, sampled at 50 kHz and low-pass filtered at 5 kHz with a four-pole Bessel filter.

The voltage control logic is programmed using a FSM within the LabVIEW 8 software. The FSM logic is implemented on a field-programmable gate array (FPGA) hardware system, National Instruments PCI-7831R. An FPGA is a reconfigurable hardware platform that permits fast measurement and voltage reaction times (1 µsec output sample time). An FSM is a logic construct where program execution is broken up into a series of individual states. Each state has a command associated with it, and transitions between states are a function of system measurements. Measurements of the pore current are processed and passed to the FSM as inputs. Changes in the FSM control logic are made as necessary, without the need to re-compile and re-route the design to run on the FPGA. This achieves a balance between speed and flexibility, by enabling the system to react to events on the order of a microsecond, while also allowing for the control logic to be reconfigured as necessary between experiments.

Example XX

FSM Monitoring of Mean Filtered Current for DNA and Enzyme-Bound DNA Event Diagnosis Blockade events, quantified by the blockage current and dwell time, can be detected and monitored in real time using the FSM/FPGA. A mean filter applied to the incoming current signal on the FPGA removes a large portion of the peak-to-peak noise. Specifically, every 5.3 µsec, the FPGA samples the ionic current and computes a windowed mean amplitude. The FPGA tests if the mean is within a pre-specified range and then continues to test the mean every 0.2 msec after initial detection. If the mean enters and remains within this range for four consecutive tests, the FSM logic diagnoses the blockade as a DNA hairpin event. The time delay between a DNA translocation event and diagnosis of a DNA translocation event is nominally 1.35 msec; 0.75 msec for the windowed mean to first enter the 17.2 to 22.8 pA range, and 0.6 msec for three more confirmed tests, and 0.65 ms of computational delay. The mean filtered current is used for DNA event diagnosis and triggers the transitions between states in the FSM control logic.

The FSM control logic has been used to discern between DNA alone or DNA/enzyme complex using the nanopore system. Additionally, enzyme dissociation from DNA can be detected and reacted to in real time using the FSM to detect the terminal steps present in the current signal. The ability to detect both DNA and DNA/enzyme complex in the pore can permit the real-time identification of the base at the junction between single-stranded and double-stranded DNA when KF is bound to a DNA hairpin and the correct nucleotide is present in the system, as detailed in this report.

Furthermore, the detection and control of single DNA hairpin molecules can be expanded to include repeated capture of KF using a single copy of DNA. One base can be identified when KF is pulled off a DNA hairpin using a nanopore. Repeated capture and dissociation of KF from the same copy of DNA can allow many bases to be sequenced provided a method for single-base ratcheting polymerase reaction is found. Current sequencing methods are limited to read lengths of around one kilobase (1000 base pairs identified), but a nanopore-based sequencing method has potential for much longer read lengths when compared to traditional bulk sequencing methods.

The bulk of the future work is dedicated to improving the detection robustness by increasing the signal-to-noise of the current signal through improved filtering and use of longer DNA hairpins. Also, a double-checking scheme to ensure the enzyme has dissociated will be implemented. Experiments that vary the concentration of KF and dNTP will also be performed to find the detection limit of different complexes.

Example XXI

Detection of Molecular Complexes

Figure 9C:
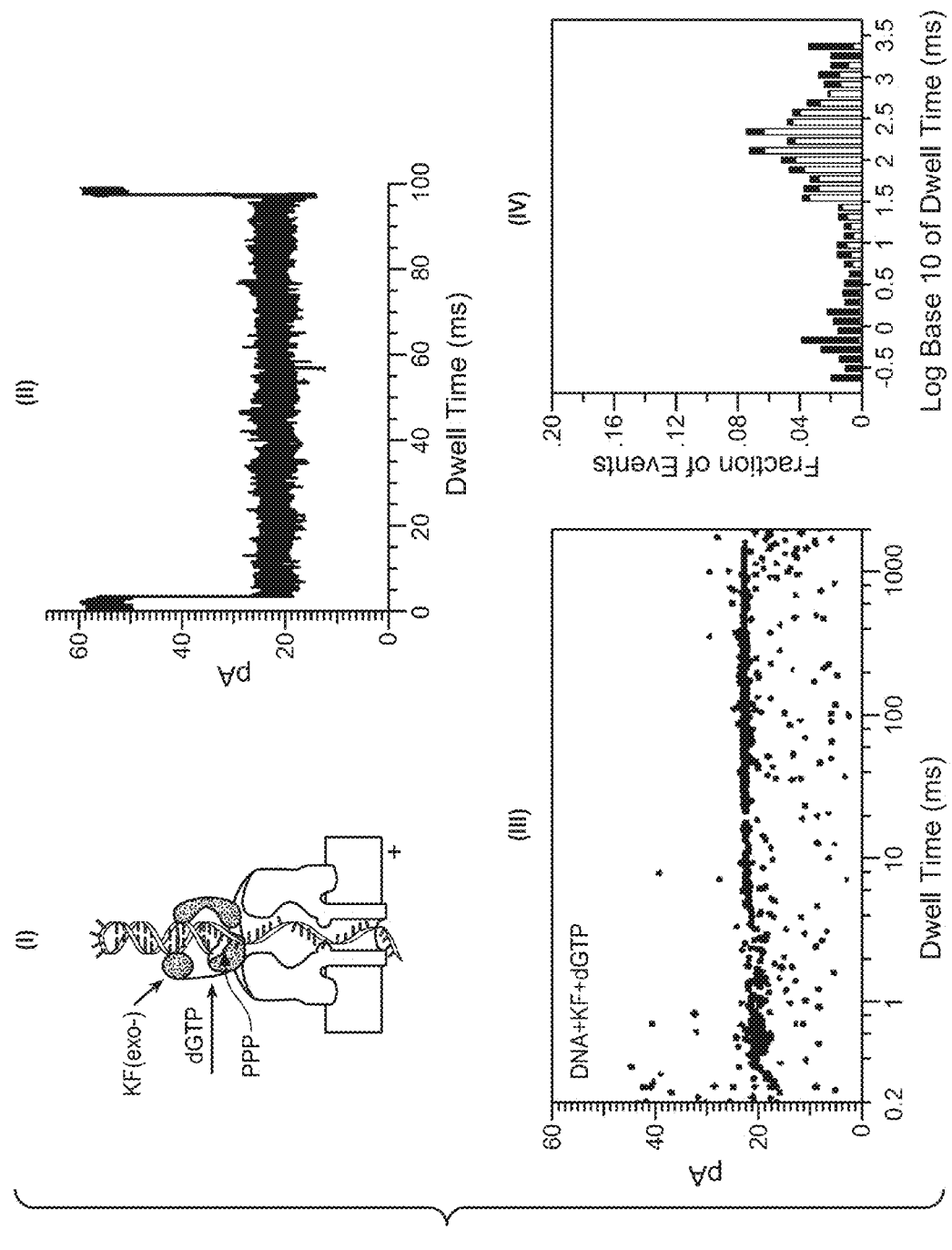
Figure 14A:
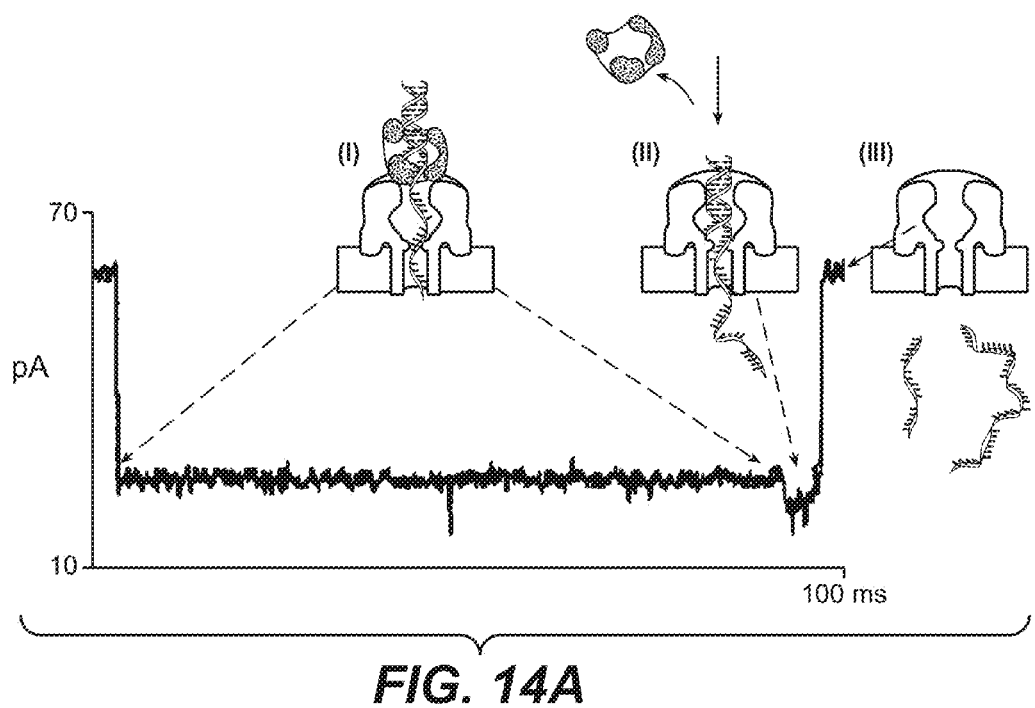
FIG. 14 illustrates a proposed mechanism for translocation of DNA/KF binary complex and DNA/KF/dGTP ternary complex through a nanopore. (a) Shows a typical current trace when ternary complex is present. Parts (a)(i), (a)(ii), and (a)(iii) illustrate the configuration of the system for each section of the signal. (b) and (c) show a dwell time event plot for a 14 bphp alone and the terminal step present in ternary complex events, respectively. The similarity of the dwell times in the two plots supports the perception that the terminal step is a result of KF dissociation. (d) and (e) show the same as (b) and (c) but for a 20 bphp. (f) shows a DNA only event (f)(i) and a DNA/KF binary event (f)(ii) side by side. Note the absence of the terminal step in the DNA only event when compared to the enzyme-bound event.
Figure 14F:
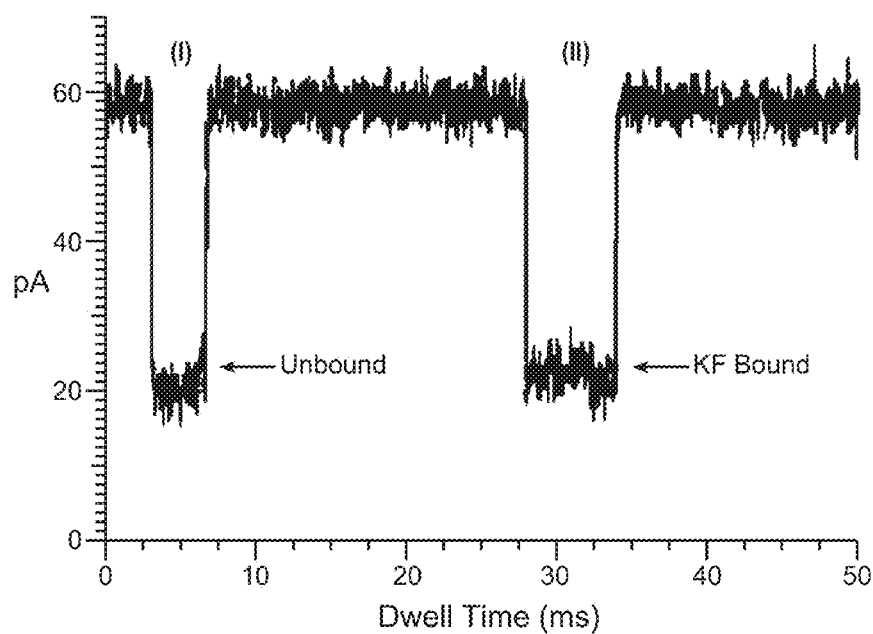
Figure 15A:
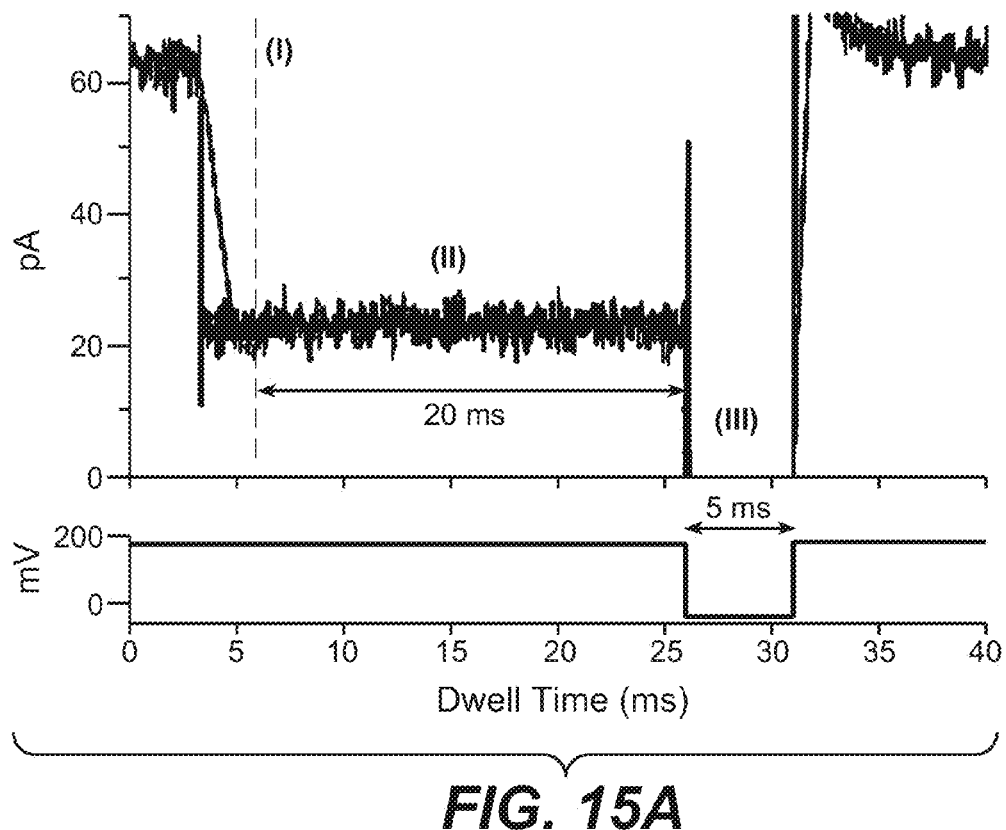
FIG. 15 illustrates a representative ternary complex event under FPGA control. (a)(i) The FPGA diagnosed an enzyme event in the detection range [17.2 pA, 22.8 pA]. a(ii) The FPGA continued to monitor the current to ensure it stayed within the detection range for at least 20 msec. Events lasting longer than 20 msec were diagnosed as a DNA/KF/dGTP ternary complex event. (a)(iii) Upon diagnosis of a ternary complex, the FPGA reversed the voltage to −50 mV for 5 ms, ejecting the complex from the pore. The 180 mV capture voltage was then restored. (b) Dwell time probability histograms for 24±2.8 pA events with FPGA control (527 total events in red) and without FPGA control (155 total events in blue).
Figure 15B:
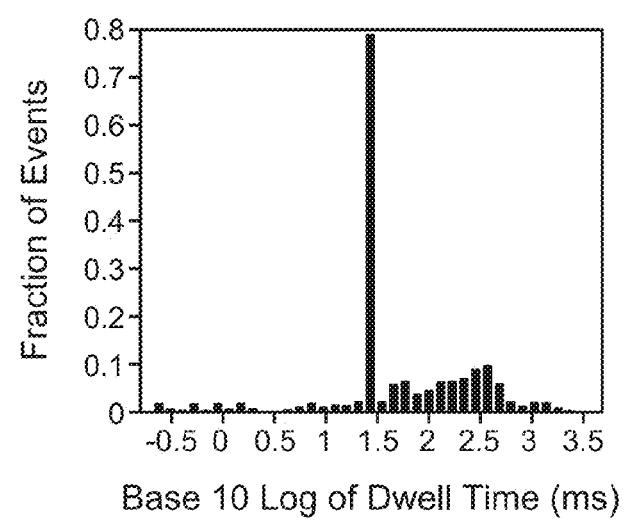

The interaction of DNA with Klenow fragment (KF) of *Escherichia coli* DNA polymerase I can be probed with the nanopore system. In the absence of KF, capture and subsequent unzipping of 20 bphp at constant 180 mV reveals current blockades with 20 pA mean amplitude and 4 msec median dwell time. Addition of KF and the dNTP complementary to the DNA template base in the KF catalytic site yielded a substantial increase in blockade dwell times (110 msec median lifetime for dGTP), attributable to ternary (DNA/KF/dGTP) complexes. Closer investigation of such blockades revealed a two-step pattern in greater than 97% of the blockades, the first step at 24 pA mean amplitude, and the second (terminal) step at 20 pA mean amplitude, lasting 4 ms consistent with the hairpin kinetics alone. It was demonstrated that the transition from step one to two resulted in dissociation of KF from DNA first, followed by the hairpin dropping into the pore vestibule until unzipping occurred. As an initial effort at voltage control of enzyme-bound DNA, efficient automated detection (<3 msec) of individual ternary complexes was demonstrated, based on the characteristic 24 pA amplitude and truncation of the blockade time by voltage reversal after 20 msec. The 20 msec cutoff was used because 60% of events are longer than 20 msec in the presence of the correct dNTP, while only 2% of events are longer than 20 msec and in the detection range absent the correct dNTP, showing that events longer than 20 msec usually correspond to ternary complex events (FIG. 9). Detection was based on the mechanism described in Section 1.2.2 for calculating the windowed mean using the previous 1.5 msec of signal and a detection range of 17.2 to 22.8 pA. The basis for choosing this range is that ~20 pA is the median amplitude for 14 and 20 bphp events at 180 mV as well as the terminal step (FIG. 14).

The ability to diagnose individual events in real time shows potential for extending this system to sequencing. A single long dwell time event (>20 msec) gives high probability of a ternary complex event. Based on the dNTP present in the system, the identity of the next base to be added can be identified, achieving single base sequencing. For multiple base reads, regulation of base polymerization is necessary to step along the addition of nucleotides. For every base added, enzyme-bound DNA present in the pore can be probed for the presence of ternary complex, confirming the correct dNTP is present for polymerization. In the experiments presented here, the dNTPs are di-deoxy terminated so polymerization is stalled, preventing more than a single base addition to the hairpin. This use of di-deoxy terminators is the foundation of most sequencing methods employed today.

Example XXII

Control of Individual DNA Molecules

Rapid detection (<2 msec) is based on computing a filtered mean amplitude, based on the last 0.75 msec of the ionic current, in real time and monitoring the mean relative to an amplitude range consistent with DNA hairpin blockades (20±2.8 pA). Upon detection, two methods of voltage control were demonstrated.

In the first method, dwell time extension is achieved by prompt voltage reduction, with the reduced voltage applied until the hairpin unzips. A higher voltage for capture increases the number of molecules examined, and the reduced voltage post-capture increases the dwell time to, in principle, facilitate sequencing. In particular, extending the life of DNA hairpins in the pore increases the time within which a terminal base identification could be achieved using machine learning methods.

The second method reduces the voltage for a preset time (10 msec) and then reverses the voltage to expel the molecule prior to hairpin unzipping. This demonstrates control authority to aggregate the dwell times of hundreds of blockade events. Additionally, it complements previous work, confirming the ability to detect both DNA-enzyme blockades and DNA hairpin blockades. Confirmation of the ability to discern between each blockade type in real time is crucial to future work. Ultimately, nanopore-based characterization of enzyme dynamics will require direct detection and control of multiple DNA conformations relative to the enzyme, and direct control of enzyme-free DNA is a prerequisite toward developing this capability.

Direct control of ssDNA in a nanopore has been demonstrated, in which detection of DNA is based on monitoring the raw amplitude relative to a threshold level. Voltage level changes, comparable to those employed here, were commanded to explore the zero and low voltage effects on ssDNA-pore interactions. In contrast to thresholding the raw ionic current amplitude, the windowed amplitude mean calculation used here filters the current noise. Additionally, detection depends on the mean remaining within a preset amplitude range (<6 pA in spread) for multiple consecutive comparisons, resulting in fewer false detections (false positives) than a single threshold comparison. This was an unexpectedly superior result.

Example XXIII

Experiments and Results

A demonstration of direct FSM/FPGA control of single DNA molecules in a nanopore is now described. In a first experiment, the objective was to efficiently detect DNA hairpin events, one molecule at a time and increase the blockade dwell time by lowering the applied voltage from 180 mV to 150 mV upon detection. This is referred to as "dwell time extension control". After completing this objective, the aggregation of the extended blockade dwell times was sought by expelling the DNA using voltage reversal of −50 mV after 10 msec at 150 mV. This is referred to as "dwell time aggregation control". The motivation was to increase the nominal hairpin dwell time, but expel the molecule before unzipping the hairpin. A tighter distribution for the aggregated dwell time events, in contrast to the distribution of the extended dwell time events, will indicate that the objective has been met.

Figure 16A:
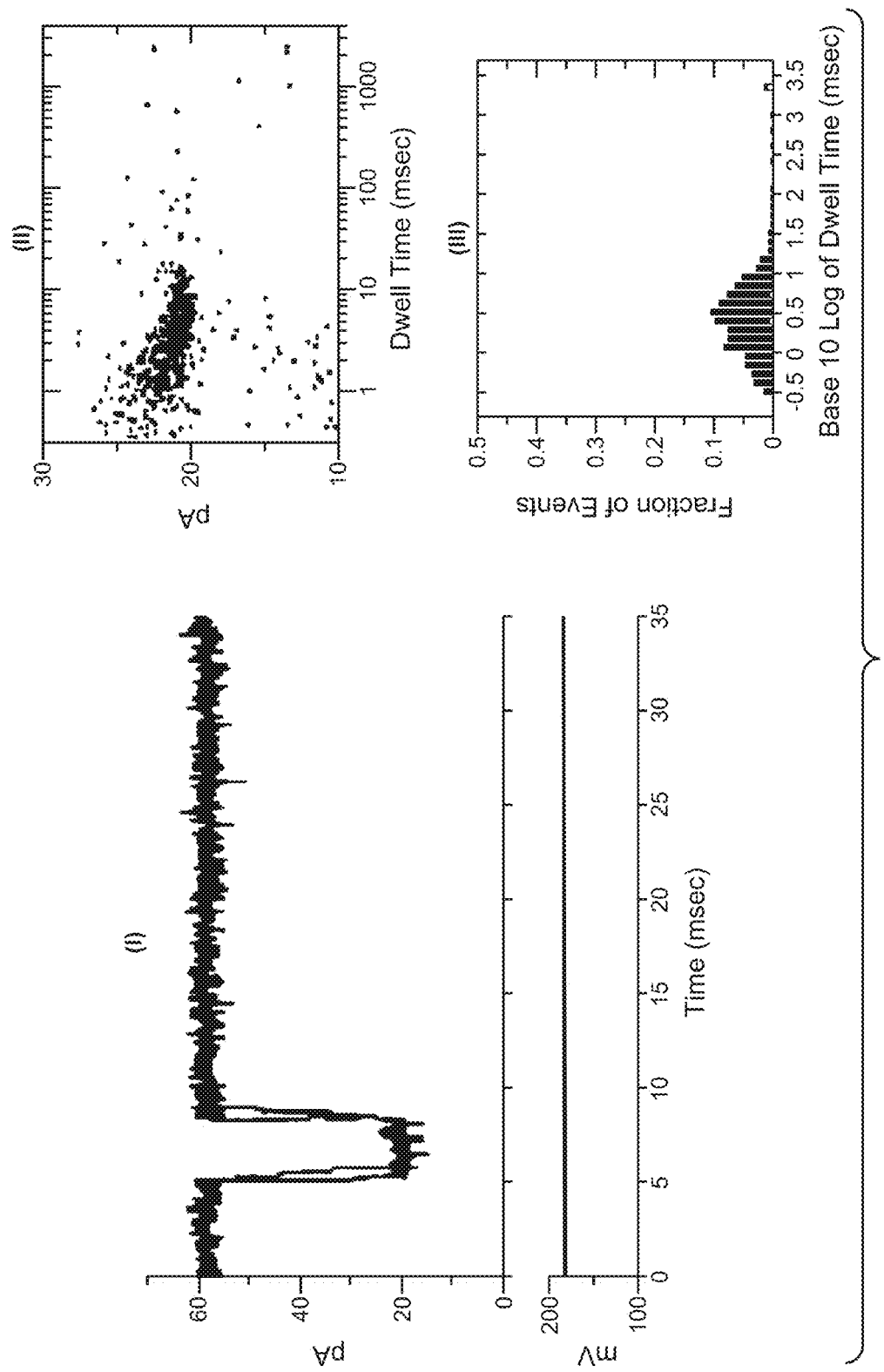
FIG. 16 illustrates regulation of 20 base pair hairpin (bphp) dwell time using FSM control. (I) The red current signals are low-pass filtered at 5 kHz, the blue signal is a mean filtered current, and the red voltage signal is the commanded voltage. Typical events and corresponding voltage signals under (a) constant 180 mV voltage, (b) dwell time extension control, and (c) dwell time aggregation control. (II) Event plot of DNA events, showing average amplitude vs. dwell time for each event. (III) Probability histograms of the base 10 logarithm of dwell time for all events (filled bars), and for subset of events in range 13 to 18 pA (open bars).

A typical 20 bphp event at constant 180 mV voltage is shown in FIGS. 8 and 16aI. The probability histogram of the base 10 logarithm of dwell time (FIG. 16aIII, solid bars) is unimodal, with median dwell time of 2.8 msec. The median amplitude of the event plot in FIG. 16aII is 20.9 pA with an interquartile range (IQR) of 1.7 pA. Only 6% of events are in the subset range of 13 to 18 pA (FIG. 16aIII, open bars). For the same experiment at constant 150 mV voltage (data not shown), the events cluster around a median amplitude of 14.7 pA and 87% of 150 mV events are in the 13 to 18 pA range. Thus, under extension and aggregation control for which the voltage is reduced to 150 mV for all detected events, a larger percentage of blockades should have a mean amplitude within the 13 to 18 pA range.

Example XXIV

Figure 16B:
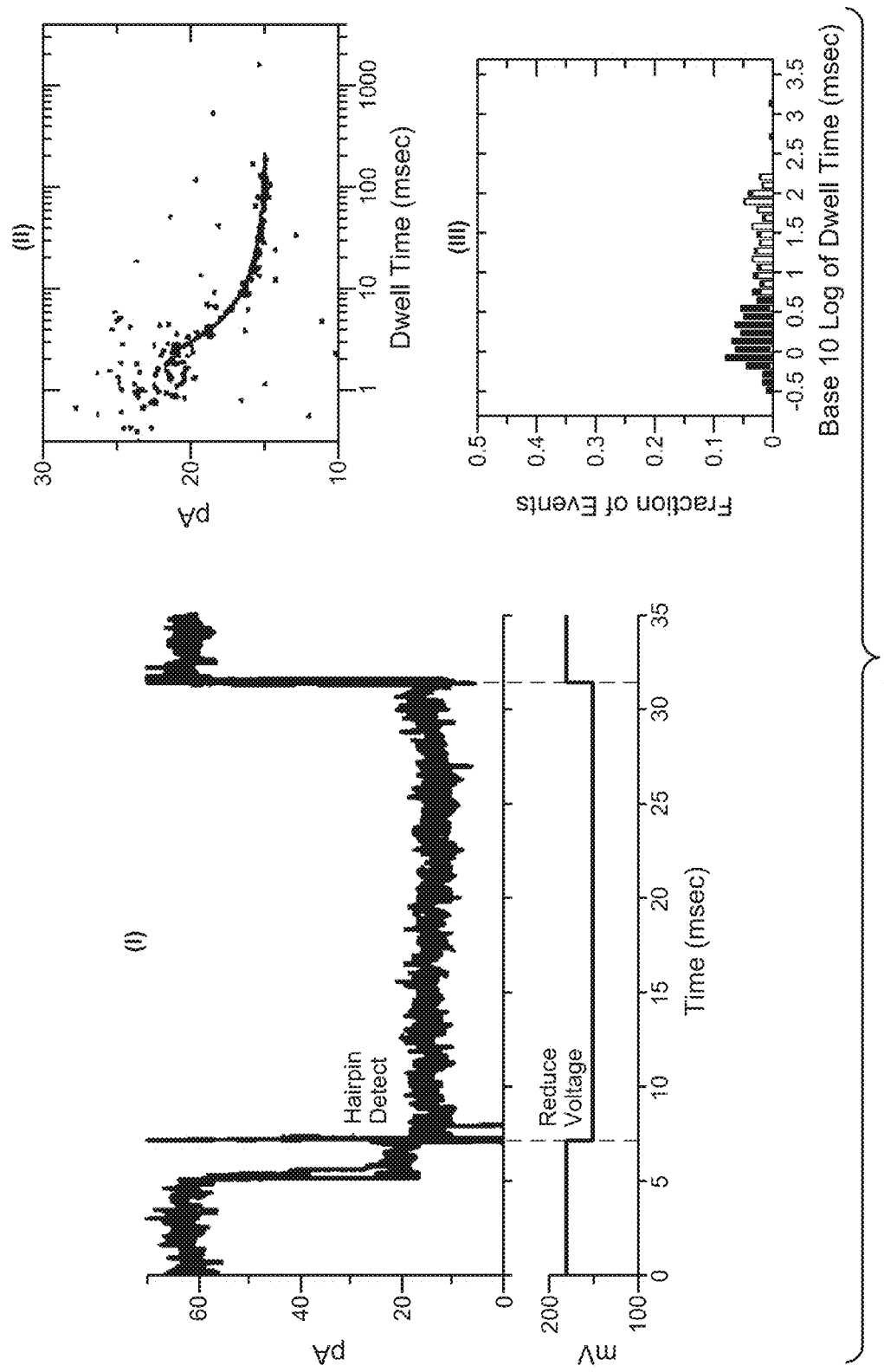

Dwell Time Extension Control (FIG. 16b)

Upon diagnosis of a DNA hairpin event using the mean filtered current, the command voltage is reduced to 150 mV until the hairpin unzips and the DNA translocates through the pore. Using 180 mV for capture results in more events than 150 mV, while reducing to 150 mV extends the life of the hairpin. Again, dwell time extension is useful for sequencing by machine learning methods. The extended time can also be used to increase the likelihood of correctly detecting DNA or DNA-enzyme configurations (states), by increasing the time during which the mean must reside within the amplitude threshold corresponding to each state. After each translocation, the FPGA resets the voltage to 180 mV. A representative event is shown in FIG. 16bI. The event plot (FIG. 16bII) pattern shows that events faster than the nominal diagnosis time of ~1.4 msec are unaffected by extension control, and events with longer dwell times converge to the ~15 pA mean amplitude as expected. The concave trend is also consistent with the mean amplitude computation for each event. In particular, for an event at 21 pA for 1.4 msec and at 15 pA for x msec, an approximate event mean amplitude $\bar{I}$ is $$\bar{I} = \frac{1.4*21 + 15*x}{1.4+x}$$

When x≈24 msec, as in FIG. 16bI, $\bar{I}$=15 pA. The fraction of events within the subset range 13 to 18 pA increased to 41% and is shown in the open bar histogram overlaid on the probability (filled bars) histogram (FIG. 16bIII).

Example XXV

Figure 16C:
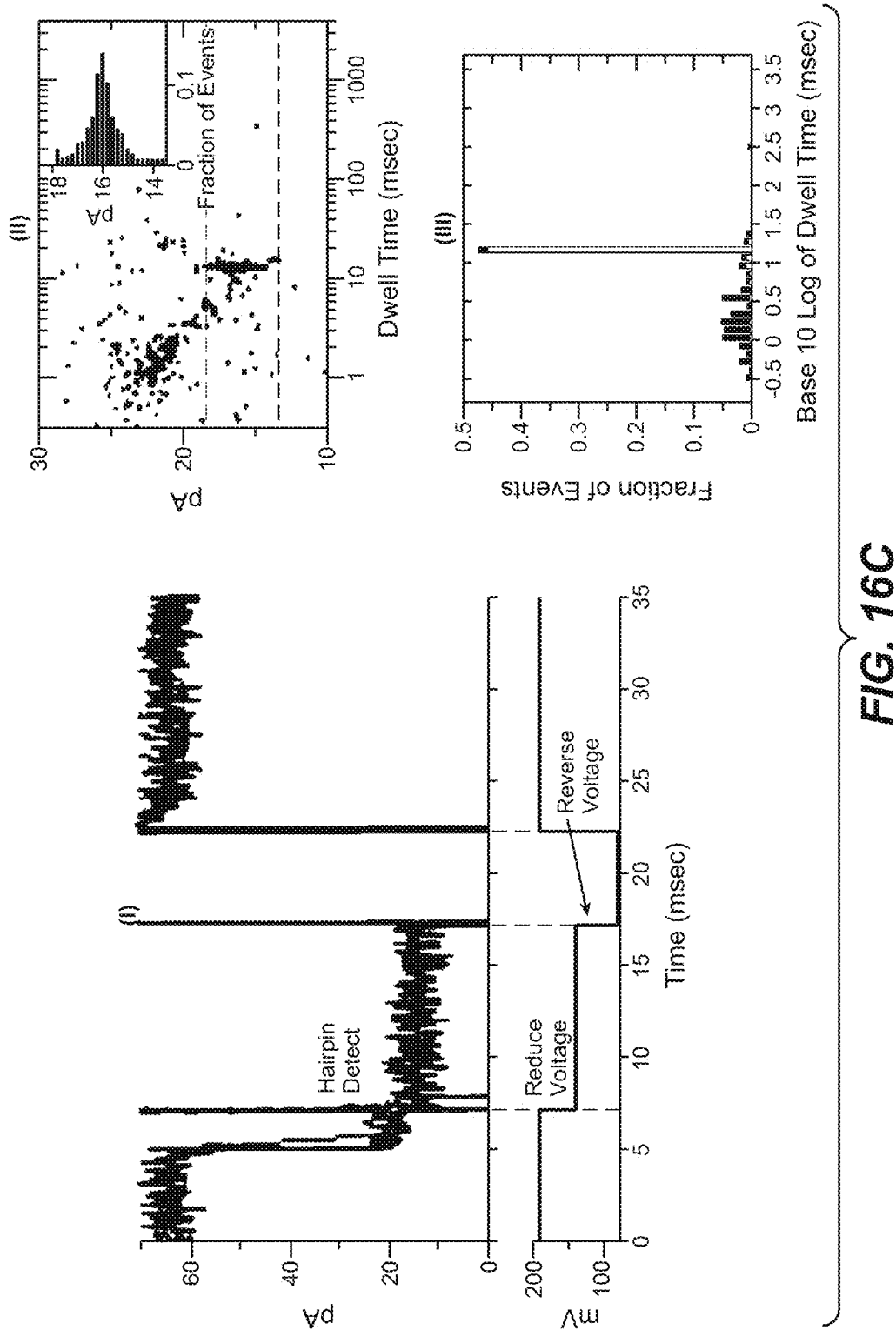

Dwell Time Aggregation Control (FIG. 16c)

The objective was to aggregate the dwell times of the extended events by applying 150 mV for 10 msec upon diagnosis of a hairpin event, followed by voltage reversal of −50 mV for 5 msec. The reversal time of 5 msec is known to sufficiently clear the DNA from the channel, prepping the pore for the next event. The aggregation control would imply a measure of control over the distribution of the events, in addition to control of the individual molecular events. A representative event is shown in FIG. 16cI. As before, the event plot (FIG. 16cII) pattern shows that events faster than the nominal diagnosis time of ~1.4 msec are unaffected by aggregation control. Using the previous equation, for an event at 21 pA for 1.4 msec and at 15 pA for 10 msec, the approximate event mean amplitude is $\bar{I}$=16 pA. Within the subset range of 13 to 18 pA, the median is 16 pA with 0.7 pA IQR, precisely the approximate mean calculation. The fraction of events within the subset range 13 to 18 pA increased to 55%, shown in the open bar histogram overlaid on the filled bar probability histogram (FIG. 16cIII). For the subset of events, a median dwell time of 12.4 msec is commensurate with a brief delay, required to diagnose hairpin state, plus 10 msec extension time. An IQR of 0.1 for the open bar subset histogram indicates that the aggregation objective has been achieved. Regarding the impact of control on the distribution of events, 43% of all events in FIG. 16cII fall within the dwell time range of 12-13 msec and the amplitude range of 13-18 pA.

Example XXVI

Tethered DNA

Preliminary experiments were run with KF bound to a 20 base pair DNA hairpin (20 bphp). A single 20 bphp is threaded back and forth through the pore such that KF binds with the DNA multiple times. In this experiment, 1 μM 100mer ssDNA, 5 mM MgCl$_2$, 2 μM KF, and 200 μM of dGTP were present in the cis well of the pore. The ssDNA oligomer was designed such that a 20mer hairpin forms on the 3' end. On the trans side, there was 2 μM of a 20 base pair (20mer) primer complementary to the sequence at the 5' end of the DNA hairpin in the cis side.

Figure 17A:
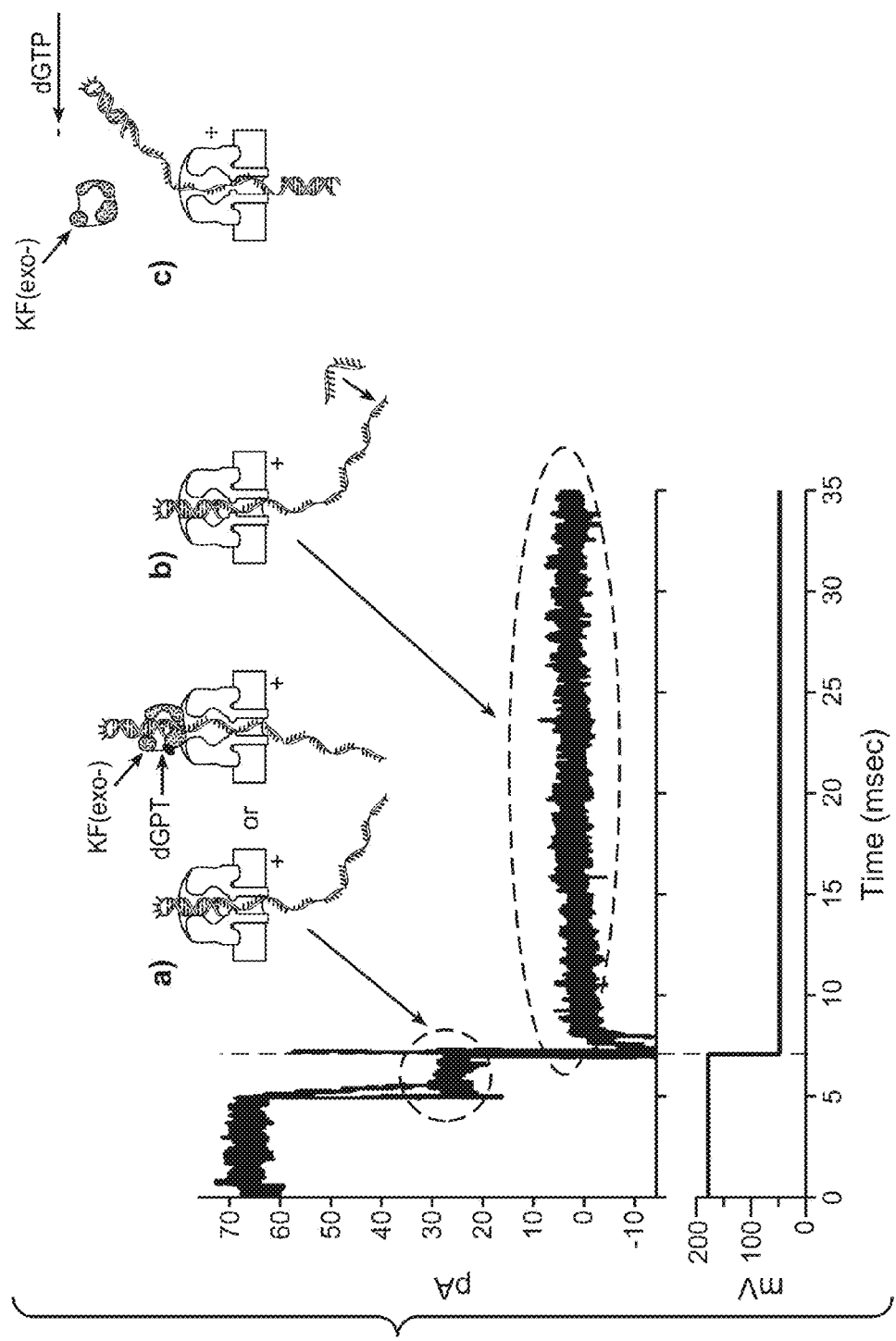
FIG. 17A shows steps (a)-(c)
Figure 17B:
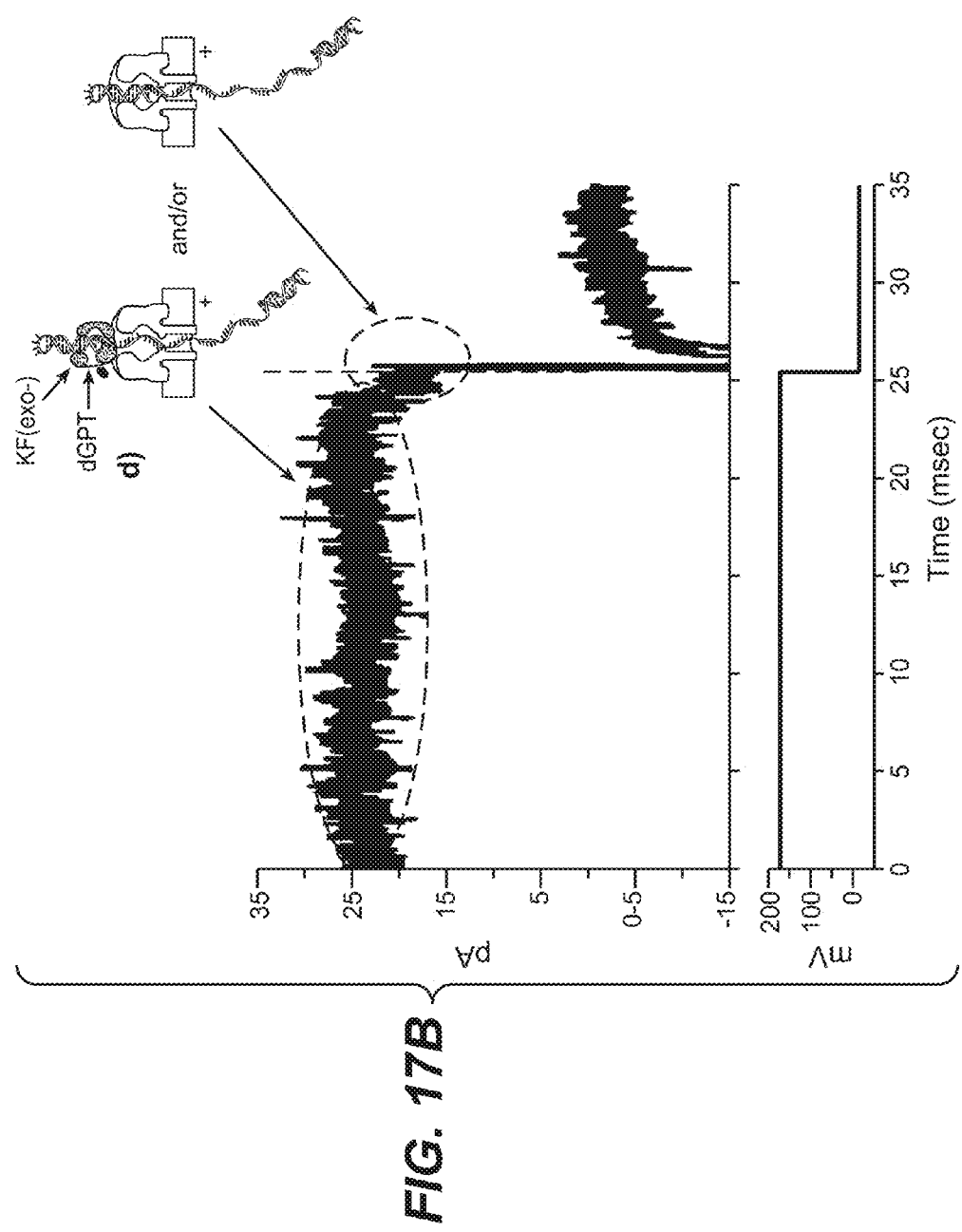
FIG. 17B shows step (d). (a) Captured hairpin or hairpin bound with KF at 180 mV. (b) Hairpin was held in vestibule at 50 mV for trans-side primer to anneal (20 sec). (c) Fished for KF at −20 mV for 5 sec. (d) 180 mV applied to check for presence of KF. If enzyme binding does not occur, bare DNA was immediately detected in the pore. Otherwise, the FSM waited for KF to dissociate, leaving hairpin in vestibule (20 pA terminal step). In both cases, once bare DNA is present in the pore, the FSM reverses the voltage (−20 mV) before the hairpin unzips to fish for another KF. Steps (c) through (d) were repeated until the hairpin translocated.

With voltage applied, DNA was drawn through the pore with the 5' end translocating first. When a 20 pA event characteristic of a ssDNA translocation event was detected, the FSM reduced the potential to 50 mV, a level sufficient enough to hold the molecule in the pore but not strong enough to shear the hairpin. If a 24 pA event characteristic of enzyme-bound DNA was detected, application of voltage was continued until the enzyme dissociated, leaving the bare DNA in the pore, at which point the voltage was reduced to 50 mV to hold the molecule in the pore. The molecule was held in the pore for 20 sec, a time found to be sufficient for the 20mer primer to anneal to the 5' end of the DNA at 2 μM primer concentration. With both ends of the DNA consisting of 20mer double-stranded segments, the molecule was restrained from immediately translocating. After the primer annealing waiting time, the FSM reversed the voltage to −20 mV, pulling the DNA toward the cis side of the pore with enough force to dangle it in solution but not to shear the trans-side primer. The voltage stayed at −20 mV for 5 sec, after which the FSM changed the voltage to 180 mV to diagnose the identity of the molecule in the pore; either DNA alone, DNA/KF binary complex, or DNA/KF/dGTP ternary complex. If enzyme-bound, as presumed if ~24 pA is observed, the FSM monitored the current signal for the 20 pA terminal step, the point when KF has dissociated but before the DNA translocates, to reverse the voltage back to −20 mV to attempt to capture another KF. If the FSM failed to detect the DNA molecule before it translocated, the current returned to the open channel current of ~60 pA, and the FSM would monitor the current for another DNA translocation event and repeat the fishing process (FIG. 17). If no enzyme is captured during a particular fishing attempt, the FSM tried fishing again until enzyme capture did occur. For the data analyzed from this experiment, five DNA copies were captured and used to fish for KF. Long dwell time events (that is, events >20 msec) were recorded for 95.1% of fishing attempts though no analysis has been done to determine the number of KF dissociation events that were correctly reacted to by the FSM.

After performing the initial proof-of-concept experiments, a second run of fishing experiments were run that yielded better results. Using a fishing time of 0.521 seconds, the FSM captured eight copies of the same DNA hairpin and reacted to 337 potential KF dissociation events over a time period of 380 seconds. Post analysis of the data shows the FPGA correctly detected and reacted to an enzyme dissociation event for 71.86% of KF captures, for example, 74 of the 337 potential dissociation events were false positives.

Example XXVII

Mitigating False-Enzyme Dissociation Detection

In the data presented above, the dissociation of the enzyme is detected by mean filtering the nanopore current signal and checking to see if it is within a chosen amplitude range. This method of smoothing yielded a large number of false detections. As an improvement to this filtering scheme, an exponentially weighted moving average (EWMA) filter can replace the mean filter that the FPGA used. The EWMA filter is a digital implementation of an analog RC filter, commonly used for signal smoothing in electrical engineering applications. The filter calculates a moving average that places exponentially less significance on past samples. EWMA filtering also performs signal smoothing more efficiently than a simple moving average due to its recursive implementation. However, experimental testing still needs to be done to tune the filter for nanopore current signal analysis.

To more robustly detect enzyme dissociation events, a KF dissociation check needs to be implemented to ensure fishing is being done with bare DNA. When the FPGA detects KF dissociation, it will fish for a period of time sufficiently fast so KF will not bind and then it will check the DNA for the presence of enzyme. If only bare DNA is diagnosed (current is ~20 pA), then the enzyme has dissociated and the system can attempt to capture another enzyme. This check is important for performing experiments to collect information on repeat events. For the data to be valid and statistically accurate, each detected event must be a new enzyme binding event.

The majority of long dwell time events correspond to strong KF binding events, for example, the next dNTP to be added to the template strand is present in the nanopore system, when saturating levels of KF and the correct dNTP are present. Multiple long dwell time events in a row improve confidence in base identification because repeated sequential long dwell time events occur even less often when the correct dNTP to be added is absent than when it is present. Here is where KF fishing will show its utility. Separate work is being done to model the dwell time events as a Poisson process so a Phred quality score can be applied to a base identity diagnosis based on the number of repeated sequential long dwell time events. The Phred system is an accuracy metric used commonly in DNA sequencing. For example, a 90% accurate call would be a $Q_{10}$ on the Phred scale and a 99% accurate call would be $Q_{20}$. $Q_{20}$ is considered the standard level of quality in DNA sequencing at the time of writing.

Another method to improve the detectability of the current step at the end of enzyme events is to use a longer hairpin and run the experiments at a higher voltage. The signal-tonoise of the channel current will improve due to higher ion flow through the channel, making the terminal steps more prominent.

Example XXVIII

Voltage Titration Experiments

A more quantitative connection between the amplitude and duration of the terminal step and the applied voltage may be made. The goals here are to reveal the repeatability of the terminal step and show how its structure is consistent with DNA alone at different voltages. An in-depth characterization of the terminal step allows for better control of the terminal step. Constant voltage experiments are run at four different voltages with DNA alone as well as DNA/KF/dNTP ternary complex, using saturating levels of each substrate (1 µM, 2 µM, and 200 µM respectively). Voltages are 220, 200, 180, and 160 mV. A 24 bphp is used rather than the 20 bphp used in the other tethered experiments to extend the dwell time at higher voltages. Higher voltages are run first to determine a practical upper limit for an applied voltage that yields detectable terminal step event durations (≥1 msec).

Example XXIX

Terminal Step Control Experiments

As described above, it is necessary to show accurate detection and reaction to the terminal step. As stated earlier, 97% of enzyme-bound events showed the terminal step, therefore, this is the theoretical maximum detection rate. Detection and reaction to the terminal step will be shown by voltage reversal upon detection, aggregating the terminal step duration. A high probing voltage, as used above, gives more resolution between the bound and unbound current levels. Experiments are run with DNA alone as well as DNA/KF/dNTP ternary complex, using saturating levels of each substrate. Robustness to false positives may be shown by verifying accurate detection offline.

Example XXX

Terminal Step Control Experiments: Tethered DNA Configuration with Fishing Time Titration A repeat of what was achieved above is performed but with tethered DNA. Titration of the fishing time is performed to reproduce the ratio of DNA alone events to ternary complex events comparable to those in the non-tethered DNA experiments. This information helps set limits on the fishing time to maintain representative sampling of the contents of the cis well. Experiments are run with DNA alone as well as DNA/KF/dNTP ternary complex; using saturating levels of each substrate.

Example XXXI

Fishing Titration Experiments

Titration of KF and dGTP are performed. The percentage of long events are recorded as a function of KF and dGTP concentration. Experiments are run at the same high capture voltage as above. The same concentration intervals for KF and dGTP as in the supplement of Benner et al (2007) Sequence specific detection of DNA polymerase binding using a nanopore-based state machine. Submitted to Nature Methods) are used: (KF=[0, 0.25, 0.5, 1.0, 2.0, 2.0, 2.0, 2.0, 2.0, 2.0, 2.0, 2.0] μM; dGTP=[0, 0, 0, 0, 0, 2.5, 7.5, 15, 30, 60, 120, 200] μM).

Example XXXII

Other Enzyme Studies the FPGA/FSM Nanopore System can Also be Used for Other Enzyme Studies Applying voltage ramps upon capture of DNA/enzyme complexes can produce data to calculate bond energy landscapes using voltage force spectroscopy. Also, DNA's interaction with the pore can be characterized using feedback control of the applied voltage. Regulation of enzyme catalysis can be by achieved applying tension to DNA occupying the pore, counteracting the enzymes' processive force.

Example XXXIII

Blocking Oligonucleotide (Oligomer) can Limit DNA Polymerase Activity at a Nanopore A DNA primer/template duplex (about 1 μM) in a solution containing all four dNTP (about 200 uM) substrates and $Mg^{2+}$ (about 5 mM), and a processive DNA polymerase (about 1 uM) is placed in contact with a single nanopore (for example, a-hemolysin). A voltage is applied such that negatively charged DNA is drawn into the pore. The primer/template duplex is also annealed to a sequence specific molecule such as the ones shown in FIG. 19. These blocking molecules either inhibit binding of the polymerase at the initiation site or they allow binding but hinder polymerase-catalyzed strand synthesis. The blocking molecule is unzipped under the effect of the applied voltage (FIG. 22) and synthesis can ensue. In the case of blocking molecules 19(d) to 19(g) in FIG. 19, the dC tail at the 3"end favors the unzipping process in the pore. The important point of this technology is that only the strand captured by the nanopore is unlocked from the blocking oligomer at the instant it is to be examined.

FIG. 20 shows blocking oligomer inhibition of bulk phase primer extension (DNA synthesis) by T7 DNA polymerase (exo-). Methylene blue-stained denaturing PAGE of reaction products following incubation for 40 minutes in nanopore buffer at 23° C. with the components listed below for each lane:

| lane | reaction components |
|---|---|
| 1 | primer/template, T7DNAP, dNTPs |
| 2 | primer/template, T7DNAP |
| 3 | primer/template |
| 4 | primer/template, dNTPs, T7DNAP, blocking oligomer e.ii |
| 5 | primer/template, blocking oligomer e.ii |
| 6 | primer/template, dNTPs, T7DNAP, blocking oligomer e.i |
| 7 | primer/template, dNTPs, blocking oligomer e.i |
| 8 | primer/template, dNTPs, T7DNAP, blocking oligomer d |
| 9 | primer/template, blocking oligomer d |

Arrows below the gel highlight key findings: Lane 1 shows the loss of the primer band and concomitant appearance of extension products in the presence of T7 DNA polymerase and dNTPs. The extension products do not appear if polymerase or dNTPs are omitted from the reaction (FIG. 20, lanes 2 and 3). Addition of blocking oligomer e.ii prevents full length primer extension in the presence of enzyme and dNTPs (lane 4); a small amount of single-nucleotide addition product is observed. Blocking oligomers d (lane 8) or e.i (lane 6) yield partial inhibition of primer extension.

Example XXXIV

The Nanopore Device Reliably Reports Capture of Polymerase-DNA-dNTP Complexes Formed in the Bulk Phase (FIG. 21)

The letters (a-d) above indicated features in the current trace (FIG. 21) correspond to the letters in the cartoon scheme. (a) Absent DNA, the open channel ionic current through the α-hemolysin nanopore is ~53 pA at 160 mV applied potential in 0.3M KCl. (b) The capture of a polymerase/DNA/dNTP complex causes the current to drop to a characteristic enzyme-bound state level ($I_{EBS}$). This current reduction occurs when the bound enzyme, which is too large to enter the pore vestibule, holds the duplex portion of the DNA substrate atop the pore, with the single-stranded template suspended in the pore lumen. (c) Upon voltage-promoted enzyme dissociation, the duplex DNA segment is drawn into the pore vestibule, causing a further current decrease. When DNA that is not enzyme bound is captured, this lower current is the only level that is detected. (d) The translocation of the DNA leaves the pore unoccupied and the current returns to the open channel amplitude. A 2-D plot of dwell time vs amplitude of hundreds of similar events is also included.

Example XXXV

Nanopore Evidence that Blocking Oligomers Prevent T7 DNA Polymerase Binding in Bulk Phase FIG. 22 demonstrates how DNA primer/template is pre-annealed with blocking oligomer e.ii then added to the nanopore chamber in the presence of T7 DNA pol (exo-) and the dGTP complement to the dC template base at n=0. The letters (a)-(e) above features in the current trace correspond to the letters in the cartoon scheme. (a) Open channel current is observed when no molecule is in the pore. (b) The pre-annealed blocking oligomer prevents the binding of the T7 DNAPol (exo-) to the DNA and just DNA can be captured in the pore, which produces a low amplitude current trace. (c) The blocking oligomer is unzipped against the pore and (d) the DNA template/primer duplex drops into the nanopore vestibule. (e) The translocation of the DNA leaves the pore unoccupied and the current returns to the open channel amplitude.

Example XXXVI

Binding of T7 DNA pol to Individual DNA Substrates is Activated Electronically at the Nanopore The utility of a given blocking oligomer is determined by testing whether it is readily unzipped from the captured DNA template by the nanopore electric field, rendering individual molecules that were blocked in bulk phase competent to bind enzyme after capture. Letters (a)-(e) in the current trace correspond to letters in the cartoon scheme shown in FIG. 23. (a) The DNA primer/template is pre-annealed with the blocking oligomer. Upon capture of the DNA template by the nanopore electric field, the polydC tail of the blocking oligomer is wedged against the exterior of the αα-HL heptamer causing the oligomer to unzip as the DNA template is driven further into the pore. When the capture level is detected, the voltage is reduced and the DNA strand in the trans compartment is allowed to anneal to a ssDNA reverse complement. This forms a duplex DNA dumbbell, non-covalently tethering the DNA in the pore. At this membrane potential, the n=0 position of the DNA template is protected from interacting with polymerase. (b) The potential is reversed to drive the DNA primer/template up into the cis compartment where it can bind polymerase and dNTP substrates forming a ternary complex. The length of this 'fishing' period is determined by the user, and can range from 0.5 ms up to an arbitrarily long period of several seconds. (c) Following fishing, the membrane voltage is reversed again, drawing the DNA template back toward the nanopore orifice. If an enzyme molecule is bound to the DNA during the 'fishing' time, an ionic current characteristic of enzyme binding ($I_{EBS}$) is detected. (d) Upon voltage-promoted enzyme dissociation, the duplex DNA segment is drawn into the pore vestibule, causing a further current decrease to a level characteristic of unbound DNA. The FSM logic tests for this current level. When unbound DNA is detected, the FSM executes a return to the negative voltage fishing period for a new fishing cycle. (e) The process is repeated until the DNA translocates and open channel current is detected. At this point the system returns to the initial state until another blocked DNA is captured.

The current trace and the accompanying 2-D plot of dwell time vs. amplitude for hundreds of similar events illustrate the key finding: under the same physico-chemical conditions as in the experiment illustrated in FIG. 22, FSM logic allows electronic activation of the substrate by unzipping of the blocking oligomer, and controlled detection of enzyme binding to the individual DNA substrate tethered in the nanopore.

Example XXXVII

Figure 24:
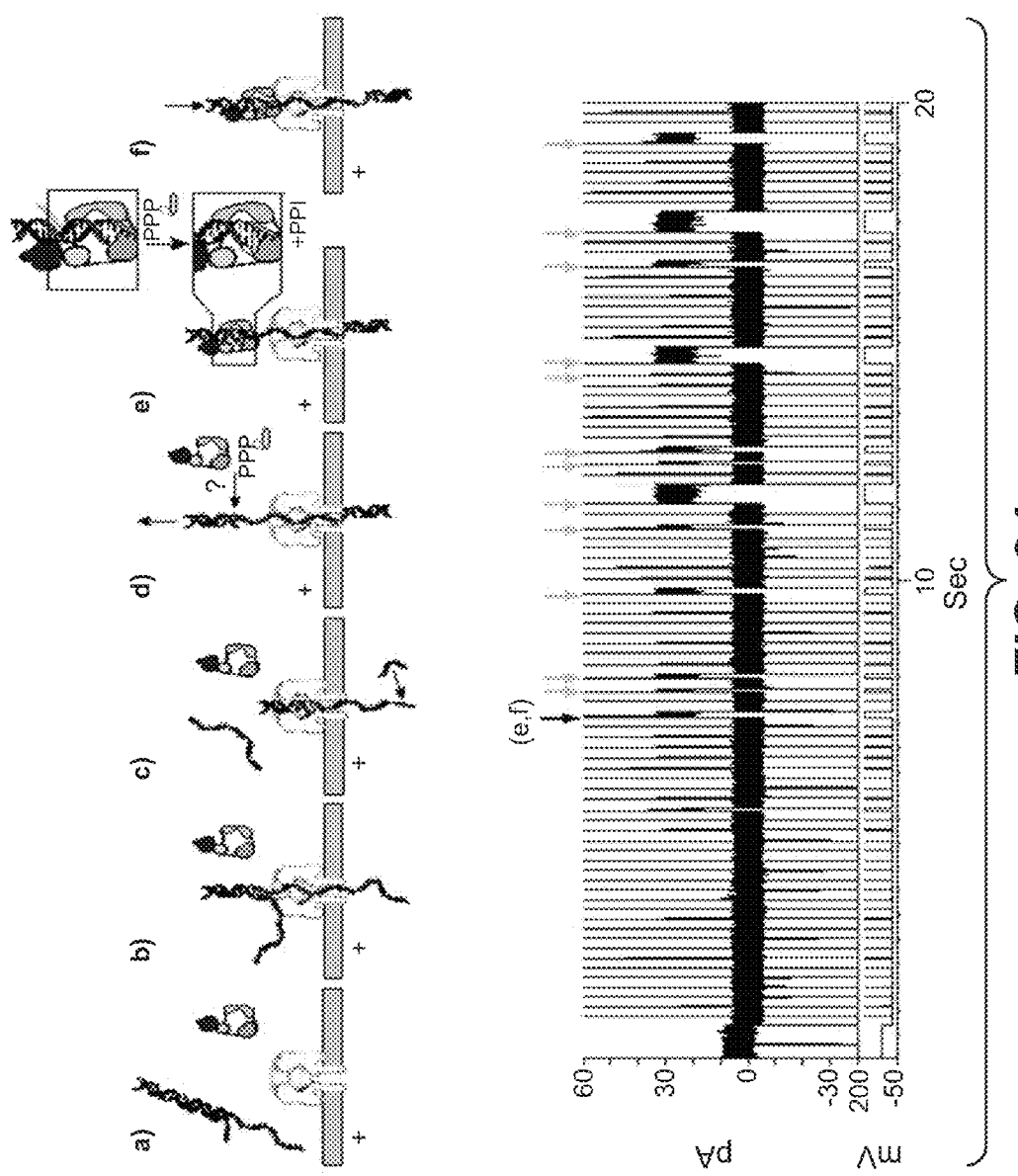
FIG. 24 shows that polymerase-catalyzed nucleotide addition proceeds at the nanopore following unzipping of the blocking oligomer.

Polymerase-Catalyzed Nucleotide Addition Proceeds at the Nanopore Following Unzipping of the Blocking Oligomer (FIG. 24)

FIG. 24(a) DNA primer/template bearing the 3'-OH terminus required for polymerase-catalyzed primer extension is pre-annealed with blocking oligomer, and added to the nanopore chamber. (b) upon template capture, the blocking oligomer is unzipped and (c) a tethering oligomer is annealed to the DNA on the trans side of the nanopore. (d) When the membrane potential is reversed, the activated dsDNA/ssDNA junction at n=0 is exposed to T7 DNA polymerase and substrates in the cis compartment. If the first round of catalysis does not occur during the programmed fishing interval, re-probing of the dsDNA/ssDNA junction results in ionic currents characteristic of DNA that is not enzyme bound. In the current trace shown, there were ~30 consecutive probing steps of this class from 0 to 7 seconds. (e) With dideoxy-GTP (100 uM), and dATP (400 uM), present in the nanopore cis chamber, the following steps can occur, in this order: T7 DNA pol binding, catalysis of ddGTP incorporation opposite the templating dC nucleotide at n=0, and dATP binding to form a stable ternary complex. If these steps occur during the fishing interval a ternary complex is drawn back atop the pore during the probing step. This yields an event with a higher current (about 29 pA) and a significantly longer dwell time (steps (e), (f) in the cartoon, and the black arrow at ~7 seconds). Subsequent $I_{EBS}$ values are observed at higher frequency (gray arrows) because the chemistry step was completed at 7 sec, and only ternary complex formation is required thereafter.

Example XXXVIII

DNA Translocation Through the Nanopore in Real Time Driven by T7 DNA Polymerase (FIG. 25)

FIG. 25 (a) shows the template (SEQ ID NO:1) used in 10 nt addition synthesis experiment. The binding site for the 23 mer synthesis primer is underlined, the unique G residue at position+33 is in red, and the abasic insert is shown as blue Xs. Sequences at the 5"end of the template, which include the binding site for the tethering oligomer on the trans side of the nanopore, is not shown. (b) Current trace for fishing experiment in which T7DNAP catalyzes the addition of 10 nucleotides up to a unique ternary complex endpoint. The fish and probe protocol used for this experiment is detailed in FIGS. 18 & 19. The fish time was 20 ms with a 90 mV probing step. (i) As synthesis begins from the 23 mer primer, standard DNA residues occupy the pore lumen, affording little discrimination between the enzyme bound state (EBS) and the terminal current step when complexes are drawn back to the pore during the probing step. (ii) As nucleotides are added during subsequent fishing intervals, the enzyme advances on the template, drawing the abasic insert closer to the pore lumen in single nt steps, thus higher amplitude EBS events emerge. A probing event with three discrete amplitude levels is shown, corresponding to the two EBS positions (9 pA and 11 pA) before the ternary endpoint (12 pA). Once this endpoint is reached, whether or not subsequent fishing events yield an EBS is determined by the probability of ternary complex assembly during the fishing interval. Thus the three-amplitude event was followed by a unbound DNA event (iii), followed after next fishing interval by a long ternary complex event (iv) confirming that the 12 pA endpoint had been reached.

Example XXXVIX

Screening Molecules for Specific Binding with the Polynucleotide or Protein Conjugate The polynucleotide, or fragments thereof, are labeled with $^{32}$P-dCTP, Cy3-dCTP, or Cy5-dCTP (Amersham Pharmacia Biotech), or with BIODIPY or FITC (Molecular Probes, Eugene Oreg.), respectively. Similarly, the conjugate comprising a complex of polynucleotide and a binding protein thereof can be labeled with radionucleide or fluorescent probes. Libraries of candidate molecules or compounds previously arranged on a substrate are incubated in the presence of labeled polynucleotide or protein. After incubation under conditions for either a polynucleotide or amino acid molecule, the substrate is washed, and any position on the substrate retaining label, which indicates specific binding or complex formation, is assayed, and the ligand is identified. Data obtained using different concentrations of the polynucleotide or protein are used to calculate affinity between the labeled polynucleotide or protein and the bound molecule.

Example XXXX

Screening Drug Candidates for Specific Binding with the Polynucleotide or Protein Conjugate A drug candidate, such as a statin, is introduced into a chamber as described herein, the chamber comprising a polynucleotide complex, a blocking oligomer, and a transcription factor having a binding affinity for the statin of at least $10^8$ M. The transcription factor comprises conserved domains that bind to a conserved element that is encoded by a portion of the polynucleotide complex. In vivo, for example in the liver, the statin binds to the transcription factor (TF) that activates binding of the transcription factor to the conserved element, thereby recruiting RNA polymerase to the transcriptional activation site. The sequence of the blocking oligomer is designed to prevent binding of the TF in the presence of a statin having a binding affinity of at least $10^8$ M. When the polynucleotide complex/blocking oligomer is translocated to and thence partially through the nanopore, the blocking oligomer is stripped from the polynucleotide complex, thereby revealing the binding site of the polynucleotide complex for the activated TF. Candidate statins are then screened to identify those with binding affinity for the TF that correlates with the release of blocking oligomer and partial translocation of and subsequent catalysis of the polynucleotide complex through the nanopore.

Those skilled in the art will appreciate that various adaptations and modifications of the just-described embodiments can be configured without departing from the scope and spirit of the invention. Other suitable techniques and methods known in the art can be applied in numerous specific modalities by one skilled in the art and in light of the description of the present invention described herein. Therefore, it is to be understood that the invention can be practiced other than as specifically described herein. The above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A method for controlling movement of a polynucleotide using voltage control, the method resulting in identifying a sequence of a polynucleotide, the method comprising the steps of:
    a) providing two separate adjacent chambers comprising a medium, an interface between the two chambers, the interface comprising a material having at least one channel therethrough and wherein one chamber is on the cis-side of the interface and the other chamber is on the trans-side of the interface, the channel so dimensioned as to allow sequential monomer-by-monomer passage from the cis-side of the channel to the trans-side of the channel of only one polynucleotide strand at a time;
    b) providing an enzyme having binding activity for a polynucleotide, said enzyme being a polymerase; providing a blocking oligomer; providing a polynucleotide complex, wherein a portion of the polynucleotide complex is double-stranded and a portion is single-stranded; providing a complementary oligomer, wherein the complementary oligomer is complementary to a portion of the single stranded polynucleotide; providing a substrate;
    c) introducing the polynucleotide complex into one of the two chambers; introducing the blocking oligomer into the same chamber; allowing the blocking oligomer to bind to the polynucleotide complex;
    d) introducing the enzyme into the same chamber; introducing the complementary oligomer into the other chamber;
    e) applying a potential difference between the two chambers, thereby creating a first polarity, the first polarity causing the single stranded portion of the polynucleotide to transpose through the channel to the trans-side thereby stripping the blocking oligomer from the polynucleotide complex;
    f) measuring the electrical current through the channel after removal of the blocking oligomer;

g) providing a potential difference allowing the complementary oligomer to bind to the single-stranded polynucleotide;

h) reversing the potential difference, thereby creating a reverse polarity; providing conditions to allow the enzyme to bind to the polynucleotide complex; providing conditions to allow the enzyme to incorporate substrate into the polynucleotide, thereby increasing length of the double-stranded portion;

i) reversing the potential difference a second time;

j) measuring the electrical current through the channel, thereby detecting a polynucleotide having incorporated substrate or a polynucleotide bound to the enzyme;

k) repeating any one of steps h) through j), thereby controlling movement of the polynucleotide in order to determine at least a portion of the sequence of the polynucleotide.

2. The method of claim 1 further comprising comparing the electrical current value obtained at step f) with the current value obtained at step j).

3. The method of claim 1 further comprising comparing the electrical current value obtained at step j) with the electrical current value obtained at a later time.

4. The method of claim 1 wherein the step of allowing the blocking oligomer to bind to the polynucleotide complex is performed prior to introducing the polynucleotide complex and the blocking oligomer into the same chamber, and is followed by a step of introducing the polynucleotide complex and the blocking oligomer into the chamber.

5. The method of claim 1 where there are a plurality of channels.

6. The method of claim 1 wherein the blocking oligomer is an oligonucleotide having partial complementarity to a portion of the polynucleotide complex.

7. The method of claim 6 wherein the oligonucleotide having partial complementarity to a portion of the polynucleotide complex further comprises a duplex structure, formed with a portion of the polynucleotide complex that is single-stranded, at one end of the oligonucleotide and a blocking moiety at the other end of the oligonucleotide.

8. The method of claim 6 wherein the oligonucleotide having partial complementarity to a portion of the polynucleotide complex further comprises a hairpin loop structure at one end of the oligonucleotide.

9. The method of claim 7 wherein the blocking moiety is selected from the group consisting of acridine, a peptide nucleic acid, a 2'-O-methyl group, a fluorescent compound, DAPI, an anthocyanin, green fluorescent protein (GFP), β-glucuronidase, luciferase, Cy3, Cy5, a derivatized nucleotide, and a nucleotide isomer.

10. The method of claim 1 wherein the complementary oligomer is selected from the group consisting of an oligonucleotide complementary to the polynucleotide, a peptide nucleic acid, a locked nucleic acid, a derivatized nucleotide, a nucleotide isomer and a DNA aptamer.

11. The method of claim 1 wherein the enzyme is selected from the group consisting of DNA polymerase, and RNA polymerase.

12. The method of claim 1 further comprising the steps of providing at least one reagent that initiates enzyme activity; introducing the reagent to the chamber comprising the polynucleotide complex; and incubating the chamber at a temperature sufficient to maintain enzyme activity.

13. The method of claim 12, wherein the reagent is a cofactor.

14. The method of claim 13, wherein the cofactor is selected from the group consisting of $Mg^{2+}$, $Mn^{2+}$, $Ca^{2+}$, ATP, $NAD^+$, $NADP^+$, and S-adenosylmethionine.

15. The method of claim 1, wherein the medium is electrically conductive.

16. The method of claim 1, wherein the medium is an aqueous medium.

17. The method of claim 1 wherein the substrate comprises a ribonucleotide selected from the group consisting of dATP, dGTP, TTP, dCTP, UTP, dUTP, ATP, GTP, TTP, CTP, and tRNA.

* * * * *

```
SEQUENCE LISTING

<160> NUMBER OF SEQ ID NOS: 1

<210> SEQ ID NO 1
<211> LENGTH: 56
<212> TYPE: DNA
<213> ORGANISM: Artificial
<220> FEATURE:
<223> OTHER INFORMATION: Synthetically prepared oligonucleotide sequence
<220> FEATURE:
<221> NAME/KEY: misc_feature
<222> LOCATION: (6)..(11)
<223> OTHER INFORMATION: abasic insert

<400> SEQUENCE: 1
atattnnnnn ncattcattc agagctcact atcgcattct catgcaggtc gtagcc      56
```